US009029406B2

(12) United States Patent
Lerchen et al.

(10) Patent No.: US 9,029,406 B2
(45) Date of Patent: May 12, 2015

(54) N-CARBOXYALKYLAURISTATINS AND USE THEREOF

(75) Inventors: Hans-Georg Lerchen, Leverkusen (DE); Sherif El Sheikh, Essen (DE); Beatrix Stelte-Ludwig, Wülfrath (DE); Joachim Schuhmacher, Wuppertal (DE); Mark Gnoth, Mettmann (DE)

(73) Assignee: Seattle Genetics, Inc, Bothell, WA (US)

( * ) Notice: Subject to any disclaimer, the term of this patent is extended or adjusted under 35 U.S.C. 154(b) by 0 days.

(21) Appl. No.: 14/004,699

(22) PCT Filed: Mar. 12, 2012

(86) PCT No.: PCT/EP2012/054294
§ 371 (c)(1),
(2), (4) Date: Nov. 19, 2013

(87) PCT Pub. No.: WO2012/123423
PCT Pub. Date: Sep. 20, 2012

(65) Prior Publication Data
US 2014/0080763 A1    Mar. 20, 2014

(30) Foreign Application Priority Data

Mar. 16, 2011  (EP) .................................... 11158481

(51) Int. Cl.
| C07D 207/333 | (2006.01) |
| C07D 413/12 | (2006.01) |
| C07D 403/12 | (2006.01) |
| A61K 31/4025 | (2006.01) |
| A61K 31/4245 | (2006.01) |
| A61K 38/07 | (2006.01) |
| C07K 5/02 | (2006.01) |
| A61K 45/06 | (2006.01) |
| C07K 5/103 | (2006.01) |
| A61K 38/00 | (2006.01) |
| A61K 47/48 | (2006.01) |

(52) U.S. Cl.
CPC ................. *A61K 38/07* (2013.01); *A61K 38/00* (2013.01); *C07K 5/0205* (2013.01); *A61K 45/06* (2013.01); *C07K 5/101* (2013.01); *A61K 47/48261* (2013.01)

(58) Field of Classification Search
None
See application file for complete search history.

(56) References Cited

U.S. PATENT DOCUMENTS

| 6,884,869 B2 | 4/2005 | Senter et al. |
| 8,288,352 B2 | 10/2012 | Doronina et al. |
| 2002/0147138 A1 | 10/2002 | Firestone et al. |
| 2009/0111756 A1 | 4/2009 | Doronina et al. |
| 2009/0280056 A1 | 11/2009 | Dennis et al. |
| 2013/0066055 A1 | 3/2013 | Lerchen et al. |
| 2013/0095123 A1 | 4/2013 | Lerchen et al. |
| 2013/0122024 A1 | 5/2013 | Lerchen et al. |
| 2013/0157960 A1 | 6/2013 | Lerchen et al. |
| 2013/0261064 A1 | 10/2013 | Lerchen et al. |

FOREIGN PATENT DOCUMENTS

| WO | 96/18408 A1 | 6/1996 |
| WO | 99/35164 A1 | 7/1999 |
| WO | 01/18032 A2 | 3/2001 |
| WO | 02/088172 A2 | 11/2002 |
| WO | 03/008378 A1 | 1/2003 |
| WO | 03/026577 A2 | 4/2003 |
| WO | 2004/010957 A2 | 2/2004 |
| WO | 2005/081711 A2 | 9/2005 |
| WO | 2007/008603 A1 | 1/2007 |
| WO | 2007/008848 A2 | 1/2007 |
| WO | 2008/052187 A2 | 5/2008 |
| WO | 2009/117531 A1 | 9/2009 |
| WO | 2011/154359 A1 | 12/2011 |

OTHER PUBLICATIONS

Vallianou, N., et al., Anti-Cancer Agents in Medicinal Chemistry, 14:706 (2014) Abstract only.*
Hörig et al., J. Translational Med. 2:44 (2004).*
International Search Report (Form PCT/ISA/210) issued on Aug. 18, 2011, by the European Patent Office in International Application No. PCT/EP2011/059300. (4 pages).
International Search Report (Form PCT/ISA/210) issued on Apr. 17, 2012, by the European Patent Office in corresponding International Application No. PCT/EP2012/054294. (9 pages).
Notification Concerning Transmittal of International Preliminary Report on Patentability (Forms PCT/IB/326 and PCT/IB/373) and the Written Opinion of the International Searching Authority (Form PCT/ISA/237) issued on Dec. 20, 2012, by the International Bureau of WIPO in International Application No. PCT/EP2011/059300. (10 pages).
International Search Report (Form PCT/ISA/210) issued on Nov. 8, 2011, by the European Patent Office in International Application No. PCT/EP2011/066658. (3 pages).
Written Opinion of the International Searching Authority (Form PCT/ISA/237) issued on Nov. 8, 2011, by the European Patent Office in International Application No. PCT/EP2011/066658. (12 pages).
Arap et al., "Cancer Treatment by Targeted Drug Delivery to Tumor Vasculature in a Mouse Model" Science, (Jan. 16, 1998), vol. 279, No. 5349, pp. 377-380.

(Continued)

*Primary Examiner* — Michael Barker
(74) *Attorney, Agent, or Firm* — Buchanan Ingersoll & Rooney PC

(57) ABSTRACT

The present application relates to new derivatives, substituted on the N terminus by a carboxyalkyl group, of monomethylauristatin E and monomethylauristatin F, to processes for preparing these derivatives, to the use of these derivatives for treating and/or preventing diseases, and to the use of these derivatives for producing medicaments for treating and/or preventing diseases, more particularly hyperproliferative and/or angiogenic disorders such as cancer disorders, for example. Such treatments may be applied as a monotherapy or else in combination with other medicaments or further therapeutic measures.

13 Claims, No Drawings

(56) References Cited

OTHER PUBLICATIONS

Bajjuri et al., "The Legumain Protease-Activated Auristatin Prodrugs Suppress Tumor Growth and Metastasis without Toxicity" ChemMedChem, (Jan. 3, 2011), vol. 6, Issue 1, pp. 54-59.

Doronina et al., "Enhanced Activity of Monomethylauristatin F through Monoclonal Antibody Delivery: Effects of Linker Technology on Efficacy and Toxicity" Bioconjugate Chemistry, (Jan.-Feb. 2006), vol. 17, No. 1, pp. 114-124.

Doronina et al., "Novel Peptide Linkers for Highly Potent Antibody-Auristatin Conjugate" Bioconjugate Chemistry, (Oct. 2008), vol. 19, No. 10, pp. 1960-1963.

Ducry et al., "Antibody-Drug Conjugates: Linking Cytotoxic Payloads to Monoclonal Antibodies" Bioconjugate Chemistry, (Jan. 2010), vol. 21, No. 1, pp. 5-13.

Karkan et al., "A Unique Carrier for Delivery of Therapeutic Compounds Beyond the Blood-Brain Barrier" PLoS ONE, (Jun. 25, 2008), vol. 3, Issue 6, pp. 1-14.

Lambert, "Drug-Conjugated Monoclonal Antibodies for the Treatment of Cancer" Current Opinion in Pharmacology, (Oct. 2005), vol. 5, No. 5, pp. 543-549.

Pettit et al., "Antineoplastic Agents 365. Dolastatin 10 SAR Probes" Anti-Cancer Drug Design, (Jun. 1998), vol. 13, No. 4, pp. 243-277.

Pettit, "The Dolastatins" Prog. Chem. Org. Nat. Prod. (1997), vol. 70, pp. 1-79.

Pettit et al., "Antineoplastic Agents 337. Synthesis of Dolastatin 10 Structural Modifications" Anti-Cancer Drug Design, (Oct. 1995), vol. 10, No. 7, pp. 529-544.

Senter, "Potent Antibody Drug Conjugates for Cancer Therapy" Current Opinion in Chemical Biology, (Jun. 2009), vol. 13, No. 3, pp. 235-244.

Wu et al., "Arming Antibodies: Propects and Challenges for Immunoconjugates" Nature Biotechnology, (Sep. 2005), vol. 23, No. 9, pp. 1137-1146.

* cited by examiner

N-CARBOXYALKYLAURISTATINS AND USE THEREOF

The present patent application relates to novel derivatives of monomethylauristatin E and monomethylauristatin F, substituted with a carboxyalkyl group on the N terminus, methods of synthesis of these derivatives, use of these derivatives for treatment and/or prevention of diseases and use of these derivatives for production of pharmaceutical drugs for treatment and/or prevention of diseases, in particular hyperproliferative and/or angiogenic diseases, such as the various forms of cancer, for example. Such treatments may be in the form of monotherapy or in combination with other drugs or other therapeutic measures.

Cancer is the result of uncontrolled cell growth of a wide variety of tissues. In many cases, the new cells grow into existing tissue (invasive growth) or metastasize to remote organs. Cancer occurs in a wide variety of organs and the pathology often has a tissue-specific course. The term cancer is therefore a generic term that describes a large group of specific diseases of various organs, tissues and types of cells.

Early-stage tumors can in some cases be removed by surgical and radiotherapeutic measures. Metastatic tumors can usually be treated only palliatively by chemotherapeutic agents. The goal here is to find the optimum combination of prolonging life and improving the quality of life.

Most chemotherapeutic agents administered parenterally today are not distributed to the tumor tissue or tumor cells in a targeted manner but instead are nonspecifically distributed throughout the patient's body through systemic administration, i.e., at sites where exposure to the drug is often undesirable, such as in healthy cells, tissues and organs, for example. This may lead to adverse effects or even serious general toxic effects, which then often severely limit the therapeutically usable drug dosage range or necessitate complete cessation of the medication.

The improved and selective availability of these chemotherapeutic agents in the tumor cell or the immediate surrounding tissue and the associated increase in effect, on the one hand, and minimization of toxic side effects, on the other hand, have therefore for many years been the focus of work in developing new chemotherapeutic drugs. There have been numerous attempts so far to develop efficient methods for introducing drugs into the target cell. However, it is still a difficult task to optimize the association between the drug and the intracellular target and to minimize the intercellular distribution of the drug, e.g., to neighboring cells.

Monoclonal antibodies, for example, are suitable for targeted addressing of tumor tissue and tumor cells. The importance of such antibodies for clinical treatment of cancer has grown enormously in recent years based on the efficacy of such agents as trastuzumab (Herceptin), rituximab (Rituxan), cetuximab (Erbitux) and bevacizumab (Avastin) which have been approved in the meantime for treatment of individual specific tumor conditions (see, for example, G. P. Adams and L. M. Weiner, *Nat. Biotechnol.* 23, 1147-1157 (2005)). As a result, there has been a significant increase in interest in so-called immunoconjugates, in which an internalizing antibody directed against a tumor-associated antigen is bound covalently to a cytotoxic agent by a linking unit ("linker"). After introducing the conjugate into the tumor cell and then it splitting it off, the cytotoxic agent is released inside the tumor cell, where it can manifest its effect directly and selectively. In this way, the damage to normal tissue can be kept within significantly narrower limits in comparison with conventional chemotherapy for cancer (see, for example, J. M. Lambert, *Curr. Opin. Pharmacol.* 5, 543-549 (2005); A. M. Wu and P. D. Senter, *Nat. Biotechnol.* 23, 1137-1146 (2005); P. D. Senter, *Curr. Opin. Chem. Biol.* 13, 235-244 (2009); L. Ducry and B. Stump, *Bioconjugate Chem.* 21, 5-13 (2010)).

Instead of antibodies, binders from the field of small drug molecules may be used as binders to selectively bind to a specific "target" such as, for example, to a receptor (see, e.g., E. Ruoslahti et al., *Science*, 279, 377-380 (1998); D. Karkan et al., *PLoS ONE* 3 (6), e2469 (Jun. 25, 2008)). Conjugates of a cytotoxic drug and an addressing ligand having a defined cleavage site between the ligand and the drug for release of the drug are also known. One such "intended breaking point" may consist of a peptide chain, for example, which can be cleaved selectively at a certain site by a specific enzyme at the site of action (see, for example, R. A. Firestone and L. A. Telan, US Patent Application US 2002/0147138).

Auristatin E (AE) and monomethylauristatin E (MMAE) are synthetic analogs of the dolastatins, a special group of linear pseudopeptides, which were originally isolated from marine sources, and some of which have a very potent cytotoxic activity with respect to tumor cells (for an overview, see, for example, G. R. Pettit, *Prog. Chem. Org. Nat. Prod.* 70, 1-79 (1997); G. R. Pettit et al., *Anti-Cancer Drug Design* 10, 529-544 (1995); G. R. Pettit et al., *Anti-Cancer Drug Design* 13, 243-277 (1998)).

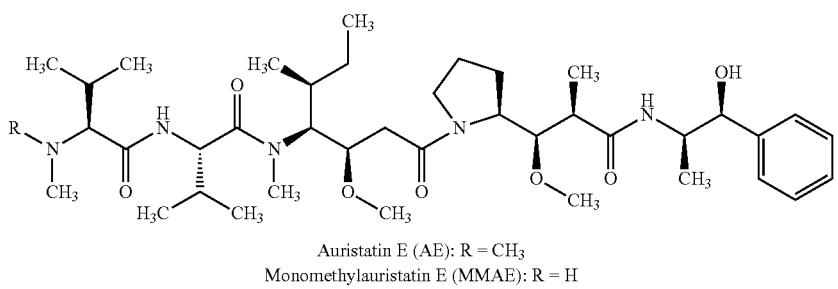

Auristatin E (AE): R = CH$_3$
Monomethylauristatin E (MMAE): R = H

However, MMAE has the disadvantage of a comparatively high systemic toxicity. Furthermore, when used in the form of antibody-drug conjugates (immunoconjugates), this compound is not compatible with linking units (linkers) between antibody and active ingredient/drug, which do not have any enzymatically cleavable intended breaking points (S. O. Doronima et al., *Bioconjugate Chem.* 17, 114-124 (2006)).

Monomethylauristatin F (MMAF) is an auristatin derivative with a C-terminal phenylalanine unit having only a moderate antiproliferative effect in comparison with MMAE. This can very likely be attributed to the free carboxyl group, which has a negative effect on the cell viability of this compound because of its polarity and charge. In this context, the methyl ester of MMAF (MMAF-OMe) has been described as a prodrug derivative, which has a neutral charge and can pass through the cell membrane; it also has an increased in vitro cytotoxicity, which is greater by several orders of magnitude in comparison with MMAF with respect to various carcinoma cell lines (S. O. Doronina et al., *Bioconjugate Chem.* 17, 114-124 (2006)). It may be assumed that this effect is caused by the MMAF itself, which is rapidly released by intracellular ester hydrolysis after the prodrug has been incorporated into the cells.

However, drug compounds based on simple ester derivatives are generally at risk of chemical instability due to a nonspecific ester hydrolysis, which is independent of the intended site of action, for example, due to esterases present in blood plasma. This can greatly restrict the usability of such compounds in treatment. In addition, auristatin derivatives such as MMAE and MMAF are also substrates for transporter proteins that are expressed by tumor cells, which can lead to the development of a resistance to these active ingredients.

The object of the present invention was therefore to identify novel auristatin compounds and supply them for the treatment of cancer in particular, such that these auristatin compounds have a stronger cytotoxic activity in whole-cell assays in comparison with monomethylauristatin F (MMAF), which has only a moderate efficacy, and/or have less pronounced substrate properties for transporter proteins. Such substances could also be especially suitable as toxophores for linking to proteins, such as antibodies in particular, or to low-molecular ligands to form (immuno-)conjugates having antiproliferative effects.

Monomethylauristatin F (MMAF) as well as various ester and amide derivatives thereof were disclosed in WO 2005/081711 A2. Additional auristatin analogs having a C-terminal amide-substituted phenylalanine unit are described in WO 01/18032 A2. MMAF analogs involving side chain modifications of phenylalanine are claimed in WO 02/088172 A2 and WO 2007/008603 A1, and WO 2007/008848 A2 describes those in which the carboxyl group of phenylalanine is modified. Additional auristatin conjugates linked via the N- or C-terminus are described in WO 2009/117531 A1 (see also S. O. Doronina et al., *Bioconjugate Chem.* 19, 1960-1963 (2008)).

The subject matter of the present invention is compounds of general formula (I):

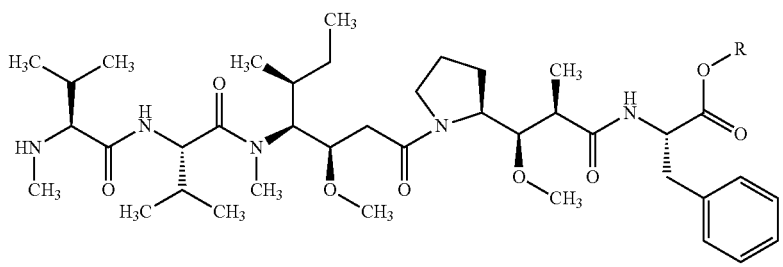

Monomethylauristatin F (MMAF): R = H
Monomethylauristatin F-methylester (MMAF-OMe): R = CH$_3$

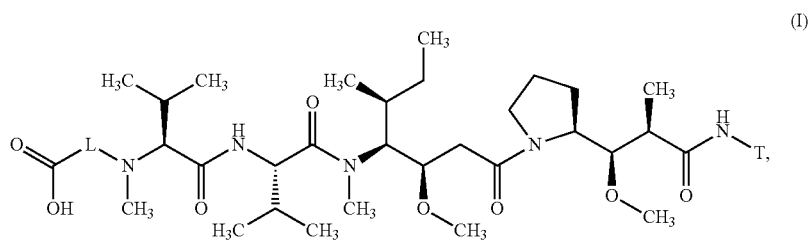

(I)

in which
L stands for linear (C$_1$-C$_{12}$)-alkanediyl, which may be substituted with methyl up to four times and in which (a) two carbon atoms in 1,2-, 1,3- or 1,4-relation to one another may be bridged by including the carbon atoms optionally between them to form a (C$_3$-C$_6$)-cycloalkyl ring or a phenyl ring, or (b) up to three CH$_2$ groups not vicinal to one another may be replaced by —O—,
and
T stands for a group of the formula

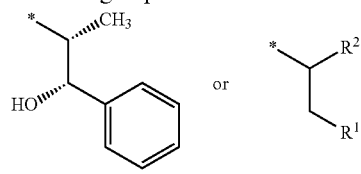

wherein
* denotes the linkage site to the nitrogen atom,
R$^1$ stands for phenyl or 1H-indol-3-yl, and
R² stands for hydrogen or a group of the formula

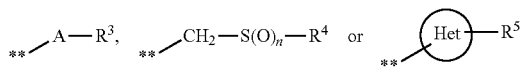

wherein
** denotes the respective linkage site to the radical of the respective group T,
A stands for linear ($C_1$-$C_4$)-alkanediyl or linear ($C_2$-$C_4$)-alkenediyl,
R³ stands for phenyl that may be substituted with ($C_1$-$C_4$)-alkoxycarbonyl or carboxyl,
n stands for the number 0, 1 or 2,
R⁴ stands for phenyl, benzyl or 2-phenylethyl which may be substituted with ($C_1$-$C_4$)-alkoxycarbonyl or carboxyl in the phenyl group
Het stands for a divalent 5-membered heteroaryl ring with up to three ring heteroatoms from the series N, O and/or S,
and
R⁵ stands for ($C_3$-$C_6$)-cycloalkyl, phenyl or ($C_1$-$C_4$)-alkyl, which may be substituted with phenyl,
wherein the aforementioned phenyl groups may in turn be substituted with ($C_1$-$C_4$)-alkoxycarbonyl or carboxyl,
as well as their salts and solvates and the solvates of the salts.

Compounds according to the invention include the compounds of formula (I) and their salts and solvates as well as the solvates of the salts, the compounds of the formulas given below that are covered by formula (I) and their salts and solvates as well as the solvates of the salts and the compounds covered by formula (I) and referred to below as exemplary embodiments as well as their salts and solvates as well as the solvates of the salts, as long as the compounds covered by formula (I) and listed below are not already the salts and solvates as well as the solvates of the salts.

The compounds according to the invention may exist in different stereoisomeric forms depending on their structure, i.e., in the form of configurational isomers or optionally also as conformational isomers (enantiomers and/or diastereomers, including those in atropisomers). The present invention therefore includes the enantiomers and diastereomers and their respective mixtures. The stereoisomerically uniform components can be isolated in a known way from such mixtures of enantiomers and/or diastereomers. Chromatographic methods, in particular HPLC chromatography on a chiral or achiral phase, are preferably used for this purpose.

If the compounds according to the invention can occur in tautomeric forms, then the present invention also includes all the tautomeric forms.

Within the scope of the present invention, the preferred salts are the physiologically safe salts of the compounds according to the invention. This also includes salts that are not suitable for pharmaceutical applications per se but may be used for isolating or purifying the compounds according to the invention, for example.

Physiologically safe salts of the compounds according to the invention include acid addition salts of mineral acids, carboxylic acids and sulfonic acids, for example, salts of hydrochloric acid, hydrobromic acid, sulfuric acid, phosphoric acid, methane sulfonic acid, ethane sulfonic acid, benzene sulfonic acid, toluene sulfonic acid, naphthalene disulfonic acid, acetic acid, trifluoroacetic acid, propionic acid, lactic acid, tartaric acid, malic acid, citric acid, fumaric acid, maleic acid and benzoic acid.

Physiologically safe salts of the compounds according to the invention also include the salts of conventional bases such as preferably and for example, alkali metal salts (e.g., sodium and potassium salts), alkaline earth salts (e.g., calcium and magnesium salts) and ammonium salts derived from ammonia or organic amines with 1 to 16 carbon atoms, such as preferably and for example, ethylamine, diethylamine, triethylamine, N,N-diisopropylethyl amine, monoethanolamine, diethanolamine, triethanolamine, dimethylaminoethanol, diethylaminoethanol, procaine, dicyclohexylamine, dibenzyl-amine, N-methylpiperidine, N-methylmorpholine, arginine, lysine and 1,2-ethylene-diamine.

Within the scope of the invention, solvates refer to forms of the compounds according to the invention which form a complex in a solid or liquid state by coordination with solvent molecules. Hydrates are a special form of solvates in which molecules are coordinated with water. Hydrates are the preferred solvates within the scope of the present invention.

Furthermore, the present invention also includes prodrugs of the compounds according to the invention. The term "prodrugs" here refers to compounds which may be biologically active or inactive themselves but are converted (e.g., metabolically or hydrolytically) to the compounds according to the invention during their dwell time in the body.

Within the scope of the present invention, the substituents have the following meanings, unless otherwise specified:

($C_1$-$C_4$)-Alkyl within the scope of the invention stands for a linear or branched alkyl radical with 1 to 4 carbon atoms. The following can be mentioned, preferably and for example: methyl, ethyl, n-propyl, isopropyl, n-butyl, isobutyl, sec-butyl and tert-butyl.

($C_1$-$C_{12}$)-Alkanediyl, ($C_1$-$C_8$)-alkanediyl and ($C_1$-$C_6$)-alkanediyl, within the scope of the invention, stand for a linear α,ω-divalent alkyl radical having 1 to 12, 1 to 8 or 1 to 6 carbon atoms. A linear alkanediyl group having 1 to 8, especially preferably 1 to 6 carbon atoms is preferred. The following can be mentioned preferably and for example: methylene, ethane-1,2-diyl (1,2-ethylene), propane-1,3-diyl (1,3-propylene), butane-1,4-diyl (1,4-butylene), pentane-1,5-diyl (1,5-pentylene), hexane-1,6-diyl (1,6-hexylene), heptane-1,7-diyl (1,7-hexylene), octane-1,8-diyl (1,8-octylene), nonane-1,9-diyl (1,9-nonylene), decane-1,10-diyl (1,10-decylene), undecane-1,11-diyl (1,11-undecylene) and dodecane-1,12-diyl (1,12-dodecylene).

($C_1$-$C_4$)-Alkanediyl, within the scope of the invention, stands for a linear α,ω-divalent alkyl radical having 1 to 4 carbon atoms. Preferred examples include: methylene, ethane-1,2-diyl (1,2-ethylene), propane-1,3-diyl (1,3-propylene) and butane-1,4-diyl (1,4-butylene).

($C_2$-$C_4$)-Alkenediyl, within the scope of the invention, stands for a linear α,ω-divalent alkenyl radical having 2 to 4 carbon atoms and a double bond. Preferred examples include:

ethene-1,2-diyl, propene-1,3-diyl, but-1-ene-1,4-diyl and but-2-ene-1,4-diyl. The double bond here may be in a cis- or trans-configuration.

($C_1$-$C_{12}$)-Alkoxy, within the scope of the invention, stands for a linear or branched alkoxy radical having 1 to 4 carbon atoms. Preferred examples include: methoxy, ethoxy, n-propoxy, isopropoxy, n-butoxy and tert-butoxy.

($C_1$-$C_4$)-Alkoxycarbonyl, within the scope of the invention, stands for a linear or branched alkoxy radical having 1 to 4 carbon atoms, linked to the oxygen atom via a carbonyl group [—C(═O)—]. Preferred examples include: methoxycarbonyl, ethoxycarbonyl, n-propoxycarbonyl, isopropoxycarbonyl, n-butoxycarbonyl and tert-butoxycarbonyl.

($C_3$-$C_6$)-Cycloalkyl, within the scope of the invention, stands for a monocyclic, saturated cycloalkyl group having 3 to 6 carbon atoms. Preferred examples include: cyclopropyl, cyclobutyl, cyclopentyl and cyclohexyl.

A 5-membered heteroaryl in the definition of the ring Het, stands for a divalent aromatic heterocycle (heteroaromatic) having a total of five ring atoms, containing up to three ring heteroatoms, which may be the same or different, from the series of N, O and/or S, and linked via two ring carbon atoms or optionally one ring nitrogen atom and one ring carbon atom. Examples include: furyl, pyrrolyl, thienyl, pyrazolyl, imidazolyl, 1,2-oxazolyl, 1,3-oxazolyl, 1,2-thiazolyl, 1,3-thiazolyl, 1,2,3-triazolyl, 1,2,4-triazolyl, 1,2,4-oxadiazolyl, 1,3,4-oxadiazolyl, 1,2,4-thiadiazolyl and 1,3,4-thiadiazolyl. A 5-membered heteroaryl having two or three heteroatoms, which may be the same or different, from the series of N, O and/or S, such as in particular pyrazolyl, imidazolyl, 1,3-oxazolyl, 1,3-thiazolyl, 1,2,4-triazolyl, 1,2,4-oxadiazolyl and 1,3,4-oxadiazolyl.

Within the scope of the present invention, it is true that for all radicals that occur several times, their meanings are independent of one another. If radicals are substituted in the compounds according to the invention, then the radicals may be substituted one or more times, unless otherwise specified. Substitution with one or two substituents that are the same or different is preferred. Substitution with one substituent is especially preferred.

Preferred within the scope of the present invention are compounds of formula (I) in which:
L stands for linear ($C_1$-$C_8$)-alkanediyl, in which (a) two carbon atoms in 1,3- or 1,4-relation to one another may be bridged by including one or two of the carbon atoms between them to form a phenyl ring, or (b) up to two $CH_2$ groups not vicinal to one another may be replaced by —O—,
and
T stands for a group of the formula

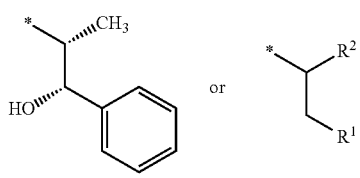

wherein
* denotes the linkage site to the nitrogen atom,
$R^1$ denotes phenyl or 1H-indol-3-yl,
and
$R^2$ denotes hydrogen or a group of the formula

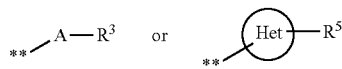

wherein
** denotes the linkage site to the radical of the respective group T,
A denotes ethene-1,2-diyl or propene-1,3-diyl,
$R^3$ stands for phenyl, which may be substituted with ($C_1$-$C_4$)-alkoxycarbonyl or carboxyl,
Het is a divalent 5-membered heteroaryl ring selected from the series of pyrazolyl, imidazolyl, 1,3-oxazolyl, 1,3-thiazolyl, 1,2,4-oxadiazolyl and 1,3,4-oxadiazolyl,
and
$R^5$ denotes a phenyl, which may be substituted with ($C_1$-$C_4$)-alkoxycarbonyl or carboxyl,
as well as their salts and solvates and the solvates of the salts.

Especially preferred within the scope of the present invention are compounds of formula (I) in which:
L stands for linear ($C_1$-$C_6$)-alkanediyl,
and
T stands for a group of the formula

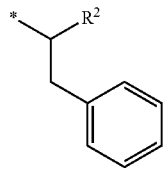

wherein
* denotes the linkage site to the nitrogen atom,
and
$R^2$ denotes hydrogen or a group of the formula

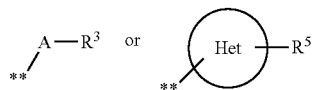

wherein
** denotes the linkage site to the radical of the respective group T,
A denotes ethene-1,2-diyl,
$R^3$ denotes phenyl, which may be substituted with methoxycarbonyl or carboxyl,
Het is 1,3,4-oxadiazol-2,5-yl,
and
$R^5$ is a phenyl, which may be substituted with methoxycarbonyl or carboxyl,
as well as their salts and solvates and the solvates of the salts.

Especially important within the scope of the present invention are compounds of formula (I), in which:
L stands for propane-1,3-diyl,
as well as their salts and solvates and the solvates of the salts.

Especially important within the scope of the present invention are compounds of formula (I), in which:

T stands for a group of the formula

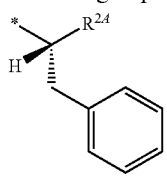

in which
* denotes the linkage site to the nitrogen atom,
and
$R^{2A}$ has the meanings of $R^2$ defined above, but does not stand for hydrogen, as well as their salts and solvates and the solvates of the salts.

The definitions of the radicals given in detail in the respective combinations and/or preferred combinations of radicals are also replaced by definitions of any radicals in other combinations, regardless of the respective combinations indicated. Most especially preferred are combinations of two or more of the preferred ranges defined above.

An additional subject matter of the present method is a method for preparing the compounds of formula (I) according to the invention, characterized in that a compound of formula (II)

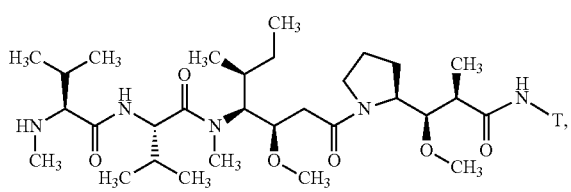

(II)

in which T has the meanings given above,
is reacted in an inert solvent, either

[A] by base-induced alkylation with a compound of formula (III)

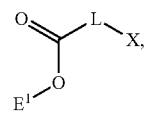

(III)

in which L has the meaning given above,
$E^1$ stands for hydrogen, $(C_1-C_4)$-alkyl or benzyl,
and
X stands for a leaving group, such as chloride, bromide, iodide, mesylate, triflate or tosylate,
to form a compound of formula (IV)

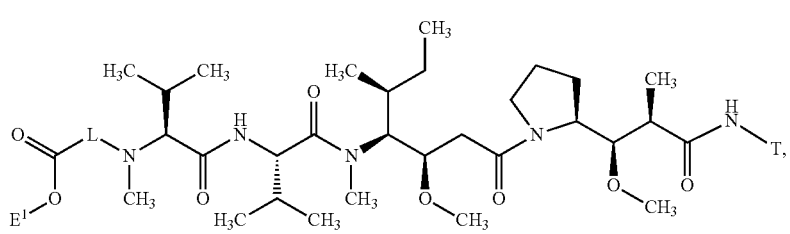

(IV)

in which $E^1$, L and T have the meanings given above,
and then in the case when $E^1$ stands for $(C_1-C_4)$-alkyl or benzyl, this ester radical is split off by conventional methods, so that, just as in the case when $E^1$ in formula (III) stands for hydrogen, the carboxylic acid of formula (I)

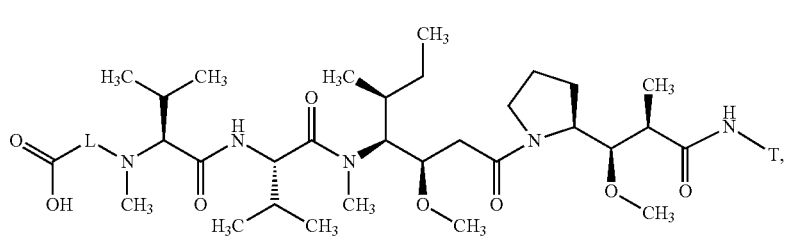

(I)

in which L and T have the meanings given above,
is obtained,
or
[B] by reacting with a compound of formula (V)

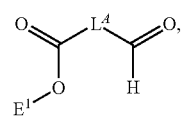

(V)

$E^1$ stands for hydrogen, $(C_1-C_4)$-alkyl or benzyl,
and
$L^A$ has the meaning of L given above, but is shortened by one $CH_2$ unit in the alkyl chain length,
in the presence of a suitable reducing agent is converted to a compound of formula (VI)

(VI)

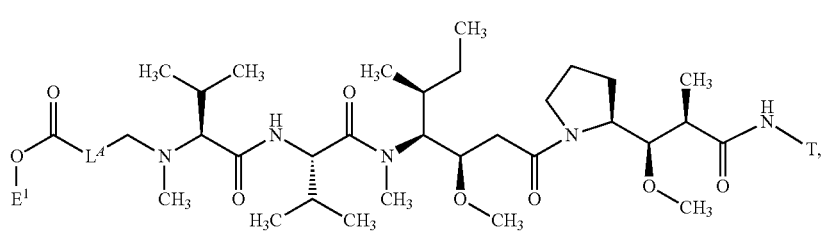

in which $E^1$, $L^A$ and T have the meanings given above, and then in the case when $E^1$ stands for $(C_1-C_4)$-alkyl or benzyl, this ester radical is split off by conventional methods, so that, just as in the case when $E^1$ in formula (V) stands for hydrogen, the carboxylic acid of formula (I-A)

(I-A)

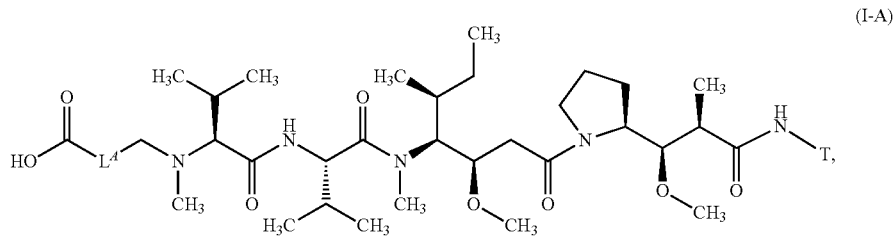

in which $L^A$ and T have the meanings given above, is obtained,
and the resulting compounds of formulas (I) and/or (I-A) are optionally separated into their enantiomers and/or diastereomers and/or reacted with the corresponding (i) solvents and/or (ii) bases or acids to form their solvates, salts and/or solvates of the salts.

Examples of suitable inert solvents for the reaction of (II)+(III)→(IV) include ethers such as diethyl ether, diisopropyl ether, methyl-tert-butylmethyl ether, tetrahydrofuran, 1,4-dioxane, 1,2-dimethoxyethane or bis-(2-methoxyethyl) ether, hydrocarbons such as benzene, toluene, xylene, pentane, hexane, heptane, cyclohexane or petroleum fractions or dipolar aprotic solvents such as acetone, methyl ethyl ketone, acetonitrile, dimethyl sulfoxide (DMSO), N,N-dimethylformamide (DMF), N,N-dimethylacetamide (DMA), N,N'-dimethylpropylene urea (DMPU), N-methylpyrrolidinone (NMP) or pyridine. It is also possible to use mixtures of such solvents. Acetone or N,N-dimethylformamide is preferred.

Suitable bases for these alkylation reactions include in particular alkali hydroxides, such as lithium hydroxide, sodium hydroxide or potassium hydroxide, alkali carbonates or alkaline earth carbonates, such as lithium carbonate, sodium carbonate, potassium carbonate, calcium carbonate or cesium carbonate or the usual organic amines such as triethylamine, N-methylmorpholine, N-methylpiperidine, N,N-diisopropylethylamine, pyridine or 4-N,N-dimethylaminopyridine. Potassium or cesium carbonate is preferably used. It is optionally advantageous to add an alkylating catalyst, such as lithium bromide or iodide, sodium or potassium iodide, tetra-n-butylammonium bromide or iodide or benzyltriethylammonium bromide, for example.

The reaction (II)+(III)→(IV) is generally carried out in a temperature range from −20° C. to +100° C., preferably at 0° C. to +50° C. The reaction may take place at normal, elevated or reduced pressure (e.g., from 0.5 bar to 5 bar). It is usually carried out under normal pressure.

The reaction (II)+(V)→(VI) takes place in solvents that are inert under the reaction conditions and are typically used for reductive amination, optionally in the presence of an acid and/or a water-withdrawing agent as the catalyst. Such solvents include, for example, alcohols such as methanol, ethanol, n-propanol, isopropanol, n-butanol or tert-butanol, ethers such as tetrahydrofuran, 1,4-dioxane, 1,2-dimethoxyethane or bis-(2-methoxyethyl)ether or other solvents such as dichloromethane, 1,2-dichloroethane, N,N-dimethylformamide or even water. Likewise, it is possible to use mixtures of these solvents. The preferred solvent for use here is a 1,4-dioxane/water mixture to which acetic acid or dilute hydrochloric acid is added as a catalyst.

Suitable reducing agents for this reaction include in particular complex borohydrides, such as sodium borohydride, sodium cyanoborohydride, sodium triacetoxyborohydride or tetra-n-butylammonium borohydride. Sodium cyanoborohydride is preferred.

The reaction (II)+(V)→(VI) is generally carried out in a temperature range from 0° C. to +120° C., preferably at +50° C. to +100° C. The reaction may take place at normal, elevated or reduced pressure (e.g., from 0.5 bar to 5 bar). It is usually carried out under normal pressure.

An ester radical $E^1$ is split off by the usual methods in the process steps (IV)→(I) and (VI) [$E^1$=$(C_1-C_4)$-alkyl or benzyl] according to the usual methods by treating the ester with an acid or a base in an inert solvent, whereby in the last variant, the carboxylate salt obtained first is converted to the free carboxylic acid by subsequent addition of an acid. In the case of a tert-butyl ester, the cleavage is preferably performed by using an acid. In the case of a benzyl ester, the cleavage may also take place by hydrogenolysis in the presence of a suitable palladium catalyst, such as palladium on activated carbon, for example.

The ester radical $E^1$ originating from compound (III) and/or (V) is selected here so that the conditions of its cleavage are compatible with the respective group T in compounds (IV) and (VI).

The usual inorganic bases are suitable as the bases for ester hydrolysis. These include in particular alkali hydroxides or alkaline earth hydroxides such as lithium, sodium, potassium or barium hydroxide, or alkali carbonates or alkaline earth carbonates such as sodium, potassium or calcium carbonates. Lithium, sodium or potassium hydroxide is preferred.

Suitable acids for the ester cleavage reaction include in general sulfuric acid, hydrochloric acid/hydrogen chloride, hydrobromic acid/hydrogen bromide, phosphoric acid, acetic acid, trifluoroacetic acid, toluenesulfonic acid, methanesulfonic acid or trifluoromethanesulfonic acid or mixtures thereof, optionally with the addition of water. Hydrochloric acid or trifluoroacetic acid are preferred in the case of a tert-butyl ester and hydrochloric acid is preferred in the case of a methyl ester.

Suitable inert solvents for these reactions include water or the organic solvents typically used for ester cleavage. These preferably include low alcohols such as methanol, ethanol, n-propanol or isopropanol, ethers such as diethyl ether, tetrahydrofuran, 1,4-dioxane or 1,2-dimethoxyethane, or other solvents such as dichloromethane, acetone, methyl ethyl ketone, N,N-dimethylformamide or dimethyl sulfoxide. It is also possible to use mixtures of these solvents. In the case of a basic ester hydrolysis, mixtures of water with 1,4-dioxane, tetrahydrofuran, methanol, ethanol and/or dimethylformamide are preferred for use here. In the case of the reaction with trifluoroacetic acid, dichloromethane is preferred, and in the case of the reaction with hydrochloric acid, tetrahydrofuran, diethyl ether, 1,4-dioxane or water is preferred.

The ester cleavage generally takes place in a temperature range of −20° C. to +100° C., preferably at 0° C. to +50° C.

The compounds of formula (II) can be synthesized by the usual methods of peptide chemistry by coupling a compound of formula (VII)

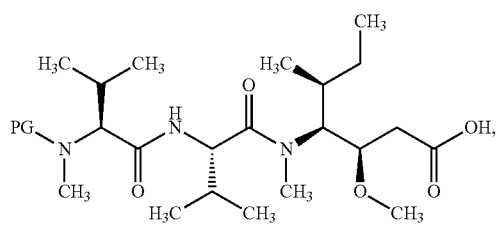

(VII)

in which
PG stands for an amino protective group such as (9H-fluoren-9-ylmethoxy)carbonyl, tert-butoxycarbonyl or benzyloxycarbonyl,
in an inert solvent with activation of the carboxyl function in (VII), either
[C] first with a compound of formula (VIII)

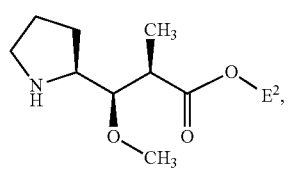

(VIII)

in which
$E^2$ stands for hydrogen, $(C_1-C_4)$-alkyl or benzyl,
or a salt of this compound to form a compound of formula (IX)

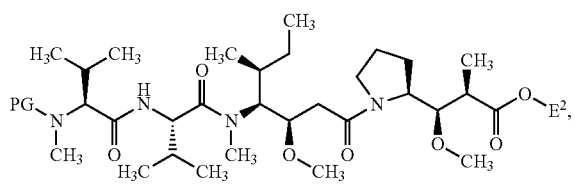

(IX)

in which $E^2$ and PG have the meanings given above,
then in the event that $E^2$ stands for $(C_1-C_4)$-alkyl or benzyl, this ester radical is split off by the usual methods and the resulting carboxylic acid of formula (X)

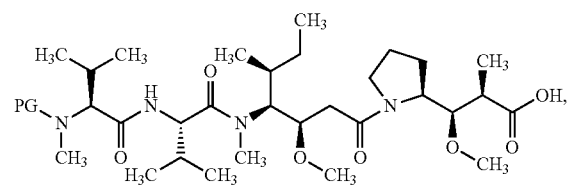

(X)

in which PG has the meaning given above,
then in an inert solvent with activation of the carboxyl function with a compound of formula (XI):

 (XI), in which T has the meanings given above,
or with a salt of this compound to form a compound of formula (XII)

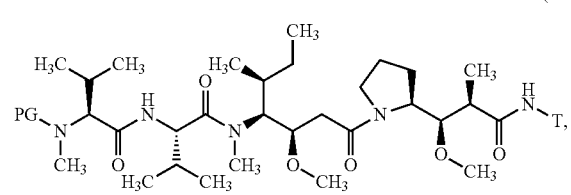

(XII)

in which PG and T have the meanings given above,
or
[D] with a compound of formula (XIII)

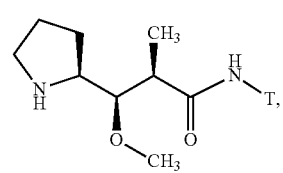

(XIII)

in which T has the meanings given above,
or with a salt of this compound, likewise to form the compound of formula (XII)

(XII)

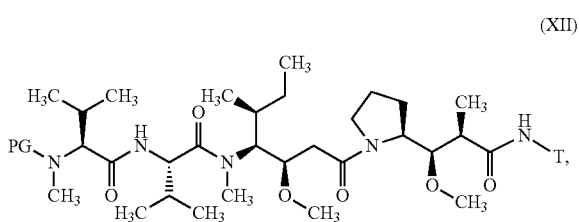

in which PG and T have the meanings given above, and the compound of formula (XII) is then deprotected in the usual way to form a compound of formula (II)

(II)

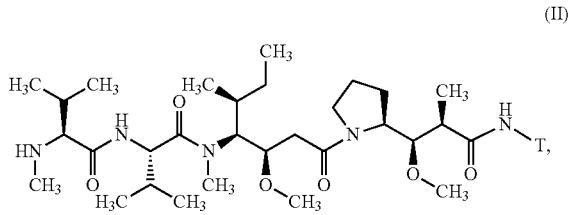

in which T has the meanings given above.

The coupling reactions described above (formation of amide from the respective amine and carboxylic acid components) are performed according to the standard methods of peptide chemistry (see, for example, M. Bodanszky, *Principles of Peptide Synthesis*, Springer Verlag, Berlin, 1993; M. Bodanszky and A. Bodanszky, *The Practice of Peptide Synthesis*, Springer Verlag, Berlin, 1984; H. D. Jakubke and H. Jeschkeit, *Aminosäuren, Peptide, Proteine [Amino Acids, Peptides, Proteins]*, Verlag Chemie, Weinheim, 1982).

Inert solvents for these coupling reactions (VII)+(VIII)→(IX), (X)+(XI)→(XII) and (VII), (XIII)→(XII) include, for example, ethers such as diethyl ether, diisopropyl ether, tert-butylmethyl ether, tetrahydrofuran, 1,4-dioxane, 1,2-dimethoxyethane or bis-(2-methoxyethyl)ether, hydrocarbons such as benzene, toluene, xylene, pentane, hexane, heptane, cyclohexane or petroleum fractions, halohydrocarbons such as dichloromethane, trichloromethane, tetrachloromethane, 1,2-dichloroethane, trichloroethylene or chlorobenzene or dipolar aprotic solvents such as acetone, methyl ethyl ketone, acetonitrile, ethyl acetate, pyridine, dimethyl sulfoxide (DMSO), N,N-dimethylformamide (DMF), N,N-dimethylacetamide (DMA), N,N'-dimethylpropylene urea (DMPU) or N-methylpyrrolidinone (NMP). It is also possible to use mixtures of such solvents. N,N-Dimethylformamide is preferred.

Suitable activation/condensation agents for these coupling reactions include, for example, carbodiimides such as N,N'-diethyl, N,N'-dipropyl, N,N'-diisopropyl, N,N'-dicyclohexylcarbodiimide (DCC) or N-(3-dimethylaminoisopropyl)-N'-ethylcarbodiimide hydrochloride (EDC), phosgene derivatives such as N,N'-carbonyldiimidazole (CDI) or isobutyl chloroformate, 1,2-oxazolium compounds such as 2-ethyl-5-phenyl-1,2-oxazolium 3-sulfate or 2-tert-butyl-5-methylisoxazolium perchlorate, acylamino compounds, such as 2-ethoxy-1-ethoxycarbonyl-1,2-dihydroquinoline, α-chlorenamines such as 1-chloror-2-methyl-1-dimethylamino-1-propene, phosphorus compounds such as propane phosphonic acid anhydride, cyanophosphonic acid diethyl ester, bis-(2-oxo-3-oxazolidinyl)phosphoryl chloride, benzotriazol-1-yloxy-tris-(dimethylamino)phosphonium hexafluorophosphate or benzotriazol-1-yloxy-tris-(pyrrolidino)phosphonium hexafluorophosphate (PyBOP), or uronium compounds such as O-(benzotriazol-1-yl)-N,N,N',N'-tetramethyluronium tetrafluoroborate (TBTU), O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU), O-(7-azabenzotriazol-1-yl)-1,1,3,3-tetramethyluronium hexafluorophosphate (HATU) or O-(1H-6-chlorobenzotriazol-1-yl)-1,1,3,3-tetramethyluronium tetrafluoroborate (TCTU), optionally in combination with additional excipients, such as 1-hydroxybenzotriazole (HOBt) or N-hydroxysuccinimide (HOSu) as well as bases, such as alkali carbonates, e.g., sodium or potassium carbonate or tertiary amine bases, such as triethylamine, N-methylmorpholine, N-methylpiperidine, N,N-diisopropylethylamine, pyridine or 4-N,N-dimethylaminopyridine.

Within the context of the present invention, the preferred activation/condensation agents for such coupling reactions include N-(3-dimethylaminoisopropyl)-N'-ethylcarbodiimide hydrochloride (EDC) in combination with 1-hydroxybenzotriazole (HOBt) and N,N-diisopropylethylamine or O-(7-azabenzotriazol-1-yl)-N,N,N',N'-tetramethyluronium hexafluorophosphate (HATU), likewise in combination with N,N-diisopropylethylamine.

The coupling reactions (VII)+(VIII)→(IX), (X)+(XI)→(XII) and (VII)+(XIII)→(XII) are usually performed in a temperature range from −20° C. to +60° C., preferably at 0° C. to +40° C. The reactions may be performed under normal, elevated or reduced pressure (e.g., from 0.5 to 5 bar). It is customary to work under normal pressure.

The functional groups optionally present in the compounds—such as amino, hydroxyl and carboxyl groups in particular—may also, if expedient or necessary, be present in a temporarily protected form in the process steps described above. Such protective groups are introduced and removed according to the standard methods of peptide chemistry (see, for example, T. W. Greene and P. G. M. Wuts, *Protective Groups in Organic Synthesis*, Wiley, New York, 1999; M. Bodanszky and A. Bodanszky, *The Practice of Peptide Synthesis*, Springer Verlag, Berlin, 1984). In the presence of several protected groups, they may optionally be released again simultaneously in either a one-pot reaction or in separate reaction steps.

The preferred amino protective group is tert-butoxycarbonyl (Boc), benzyloxycarbonyl (Z) or (9H-fluoren-9-ylmethoxy)carbonyl (Fmoc); tert-butyl or benzyl is preferably used as the protective group $PG^2$ for a hydroxyl or carboxyl function. A tert-butyl or tert-butoxycarbonyl group is usually split off by treating it with a strong acid such as hydrochloric acid, hydrobromic acid or trifluoroacetic acid in an inert solvent such as diethyl ether, 1,4-dioxane, dichloromethane or acetic acid. This reaction may optionally also be performed without adding an inert solvent. In the case of benzyl or benzyloxycarbonyl as the protective group, such a protective group is preferably removed by hydrogenolysis in the presence of a suitable palladium catalyst, such as palladium on activated carbon, for example. The (9H-fluoren-9-ylmethoxy)carbonyl group is generally split off with the help of a secondary amine base, such as diethylamine or piperidine.

An ester radical $E^2$ in compound (VIII) [$E^2$=($C_1$-$C_4$)-alkyl or benzyl] here is selected so that the conditions of its being split off are compatible with the respective protective group PG from compound (VII).

The compounds of formula (VII) can be synthesized by a similar method, for example, by first coupling N-(benzyloxycarbonyl)-L-valine of formula (XIV)

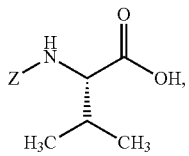

(XIV)

in which Z stands for the benzyloxycarbonyl protective group, with a compound of formula (XV) with the help of a condensation agent:

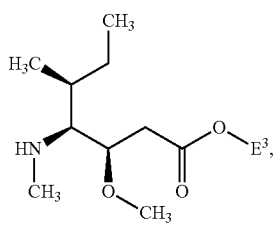

(XV)

in which $E^3$ stands for $(C_1\text{-}C_4)$-alkyl, or with a salt of this compound to form a compound of formula (XVI)

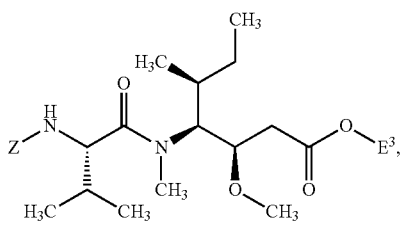

(XVI)

in which $E^3$ and Z have the meanings given above, then, after hydrogenolytic removal of the Z-protective group, this compound is then coupled with N-protected N-methyl-L-valine of the formula (XVII) in the presence of a condensation agent:

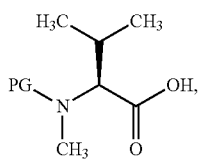

(XVII)

in which

PG stands for an amino protective group, such as (9H-fluoren-9-ylmethoxy)carbonyl, tert-butoxycarbonyl or benzyloxycarbonyl, to form a compound of the formula (XVIII)

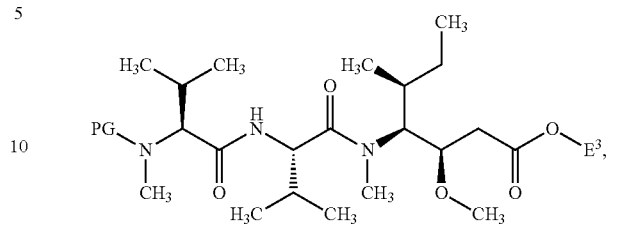

(XVIII)

in which $E^3$ and PG have the meanings given above, and then the ester group $-C(O)O\text{-}E^3$ in (XVIII) is reacted by the usual methods to form the free carboxylic acid (VII).

The coupling reactions (XIV)+(XV)→(XVI) and Z-deprotected (XVI)+(XVII)→(XVIII) are performed under reaction conditions similar to those described above for the coupling steps shown in methods [C] and [D].

The ester group $-C(O)O\text{-}E^3$ is hydrolyzed in reaction step (XVIII)→(VII) in a process similar to that described above as part of the process sequences [A] and [B] for the ester radical $E^1$. The alkyl group $E^3$ in compound (XV) is selected here so that the conditions of their cleavage are compatible with the respective protective group PG from compound (XVII).

The compounds of formula (XIII) are in turn accessible by coupling the compound (XI) described above with the compound (XIX):

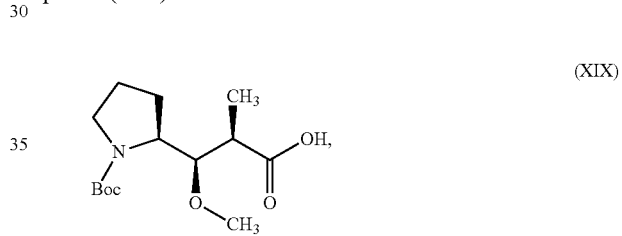

(XIX)

in which Boc stands for the tert-butoxycarbonyl protective group, to yield a compound of formula (XX)

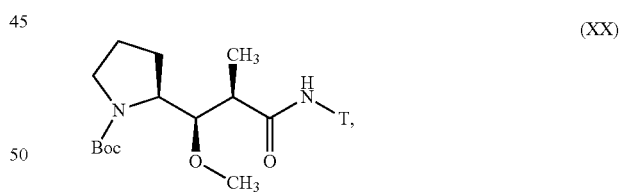

(XX)

in which Boc and T have the meanings given above, and then splitting off the Boc protective group.

The coupling reaction (XI)+(XIX)→(XX) is in turn performed under similar conditions like those described above for the coupling steps in methods [C] and [D].

The compounds of formulas (III), (V), (VIII), (XI), (XIV), (XV), (XVII) and (XIX), including chiral or diastereomeric forms thereof, if applicable, are available commercially or have been described as such in the literature or they can be synthesized by methods like those published in the literature in a manner that would be self-evident for those skilled in the art. Numerous detailed publications and specifications in the literature concerning the synthesis of the starting materials can also be found in the Experimental Part in the section on the synthesis of the starting compounds and intermediates.

If corresponding isomer-pure starting materials are not available, then the compounds according to the invention can expediently be separated into the corresponding enantiomers and/or diastereomers already at the stage of the compounds (II), (IV), (VI), (XI), (XII), (XIII) and (XX), which are then reacted further in isolated form according to the reaction steps described above. Such a separation of the stereoisomers can be performed according to the usual methods familiar to those skilled in the art. Chromatographic methods on chiral and/or achiral separation phases are preferably used. In the case of free carboxylic acids as the intermediates, separation via diastereomeric salts with the help of chiral bases may also be performed as an alternative.

Synthesis of the compounds according to the invention can be illustrated by the following reaction schemes as an example:

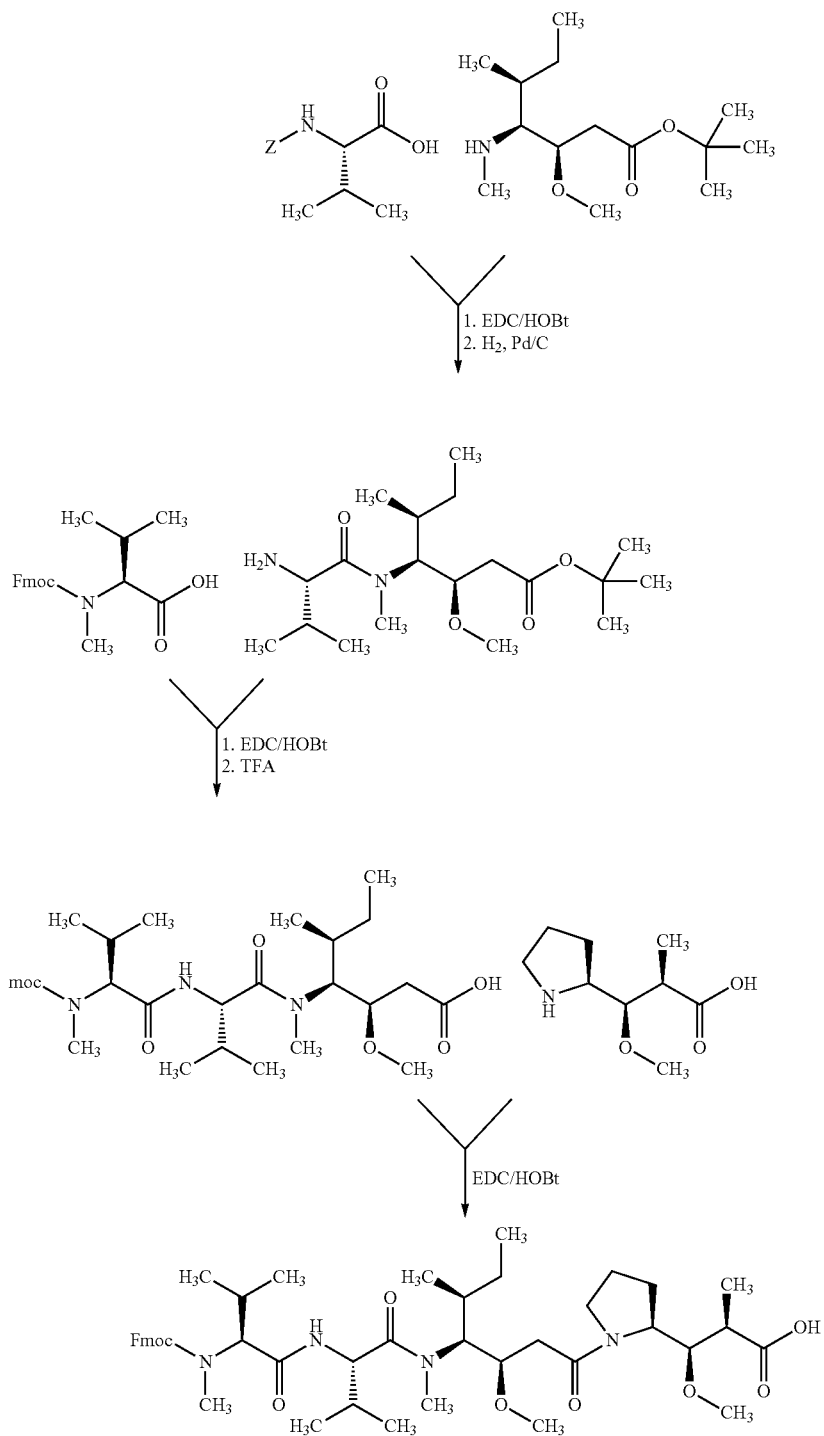

Scheme 1

Scheme 2
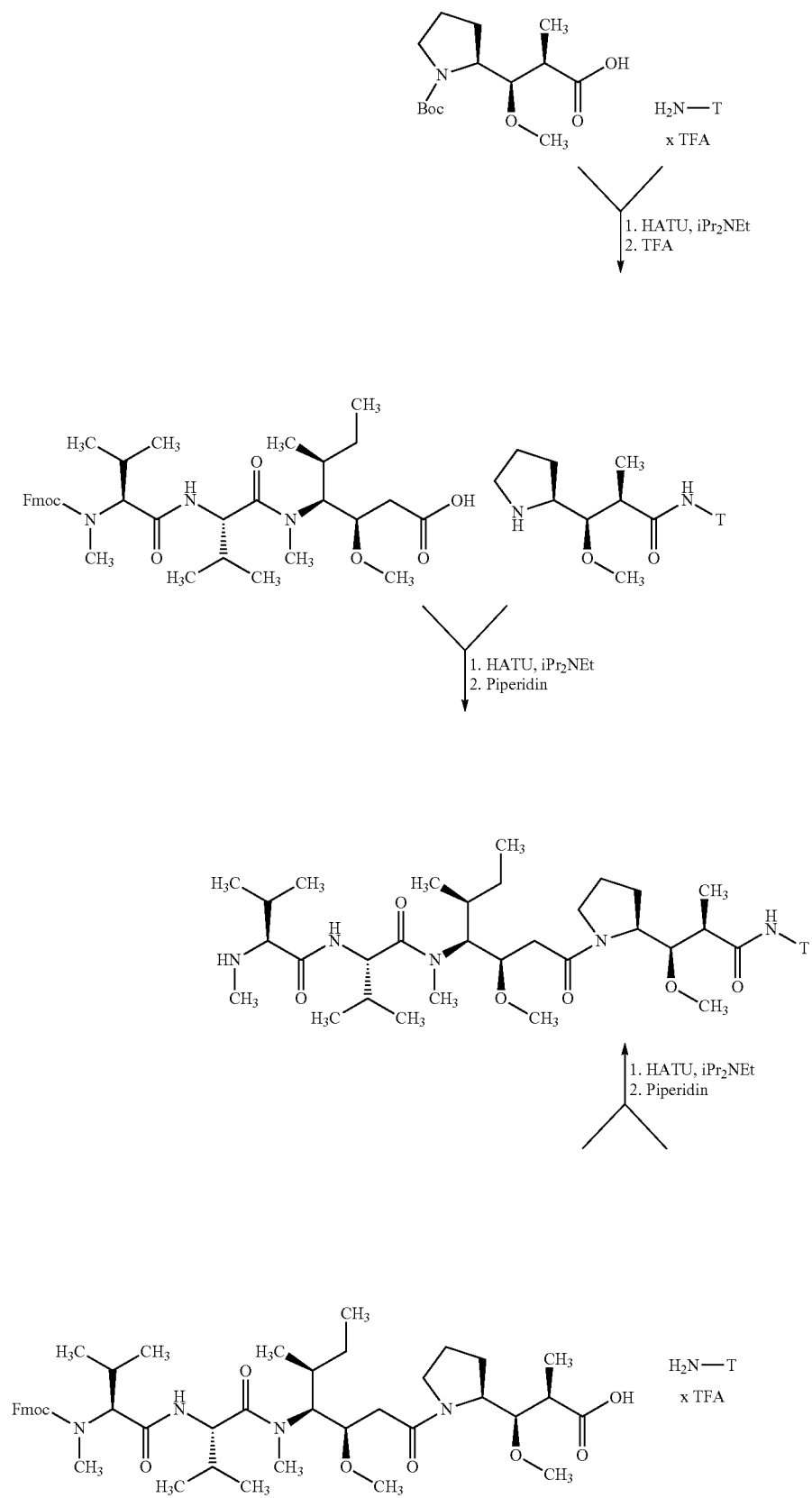

Scheme 3
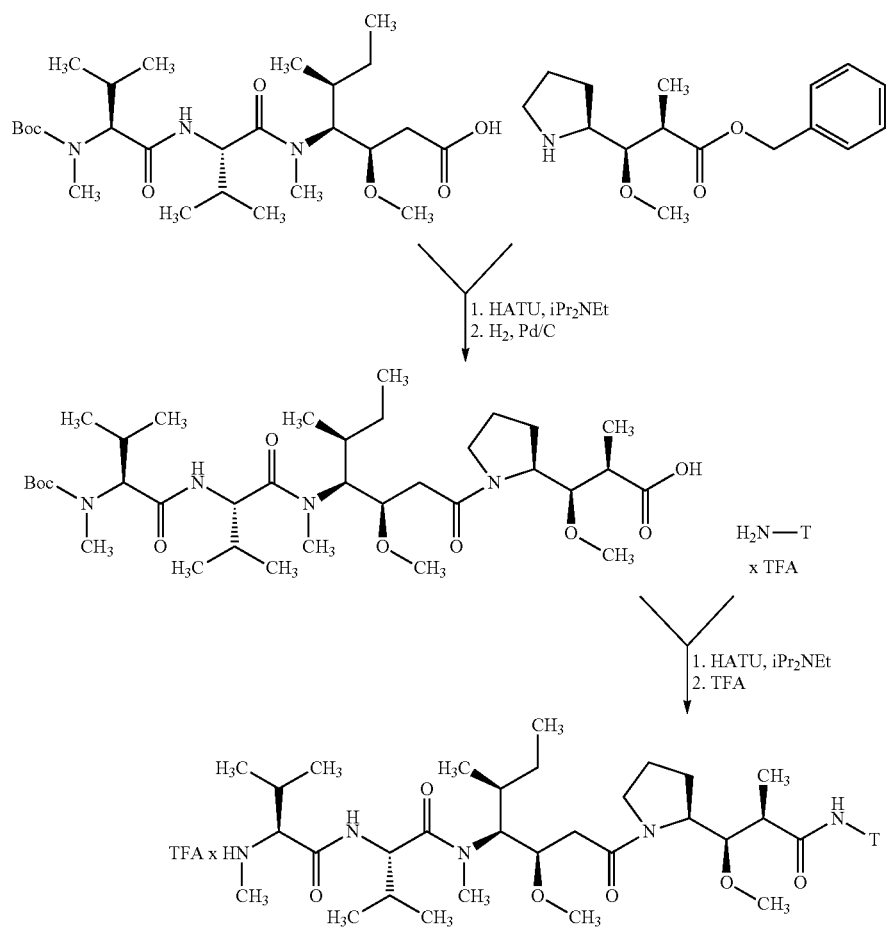
Scheme 4
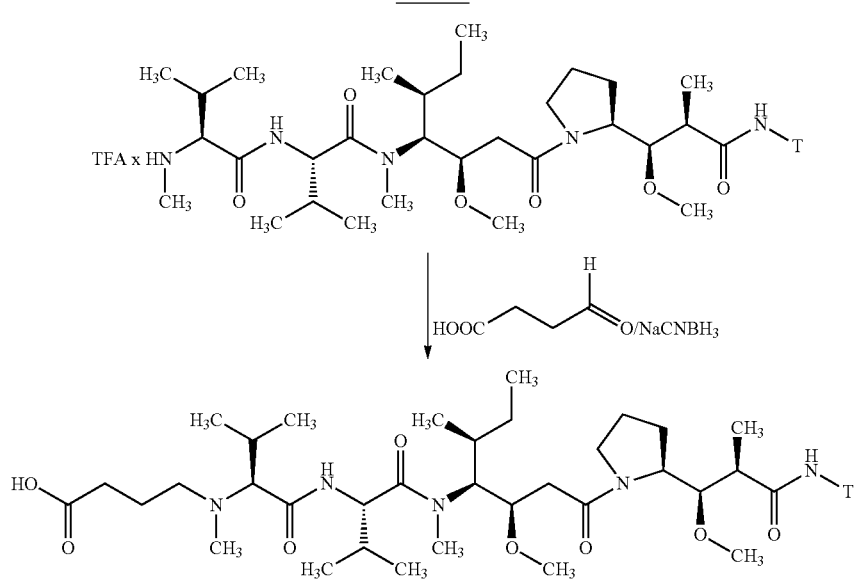

These compounds have valuable pharmacological properties and can be used for preventing and treating diseases humans and animals.

In comparison with other auristatin derivatives known from the prior art, the N-terminal carboxyalkyl group [HOOC-L- in formula (I)] present in the compounds according to the present invention does not have the mere function of a linker for the potential linkage to antibody proteins or other ligands, but instead is a constituent structural element for the surprisingly advantageous profile of properties of these compounds.

These compounds according to the invention have a stronger cytotoxic activity in comparison with monomethylauristatin F (MMAF), for example, or have a reduced potential, while at the same time also being substrates for cellular transporter proteins.

The compounds according to the invention are therefore particularly suitable for treatment of hyperproliferative diseases in humans and mammals in general. These compounds can on the one hand inhibit, block, reduce or restrict cell proliferation and cell division while increasing apoptosis on the other hand.

The hyperproliferative diseases for treatment of which the compounds according to the invention may be used include in particular the group of cancers and tumor diseases. These are understood to include in particular the following diseases within the scope of the present invention without being limited to these: breast cancer and breast tumors (ductile and lobular forms, also in situ), respiratory tract tumors (small cell and non-small-cell carcinomas, bronchial carcinoma), brain tumors (e.g., of the brain stem and the hypothalamus, astrocytoma, medulloblastoma, ependymoma and neuroectodermal and pineal tumors), tumors of the digestive tract (esophagus, stomach, gallbladder, small intestine, large intestine, rectum), liver tumors (including hepatocellular carcinoma, cholangiocarcinoma and mixed hepatocellular cholangiocarcinoma), tumors of the head and neck area (larynx, hypopharynx, nasopharynx, oropharynx, lips and oral cavity), skin tumors (squamous epithelial carcinoma, Kaposi's sarcoma, malignant melanoma, Merkel cell skin cancer and non-melanoma type skin cancer), tumors of the soft tissues (including soft tissue sarcomas, malignant fibrous histiocytoma, lymphosarcoma and rhabdomyosarcoma), tumors of the eyes (including intraocular melanoma and retinoblastoma), tumors of the endocrine and exocrine glands (e.g., thyroid and parathyroid glands, pancreatic gland and esophageal gland), tumors of the urinary tract (bladder, penis, kidney, renal pelvis and urethral tumors) as well as tumors of the reproductive organs (endometrium, cervical, ovarian, vaginal, vulval and uterine carcinomas in the woman and prostatic and testicular carcinomas in males). These also include proliferative blood diseases in solid form and as circulating blood cells such as lymphomas, leukemias and myeloproliferative diseases, e.g., acute myeloid leukemia, acute lymphoblastic, chronic lymphocytic leukemia, chronic myelogenous leukemia and hairy cell leukemia as well as AIDS-related lymphomas, Hodgkin's lymphomas, non-Hodgkin's lymphomas, cutaneous T-cell lymphomas, Burkitt's lymphomas and lymphomas of the central nervous system.

These human diseases, which have been characterized well, may also occur with a comparable etiology in other mammals and can also be treated with the compounds according to the present invention in those cases.

Treatment of the types of cancer mentioned above by means of the compounds according to the invention includes treatment of such tumors as well as treatment of metastatic or circulating forms thereof.

The terms "treatment" or "to treat" are used in the conventional sense within the scope of this invention and refers to the care, treatment and consultation of a patient with the goal of combatting, reducing, diminishing or ameliorating a disease or health deviation and improving the quality of life, which is impaired by this disease, such as in a cancer, for example.

An additional subject matter of the present invention thus relates to the use of the compounds according to the invention for treatment and/or prevention of diseases, in particular the diseases cited above.

An additional subject matter of the present invention is the use of the compounds according to the invention for producing a pharmaceutical drug for treatment and/or prevention of diseases, in particular the diseases cited above.

An additional subject matter of the present invention is the use of the compounds according to the invention in a method for treatment and/or prevention of diseases, in particular the diseases cited above.

An additional subject matter of the present invention is a method for treatment and/or prevention of diseases, in particular the diseases cited above, using an effective amount of at least one of the compounds according to the invention.

The compounds according to the invention may be used alone or, if necessary, in combination with one or more other pharmacologically active substances, as long as this combination does not lead to adverse effects and unacceptable side effects. Another subject matter of the present invention therefore relates to pharmaceutical drugs containing at least one of the compounds according to the invention and one or more additional active ingredients, in particular for treating and/or preventing the diseases listed above.

The compounds according to the invention may be combined with known antihyperproliferative, cytostatic or cytotoxic substances, for example, for treatment of cancer. Examples of suitable combination drugs include the following:

aldesleukin, alendronic acid, alfaferone, alitretinoin, allopurinol, aloprim, aloxi, altretamine, amino glutethimide, amifostine, amrubicin, amsacrine, anastrozol, anzmet, aranesp, arglabin, arsentrioxide, aromasine, 5-azacytidine, azathioprine, BCG or tice-BCG, bestatin, betamethasone acetate, betamethasone sodium phosphate, bexarotene, bleomycin sulfate, broxuridine, bortezomib, busulfan, calcitonin, campath, capecitabine, carboplatin, casodex, cefesone, celmoleukin, cerubidine, chlorambucil, cisplatin, cladribine, clodronic acid, cyclophosphamide, cytarabine, dacarbazine, dactinomycin, daunoxome, decadrone, decadrone phosphate, delestrogen, denileukin diftitox, depo medrol, desloreline, dexrazoxane, diethylstilbestrol, diflucan, docetaxel, doxifluridine, doxorubicin, dronabinol, DW-166HC, eligard, elitek, ellence, emend, epirubicin, epoetin alfa, epogen, eptaplatin, ergamisole, estrace, estradiol, estramustine sodium phosphate, ethinyl estradiol, ethyol, etidronic acid, etopophos, etoposide, fadrozole, farstone, filgrastim, finasteride, fligrastim, floxuridine, fluconazole, fludarabin, 5-fluorodeoxyuridine monophosphate, 5-fluorouracil (5-FU), fluoxymesterone, flutamide, formestane, fosteabine, fotemustine, fulvestrant, gammagard, gemcitabine, gemtuzumab, gleevec, gliadel, gosereline, granisetrone hydrochloride, histreline, hycamtine, hydrocortone, erythrohydroxynonyladenine, hydroxyurea, ibritumomab tiuxetan, idarubicin, ifosfamide, interferon-alpha, interferon-alpha-2, interferon-alpha-2α, interferon-alpha-2β, interferon-alpha-n1, interferon-alpha-n3, interferon-beta, interferon-gamma-1α, interleukin-2, intron A, iressa, irinotecan, kytril, lentinane sulfate, letrozole, leucovorine, leuprolide, leuprolide acetate, levamisole, levofolic acid calcium salt, levothroid, levoxyl, lomustine, lonidamine, marinol, mechlorethamine, mecobalamine, medroxyprogesterone acetate, megestrole acetate, melphalane, menest, 6-mercaptopurine, mesna, methotrexate, metvix, miltefosine, minocycline, mitomycin C, mitotane, mitoxantrone, modrenal, myocet, nedaplatin, neulasta, neumega, neupogen, nilutamide, nolvadex, NSC-631570, OCT-43, octreotide, ondansetrone hydrochloride, oraprel, oxaliplatin, paclitaxel, pediapred, pegaspargase, pegasys, pentostatin, picibanil, pilocarpine hydrochloride, pirarubicin, plicamycin, porfimer sodium, prednimustin, prednisolone, prednisone, premarin, procarbazine, procrit, raltitrexed, rebif, rhenium 186 etidronate, rituximab, roferone A, romurtide, salagen, sandostatin, sargramostim, semustine, sizofiran, sobuzoxane, solu-medrol, streptozocin, strontium-89 chloride, synthroid, tamoxifen, tamsulosine, tasonermine, tastolactone, taxoter, teceleukin, temozolomide, teniposide, testosterone propionate, testred, thioguanine, thiotepa, thyrotropin, tiludronic acid, topotecan, toremifen, tositumomab, tastuzumab, teosulfane, tre-tinoin, trexall, trimethylmelamine, trimetrexate, triptoreline acetate, triptoreline pamoate, uft, uridine, valrubicin, vesnarinone, vinblastine, vincristine, vindesine, vinorelbine, virulizine, zinecard, zinostatin stimalamer, zofran; ABI-007, acolbifene, actimmune, affinitak, aminopterine, arzoxifene, asoprisnil, atamestane, atrasentane, avastin, BAY 43-9006 (sorafenib), CCI-779, CDC-501, celebrex, cetuximab, crisnatol, cyproterone acetate, decitabin, DN-101, doxorubicin MTC, dSLIM, dutasteride, edotecarin, eflornithine, exatecane, fenretinide, histamine dihydrochloride, histreline-hydrogel implant, holmium-166-DOTMP, ibandronic acid, interferon-gamma, intron PEG, ixabepilone, keyhole limpet hemocyanine, L-651582, lanreotide, lasofoxifen, libra, lona-farnib, miproxifen, minodronate, MS-209, liposomales MTP-PE, MX-6, nafareline, nemorubicin, neovastat, nolatrexed, oblimersen, onko-TCS, osidem, paclitaxel polyglutamate, pamidronate disodium, PN-401, QS-21, quazepam, R-1549, raloxifene, ranpirnase, 13-cis-retinic acid, satraplatin, seocalcitol, T-138067, tarceva, taxoprexine, thymosine-alpha-1, tiazofurine, tipifarnib, tirapazamine, TLK-286, toremifene, transmid 107R, valspodar, vapreotide, vatalanib, verteporfin, vinflunine, Z-100, zoledronic acid as well as combinations thereof.

In a preferred embodiment, the compounds according to the present invention may be combined with antihyperproliferative agents, which may include the following, for example, although this list is not conclusive:
aminoglutethimide, L-asparaginase, azathioprine, 5-azacytidine, bleomycin, busulfan, carboplatin, carmustin, chlorambucil, cisplatin, colaspase, cyclophosphamide, cytarabine, dacarbazine, dactinomycin, daunorubicin, diethylstilbestrol, 2',2'-difluorodeoxycytidine, docetaxel, doxorubicin (adriamycin), epirubicin, epothilone and seine derivate, erythrohydroxynonyladenine, ethinyl estradiol, etoposide, fludarabine phosphate, 5-fluorodeoxyuridine, 5-fluordeoxyuridine monophosphate, 5-fluoruracil, fluoxymesterone, flutamide, hexamethyl melamine, hydroxyurea, hydroxyprogesterone caproate, idarubicin, ifosfamide, interferon, irinotecan, leucovorin, lomustine, mechlorethamine, medroxyprogesterone acetate, megestrol acetate, melphalan, 6-mercaptopurine, mesna, methotrexate, mitomycin C, mitotane, mitoxantrone, paclitaxel, pentostatin, n-phosphonoacetyl L-aspartate (PALA), plicamycin, prednisolone, prednisone, procarbazine, raloxifene, semustine, streptozocin, tamoxifen, teniposide, testosterone propionate, thioguanine, thiotepa, topotecan, trimethylmelamine, uridine, vinblastine, vincristine, vindesine and vinorelbine.

According to one very promising feature, the compounds according to the invention can also be combined with biological therapeutic agents such as antibodies (e.g., Avastin, Rituxan, Erbitux, Herceptin). The compounds according to the invention may also achieve positive effects in combination with treatments directed against angiogenesis, for example, with Avastin, axitinib, recentin, regorafenib, sorafenib or sunitinib. Combinations with inhibitors of the proteasome and of mTOR as well as combinations with antihormones and steroidal metabolic enzyme inhibitors are also especially suitable because of their favorable profile of side effects.

In general, the following goals can be pursued with the combination of compounds of the present invention with other active cytostatic or cytotoxic agents:
improved efficacy in retarding the growth of a tumor, reducing its size or even completely eliminating it in comparison with treatment with a single drug;
the possibility of using the chemotherapeutic drugs in a lower dose than in monotherapy;
the possibility of a tolerable therapy with few adverse effects in comparison with a single dose;
the possibility of treatment of a broader spectrum of tumors;
achieving a higher response rate to the treatment;
longer survival time for patients in comparison with today's standard therapy.

In addition, the compounds according to the invention may also be used in combination with radiation therapy and/or a surgical intervention.

Another subject matter of the present invention relates to pharmaceutical drugs containing at least one compound according to the invention, usually together with one or more inert, non-toxic, pharmaceutically suitable excipients as well as their use for the purposes indicated above.

The compounds according to the invention may can systemically and/or topically. To this end, they are administered by a suitable route, for example, by an oral, parenteral, pulmonary, nasal, sublingual, lingual, buccal, rectal, transdermal, conjunctival or otic route or as an implant and/or a stent.

For these methods of administration, the compounds according to the invention may be administered in suitable dosage forms.

For oral administration, the suitable dosage forms that function according to the state of the art and deliver the compounds according to the invention rapidly and/or in a modified form contain the compounds according to the invention in a crystalline and/or amorphized and/or dissolved form, e.g., tablets (coated or uncoated tablets, for example, with enteric coatings or insoluble coatings or those with a delayed release that control the release of the compound according to the invention), tablets or films/oblates that disintegrate rapidly in the mouth, films/lyophilisates, capsules (for example, hard or soft gelatin capsules), coated pills, granules, pellets, powders, emulsions, suspensions, aerosols or solutions.

Parenteral administration may be used to bypass a resorption step (e.g., intravenous, intra-arterial, intracardiac, intraspinal or intralumbar) or with the inclusion of resorption (e.g., intramuscular, subcutaneous, intracutaneous, percutaneous or intraperitoneal). Suitable dosage forms for parenteral administration include infusion and injection preparations in the form of solutions, suspensions, emulsions, lyophilisates or sterile powders.

For the other routes of administration, it is suitable to use inhalation dosage forms (including powder inhalers, nebulizers), nose drops, solutions or sprays, tablets to be administered lingually, sublingually or buccally, films, oblates or capsules, suppositories, ear or eye preparations, vaginal suppositories, aqueous suspensions (lotions, shake mixtures), lipophilic suspensions, ointments, creams, transdermal therapeutic systems (e.g., patches), milks, pastes, foams, dusting powders, implants or stents.

Oral or parenteral administration is preferred, in particular oral and intravenous administration.

The compounds according to the invention may be converted to the dosage forms indicated. This may be done in a known way by mixing with inert, non-toxic, pharmaceutically suitable excipients. These excipients include, among others, vehicles (for example, microcrystalline cellulose, lactose, mannitol), solvents (e.g., liquid polyethylene glycols), emulsifiers and dispersants or wetting agents (for example, sodium dodecyl sulfate, polyoxysorbitan oleate), binders (for example, polyvinyl pyrrolidone), synthetic and natural polymers (for example, albumin), stabilizers (e.g., antioxidants such as ascorbic acid), coloring agents (e.g., inorganic pigments such as iron oxides, for example) and taste and/or odor correcting substances).

For parenteral administration in general, it has proven advantageous to administer doses of approx. 0.001 to 1 mg/kg, preferably approx. 0.01 to 0.5 mg/kg body weight to achieve effective results. In oral administration, the dose is approx. 0.01 to 100 mg/kg, preferably approx. 0.01 to 20 mg/kg and most especially preferably 0.1 to 10 mg/kg body weight.

Nevertheless, it may optionally be necessary to deviate from the stated amounts, namely depending on body weight, route of administration, individual response to the active ingredient, type of administration and time or interval in which the substance is administered. This in some cases it may be sufficient to use less than the aforementioned minimum dose, whereas in other cases the aforementioned upper limit must be exceeded. In the case of administration of larger doses, it may be advisable to divide them into multiple individual doses distributed throughout the day.

The following exemplary embodiments illustrate the invention. The invention is not limited to these examples.

The percentage amounts in the following tests and examples are percent by weight, unless otherwise indicated. Parts are parts by weight. Solvent ratios, dilution ratios and concentration data on liquid/liquid solutions are each based on volume.

A. Examples

Abbreviations and Acronyms
abs. absolute
Ac acetyl
aq. aqueous, aqueous solution
Boc tert-butoxycarbonyl
br. wide (in NMR)
sp. example
ca. circa, approx.
CI chemical ionization (in MS)
d doublet (in NMR)
d day(s)
TLC thin-layer chromatography
DCI direct chemical ionization (in MS)
dd doublet of doublet (in NMR)
DMAP 4-N,N-dimethylaminopyridine
DME 1,2-dimethoxyethane
DMF N,N-dimethylformamide
DMSO dimethyl sulfoxide
DPBS Dulbecco's phosphate-buffered saline solution
dt doublet of triplet (in NMR)
theor. of the theoretical
EDC N'-(3-dimethylaminopropyl)-N-ethylcarbodiimide hydrochloride
EI electron collision ionization (in MS)
eq. equivalent(s)
ESI electron spray ionization (in MS)
FCS fetal calf serum
Fmoc (9H-fluoren-9-ylmethoxy)carbonyl
GC-MS gas chromatography-linked mass spectrometry
sat. saturated
GTP guanosine 5'-triphosphate
h hour(s)
HATU O-(7-azabenzotriazol-1-yl-N,N,N',N'-tetramethyluronium hexafluorophosphate
HEPES 4-(2-hydroxyethyl)piperazine-1-ethanesulfonic acid
HOAc acetic acid
HOBt 1-hydroxy-1H-benzotriazole hydrate
HOSu N-hydroxysuccinimide
HPLC high-pressure, high-performance liquid chromatography
HR-MS high-resolution mass spectrometry
conc. concentrated
LC-MS liquid chromatography-linked mass spectrometry
m multiplet (in NMR)
min minute(s)
MS mass spectrometry
MTBE methyl-tert-butyl ether
MTT 3-(4,5-dimethylthiazol-2-yl)-2,5-diphenyl-2H-tetrazolium bromide
NMM N-methylmorpholine
NMP N-methyl-2-pyrrolidinone
NMR nuclear magnetic resonance spectrometry
PBS phosphate-buffered saline solution
Pd/C palladium on activated carbon
quant. quantitative (in yield)
quart quartet (in NMR)
quint quintet (in NMR)
$R_f$ retention index (in TLC)
RT room temperature
$R_t$ retention time (in HPLC)
singled (in NMR)
t triplet (in NMR)
tert tertiary
TFA trifluoroacetic acid
THF tetrahydrofuran
UV ultraviolet spectrometry
v/v volume to volume ratio (of a solution)
Z benzoxycarbonyl
tog. together
HPLC, LC-MS and GC-MS Methods:
Method 1 (LC-MS)
   Instrument: Waters Acquity SQD UPLC system; column: Waters Acquity UPLC HSS T3 1.8μ 50 mm×1 mm; eluent A: 1 liter water+0.25 mL 99% formic acid; eluent B: 1 liter acetonitrile+0.25 mL 99% formic acid; gradient: 0.0 min 90% A→1.2 min 5% A→2.0 min 5% A; flow rate: 0.40 mL/min; oven: 50° C.; UV detection: 210-400 nm.
Method 2 (LC-MS)
   Instrument: Micromass Quattro Premier with Waters UPLC Acquity; column: Thermo Hypersil GOLD 1.9μ 50 mm×1 mm; eluent A: 1 liter water+0.5 mL 50% formic acid; eluent B: 1 liter acetonitrile+0.5 mL 50% formic acid; gradient: 0.0 min 90% A→0.1 min 90% A→1.5 min 10% A→2.2 min 10% A; flow rate: 0.33 mL/min; oven: 50° C.; UV detection: 210 nm.
Method 3 (LC-MS)
   Instrument: Micromass Quattro Micro MS with HPLC Agilent series 1100; column: Thermo Hypersil GOLD 3μ 20 mm×4 mm; eluent A: 1 liter water+0.5 mL 50% formic acid; eluent B: 1 liter acetonitrile+0.5 mL 50% formic acid; gradient: 0.0 min 100% A→3.0 min 10% A→4.0 min 10% A→4.01 min 100% A (flow rate: 2.5 mL/min)→5.00 min 100% A; oven: 50° C.; flow rate: 2 mL/min; UV detection: 210 nm.

Method 4 (LC-MS)

Instrument type MS: Micromass ZQ; instrument type HPLC: HP 1100 series; UV DAD; column: Phenomenex Gemini 3µ 30 mm×3.00 mm; eluent A: 1 liter water+0.5 mL 50% formic acid; eluent B: 1 liter acetonitrile+0.5 mL 50% formic acid; gradient: 0.0 min 90% A→2.5 min 30% A→3.0 min 5% A→4.5 min 5% A; flow rate: 0.0 min 1 mL/min)→2.5 min/3.0 min/4.5 min 2 mL/min; oven: 50° C.; UV detection: 210 nm.

Method 5 (HPLC)

Instrument: HP 1090 series II; column: Merck Chromolith Speed ROD RP-18e, 50 mm×4.6 mm; precolumn: Merck Chromolith guard Cartridge Kit RP-18e, 5 mm×4.6 mm; injection volume: 5 µL; eluent A: 70% HClO$_4$ in water (4 mL/L); eluent B: acetonitrile; gradient: 0.00 min 20% B→4.00 min 20% B; flow rate: 5 mL/min; column temperature: 40° C.

Method 6 (HPLC)

Instrument: Waters 2695 with DAD 996; column: Merck Chromolith Speed ROD RP-18e, 50 mm×4.6 mm; precolumn: Merck Chromolith Guard Cartridge Kit RP-18c, 5 mm×4.6 mm; eluent A: 70% HCLO4 in water (4 mL/L); eluent B: acetonitrile; gradient: 0.00 min 5% B→3.00 min 95% B→4.00 min 95% B; flow rate: 5 mL/min.

Method 7 (LC-MS)

Instrument type: Waters ZQ; instrument type HPLC: Agilent 1100 series; UV DAD; column: Thermo Hypersil GOLD 3µ 20 mm×4 mm; eluent A: 1 liter water+0.5 mL 50% formic acid; eluent B: 1 liter acetonitrile+0.5 mL 50% formic acid; gradient: 0.0 min 100% A→3.0 min 10% A→4.0 min 10% A→4.1 min 100% A (flow rate: 2.5 mL/min); oven: 55° C.; flow rate: 2 mL/min; UV detection: 210 nm.

Method 8 (LC-MS)

Instrument type MS: Waters ZQ; instrument type HPLC: Agilent 1100 series; UV DAD; column: Thermo Hypersil GOLD 3µ 20 mm×4 mm; eluent A: 1 liter water+0.5 mL 50% formic acid; eluent B: 1 liter acetonitrile+0.5 mL 50% formic acid; gradient: 0.0 min 100% A→2.0 min 60% A→2.3 min 40% A→3.0 min 20% A→4.0 min 10% A→4.2 min 100% A (flow rate: 2.5 mL/min); oven: 55° C.; flow rate: 2 mL/min; UV detection: 210 nm.

Method 9 (LC-MS)

Instrument: Waters Acquity SQD UPLC system; column: Waters Acquity UPLC HSS T3 1.8µ 50 mm×1 mm; eluent A: 1 liter water+0.25 mL 99% formic acid; eluent B: 1 liter acetonitrile+0.25 mL 99% formic acid; gradient: 0.0 min 95% A→6.0 min 5% A→7.5 min 5% A; oven: 50° C.; flow rate: 0.35 mL/min; UV detection: 210-400 nm.

Method 10 (HPLC)

Instrument: Agilent 1200 series; column: Agilent Eclipse XDB-C18 5µ 4.6 mm×150 mm; pecolumn: Phenomenex KrudKatcher disposable precolumn; injection volume: 5 µL; eluent A: 1 liter water+0.01% trifluoroacetic acid; eluent B: 1 liter acetonitrile; gradient: 0.0 min 10% B→1.00 min 10% B→1.50 min 90% B→5.5 min 10% B; flow rate: 2 mL/min; column temperature: 30° C.

Method 11 (LC-MS)

Instrument: Waters Acquity SQD UPLC system; column: Waters Acquity UPLC HSS T3 1.8µ 30 mm×2 mm; eluent A: 1 liter water+0.25 mL 99% formic acid; eluent B: 1 liter acetonitrile+0.25 mL 99% formic acid; gradient: 0.0 min 90% A→1.2 min 5% A→2.0 min 5% A; flow rate: 0.60 mL/min; oven: 50° C.; UV detection: 208-400 nm.

Method 12 (GC-MS)

Instrument: Micromass GCT, GC 6890; column: Restek RTX-35, 15 m×200 µm×0.33 µm; constant flow rate of helium: 0.88 mL/min; oven: 70° C.; inlet: 250° C.; gradient: 70° C., 30° C./min→310° C. (3 min hold).

Method 13 (HR-MS)

Instrument: Thermo Scientific LTQ Orbitrap XL; FTMS ESI Positive

All reactants and reagents whose preparation procedures are not described explicitly below can be acquired commercially from generally accessible sources. For all other reactants and reagents, whose preparation procedures are also not described below and which were not available commercially or which were acquired from sources not generally available, the published literature describing their preparation has been referenced.

Starting Compounds and Intermediates

Starting Compound 1

(2R,3R)-3-[(2S)-1-(tert-Butoxycarbonyl)pyrrolidin-2-yl]-3-methoxy-2-methylpropanoic acid (Boc-Dolaproin) dicyclohexylamine salt

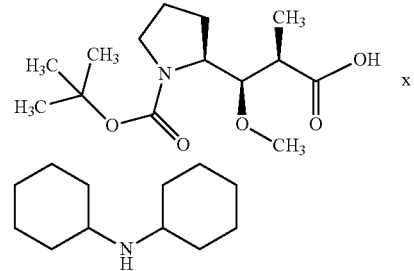

The title compound can be synthesized by various methods according to procedures described in the literature; see, e.g., Pettit et al., *Synthesis* 1996, 719; Shioiri et al., *Tetrahedron Lett.* 1991, 32, 931; Shioiri et al., *Tetrahedron* 1993, 49, 1913; Koga et al., *Tetrahydron Lett.* 1991, 32, 2395; Vidal et al., *Tetrahedron* 2004, 60, 9715; Poncet et al., *Tetrahedron* 1994, 50, 5345. It was synthesized here according to the procedure by Shioiri et al. (*Tetrahedron Lett.* 1991, 32, 931).

Starting Compound 2 tert-Butyl-(3R,4S,5S)-3-methoxy-5-methyl-4-(methylamino) heptanoate hydrochloride (Dolaisoleucin OtBu×HCl)

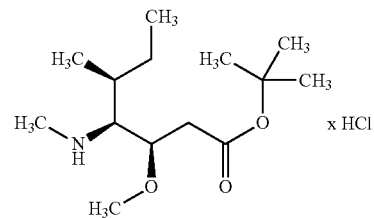 [SMILES: CC[C@H](C)[C@H](NC)[C@@H](CC(=O)OC(C)(C)C)OC]

The title compound can be synthesized by various methods described in the literature; see, e.g., Pettit et al., *J. Org. Chem.* 1994, 59, 1796; Koga et al., *Tetrahedron Lett.* 1991, 32, 2395; Shioiri et al., *Tetrahedron Lett.* 1991, 32, 931; Shioiri et al., *Tetrahedron* 1993, 49, 1913. It was synthesized here according to the procedure by Koga et al. (*Tetrahedron Lett.* 1991, 32, 2395).

Intermediate 1 tert-Butyl-(3R,4S,5S)-4-[{N-[(benzyloxy)carbonyl]-L-valyl}(methyl)amino]-3-methoxy-5-methyl heptanoate

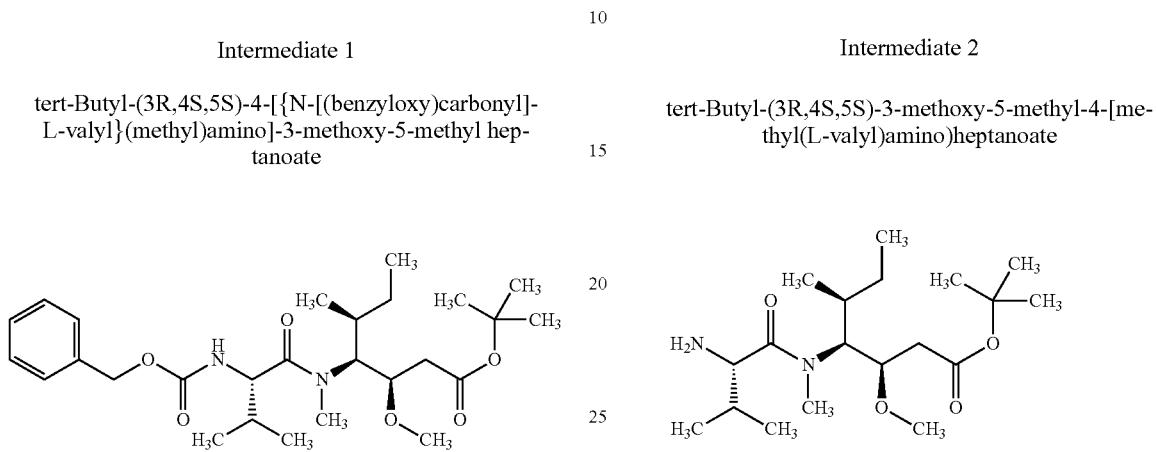

425 mg (1.7 mmol) N-[(benzyloxy)carbonyl]-L-valine was dissolved in 50 mL DMF and mixed in succession with 500 mg (1.7 mmol) tert-butyl-(3R,4S,5S)-3-methoxy-5-methyl-4-(methylamino) heptanoate hydrochloride (starting compound 2), 356 mg (1.9 mmol) 1-(3-dimethylaminopropyl)-3-ethylcarbodiimide hydrochloride, 285 mg (1.9 mmol) 1-hydroxy-1H-benzotriazole hydrate and 655 mg (5.1 mmol) N,N-diisopropylethylamine. The mixture was stirred for 20 hours at RT. Then 142 mg (0.5 mmol) N-[(benzyloxy)-carbonyl]-L-valine, 119 mg (0.6 mmol) 1-(3-dimethylaminopropyl)-3-ethylcarbodiimide hydrochloride, 95 mg (0.6 mmol) 1-hydroxy-1H-benzotriazole hydrate and 218 mg (1.7 mmol) N,N-diisopropylmethylamine were also added, and the mixture was treated ultrasonically for 90 min. The batch was then poured into a mixture of 50% saturated aqueous ammonium chloride solution and ethyl acetate. The organic phase was separated, then washed with saturated sodium bicarbonate solution and saturated sodium chloride solution, dried over magnesium sulfate, filtered and concentrated. The residue was then purified by preparative HPLC, yielding 329 mg (40% of the theoretical) of the title compound as a colorless oil.

HPLC (method 5): $R_t$=2.5 min;

LC-MS (method 1): $R_t$=1.45 min; MS (ESIpos): m/z=493 (M+H)$^+$.

Intermediate 2 tert-Butyl-(3R,4S,5S)-3-methoxy-5-methyl-4-[methyl(L-valyl)amino)heptanoate 500 mg (1 mmol) tert-Butyl-(3R,4S,5S)-4[{N-[(benzyloxy)carbonyl]-(L-valyl}(methyl)-amino]-3-methoxy-5-methylheptanoate (intermediate 1) was dissolved in 50 mL methanol and hydrogenated for one hour at RT under normal pressure after adding 100 mg 10% palladium on activated carbon. The catalyst was then filtered out and the solvent was removed in vacuo, yielding 370 mg (quantitative) of the title compound as an almost colorless oil.

HPLC (method 5): $R_t$=1.59 min;

LC-MS (method 1): $R_t$=0.74 min; MS (ESIpos): m/z=359 (M+H)$^+$.

Intermediate 3

N-[(9H-Fluoren-9-ylmethoxy)carbonyl]-N-methyl-L-valyl-N-[(3R,4S,5S)-1-tert-butoxy-3-methoxy-5-methyl-1-oxoheptan-4-yl]-N-methyl-L-valinamide

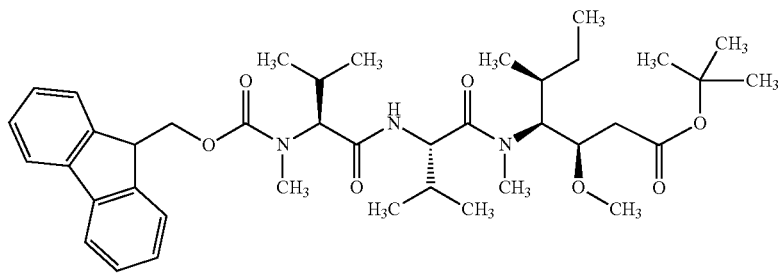 [SMILES: CC[C@H](C)[C@@H]([C@@H](CC(=O)OC(C)(C)C)OC)N(C)C(=O)[C@@H](NC(=O)[C@H](C(C)C)N(C)C(=O)OCC1c2ccccc2-c2ccccc21)C(C)C]

396 mg (1.1 mmol) N-[(9H-fluoren-9-ylmethoxy)carbonyl]-N-methyl-L-valine was dissolved in DMF and then mixed in succession with 365 mg (1 mmol) tert-butyl-(3R,4S,5S)-3-methoxy-5-methyl-4-[methyl(L-valyl)amino]heptanoate (intermediate 2), 234 mg (1.2 mmol) 1-(3-dimethylaminopropyl)-3-ethylcarbodiimide hydrochloride and 187 mg (1.2 mmol) 1-hydroxy-1H-benzotriazole hydrate. The mixture was stirred over night at RT. The batch was then poured into a mixture of 50% saturated aqueous ammonium chloride solution and ethyl acetate. The organic phase was separated, washed in succession with saturated sodium bicarbonate solution and saturated sodium chloride solution, dried over magnesium sulfate, filtered and concentrated. The residue was used directly in the next step without further purification.

Yield: 660 mg (68% of the theoretical)
HPLC (method 5): $R_t$=3.0 min;
LC-MS (method 1): $R_t$=1.61 min; MS (ESIpos): m/z=694 (M+H)$^+$.

Intermediate 4

N-[(9H-Fluoren-9-ylmethoxy)carbonyl]-N-methyl-L-valyl-N-[(2R,3S,4S)-1-carboxy-2-methoxy-4-methylhexan-3-yl]-N-methyl-L-valinamide

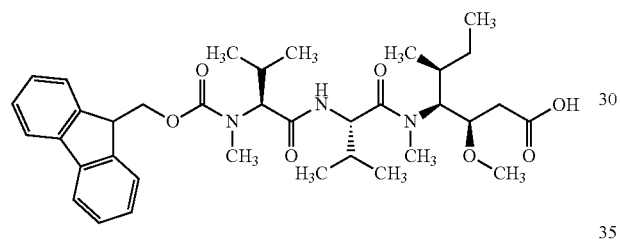

650 mg (0.94 mmol) N-[(9H-fluoren-9-ylmethoxy)carbonyl]-N-methyl-L-valyl-N-[(3R,4S,5S)-1-tert-butoxy-3-methoxy-5-methyl-1-oxoheptan-4-yl]-N-methyl-L-valinamide (intermediate 3) was dissolved in 5 mL dichloromethane, mixed with 5 mL trifluoroacetic acid and stirred over night at RT. Then the mixture was concentrated in vacuo, and the remaining residue was purified by preparative HPLC, yielding 430 mg (72% of the theoretical) of the title compound as a colorless foam.

HPLC (method 5): $R_t$=2.4 min;
LC-MS (method 2): $R_t$=1.51 min; MS (ESIpos): m/z=638 (M+H)$^+$.

Intermediate 5

N-tert-Butoxycarbonyl)-N-methyl-L-valyl-N-[(2R,3S,4S)-1-carboxy-2-methoxy-4-methyl-hexan-3-yl]-N-methyl-L-valinamide

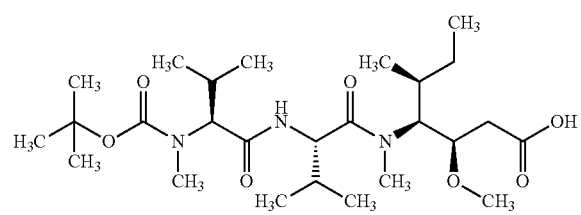 [SMILES: CC[C@H](C)[C@@H]([C@@H](CC(=O)O)OC)N(C)C(=O)[C@@H](NC(=O)[C@H](C(C)C)N(C)C(=O)OC(C)(C)C)C(C)C]

51 mg (0.08 mmol) N-[(9H-fluoren-9-ylmethoxy)carbonyl]-N-methyl-L-valyl-N-[(2R,3S,4S)-1-carboxy-2-methoxy-4-methylhexan-3-yl]-N-methyl-L-valinamide (intermediate 4) was dissolved in 10 mL DMF and mixed with 0.5 mL piperidine. After stirring for 10 min at RT, the batch was concentrated in vacuo and the residue was stirred with diethyl ether. The insoluble ingredients were filtered out and washed several times with diethyl ether. Then the filter residue was dissolved in 5 mL dioxane/water (1:1) and the solution was adjusted to pH 11 with 1N sodium hydroxide solution. While treating with ultrasound, a total of 349 mg (1.6 mmol) di-tert-butyl dicarbonate was added in several portions, while the pH of the solution was kept at 11. After the end of the reaction, the dioxane was evaporated and the pH of the aqueous solution was adjusted to 2-3 with citric acid. Extraction was performed twice with 50 mL ethyl acetate each time. The organic phases were combined, dried over magnesium sulfate and concentrated in vacuo. The residue was dissolved in diethyl ether and the product was precipitated with pentane. The solvent was separated by decanting. The residue was digested again with pentane and finally dried in a high vacuum, yielding 31 mg (93% of the theoretical) of the title compound.

HPLC (method 6): $R_t$=2.2 min;
LC-MS (method 2): $R_t$=1.32 min; MS (ESIpos): m/z=516 (M+H)$^+$.

Intermediate 6

Benzyl-(2R,3S)-methoxy-2-methyl-3-[(2S)-pyrrolidin-2-yl]propanoate trifluoroacetic acid salt

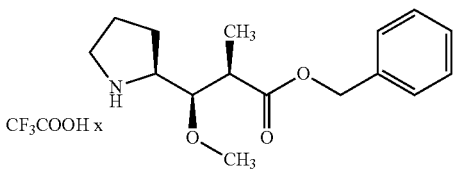 [SMILES: CO[C@@H]([C@@H]1CCCN1)[C@@H](C)C(=O)OCc1ccccc1]

First, (2R,3R)-3-[(2S)-1-(tert-butoxycarbonyl)pyrrolidin-2-yl]-3-methoxy-2-methylpropanoic acid was released from 1.82 g (3.88 mmol) of the dicyclohexylamine salt (starting compound 1) by dissolving it in 150 mL ethyl acetate and extracting with 100 mL 0.5% aqueous sulfuric acid. The organic phase was dried over magnesium sulfate, filtered and concentrated. The residue was dissolved in 10 mL dioxane and 10 mL water, mixed with 1517 mg (4.66 mmol) cesium carbonate and treated for 5 min in an ultrasonic bath. It was then concentrated in vacuo and the residue was co-distilled once with DMF. The residue was then dissolved in 15 mL DMF and mixed with 1990 mg (11.64 mmol) benzyl bromide. The mixture was treated in an ultrasonic bath for 15 min and then concentrated in vacuo. The residue was distributed between ethyl acetate and water. The organic phase was separated, washed with sodium chloride solution and then concentrated. The residue was finally purified by preparative HPLC, thereby yielding 1170 mg (80% of the theoretical) of the Boc-protected intermediate tert-butyl-(2S)-2-[(1R,2R)-3-(benzyloxy)-1-methoxy-2-methyl-3-oxopropyl]pyrrolidine-1-carboxylate.

This 1170 mg of the intermediate was immediately dissolved in 15 mL dichloromethane and mixed with 5 mL trifluoroacetic acid. After stirring for 15 min at RT, the batch was concentrated in vacuo and the residue was lyophilized from dioxane. After drying in a high vacuum, there remained 1333 mg (84% of the theoretical) of the title compound as a yellow oil.

HPLC (method 5): $R_t$=1.5 min;
LC-MS (method 1): $R_t$=0.59 min; MS (ESIpos): m/z=278 (M+H)$^+$.

Intermediate 7

N-(tert-Butoxycarbonyl)-N-methyl-L-valyl-N-[(3R,4S,5S)-1-{(2S)-2-[(1R,2R)-2-carboxy-1-methoxypropyl]pyrrolidin-1-yl}-3-methoxy-5-methyl-1-oxoheptan-4-yl]-N-methyl-L-valinamide

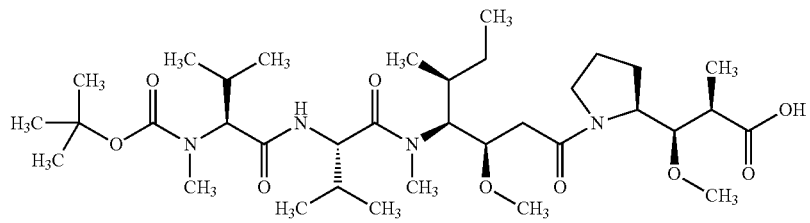 [SMILES: CC[C@H](C)[C@@H]([C@@H](CC(=O)N1CCC[C@H]1[C@H](OC)[C@@H](C)C(=O)O)OC)N(C)C(=O)[C@@H](NC(=O)[C@H](C(C)C)N(C)C(=O)OC(C)(C)C)C(C)C]

1200 mg (2.33 mmol) N-(tert-butoxycarbonyl)-N-methyl-L-valyl-N-[(2R,3S,4S)-1-carboxy-2-methoxy-4-methylhexan-3-yl]-N-methyl-L-valinamide (intermediate 5) was combined with 910.8 mg (2.33 mmol) benzyl-(2R,3R)-3-methoxy-2-methyl-3-[(2S)-pyrrolidin-2-yl]propanoate trifluoroacetic acid salt (intermediate 6), 1327 mg (3.49 mmol) O-(7-azabenzotriazol-1-yl)-N,N,N',N'-tetramethyluronium hexafluorophosphate and 2027 μL N,N-diisopropylethylamine in 50 mL DMF and stirred for 5 min at RT. Next the solvent was removed in vacuo. The remaining residue was dissolved in ethyl acetate and then extracted with 5% aqueous citric acid solution and saturated sodium bicarbonate solution in succession. The organic phase was separated and concentrated. The residue was purified by preparative HPLC. The product fractions were combined, concentrated and the residue was dried in a high vacuum, yielding 1000 mg (55% of the theoretical) of the benzyl ester intermediate N-(tert-butoxycarbonyl)-N-methyl-L-valyl-N-[(3R,4S,5S)-1-{(2S)-2-[(1R,2R)-3-benzyloxy)-1-methoxy-2-methyl-3-oxopropyl]pyrrolidin-1-yl}-3-methoxy-5-methyl-1-oxoheptan-4-yl]-N-methyl-L-valinamide as a resin.

LC-MS (method 1): $R_t$=1.56 min; MS (ESIpos): m/z=775 (M+H)$^+$.

The total amount of the intermediate obtained was dissolved in 25 mL of a mixture of methanol and dichloromethane (20:1) and the benzyl ester group was removed by hydrogenation under normal pressure with 10% palladium on activated carbon as the catalyst. After stirring for 30 min at RT, the catalyst was filtered out and the filtrate was concentrated in vacuo, yielding 803 mg (91% of the theoretical) of the title compound as a white solid.

HPLC (method 5): $R_t$=2.1 min;

LC-MS (method 1): $R_t$=1.24 min; MS (ESIpos): m/z=685 (M+H)$^+$.

Intermediate 8

N$^\alpha$-(tert-Butoxycarbonyl)-N-methoxy-N-methyl-L-phenylalaninamide

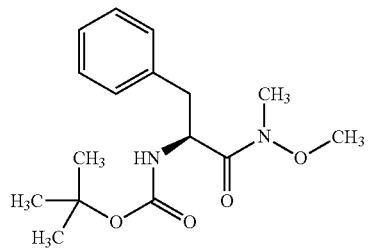

1000 mg (3.77 mmol) N-(tert-butoxycarbonyl)-L-phenylalanine was placed in 10 mL dichloromethane and mixed with 733 mg (4.52 mmol) 1,1'-carbonyldiimidazole. The batch was stirred for 15 min until the evolution of gas had stopped. Next the mixture was mixed with 441 mg (4.52 mmol) N,O-dimethylhydroxylamine hydrochloride and 657 μL (3.77 mmol) N,N-diisopropylethylamine and stirred for 1 hour at RT. Next the batch was diluted with dichloromethane and washed with distilled water, 0.5N hydrochloric acid and saturated sodium chloride solution in succession. The organic phase was separated and the combined aqueous phases were re-extracted with ethyl acetate. The combined organic phases were dried over magnesium sulfate and concentrated in vacuo, yielding 1090 mg (93% of the theoretical) of the title compound.

LC-MS (method 1): $R_t$=1.02 min; MS (ESIpos): m/z=309 (M+H)$^+$.

Intermediate 9 tert-Butyl-[(2S)-1-oxo-3-phenylpropan-2-yl]carbamate

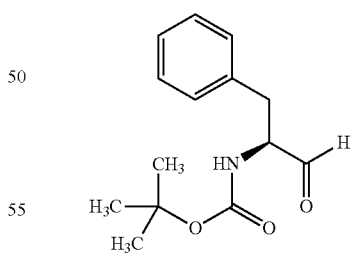

1090 mg (3.5 mmol) N$^\alpha$-(tert-butoxycarbonyl)-N-methoxy-N-methyl-L-phenylalanine-amide was dissolved in 20 mL 2-methyltetrahydrofuran and cooled to 0° C. Then 4.2 mL (4.2 mmol) of a 1M lithium aluminum hydride solution was added slowly to THF, and the reaction mixture was stirred for 30 min at 0° C. Next 5% aqueous potassium hydrogen sulfate solution was added cautiously. The batch was then diluted with water and extracted with MTBE. The organic phase was dried over magnesium sulfate and concentrated in vacuo, yielding 820 mg (94% of the theoretical) of the title compound.

GC-MS (method 12): $R_t$=5.61 mm; MS (ESIpos): m/z=220 (M−29)$^+$ $^1$H-NMR (500 MHz, DMSO-d$_6$): δ [ppm]=1.15-1.42 (m, 9H), 7.11-7.39 (m, 5H), 9.52 (s, 1H) [additional signals concealed beneath solvent peaks]

Intermediate 10

(2S,3Z)-1,5-Diphenylpent-3-en-2-amine trifluoroacetic acid salt

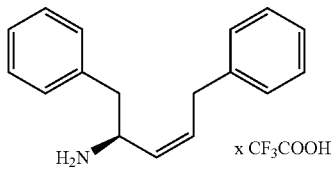 [SMILES: N[C@H](/C=C\Cc1ccccc1)Cc1ccccc1]

Under argon, 842 μL (2.1 mmol) 2.5 M n-butyllithium solution in hexane was added to a suspension of 986 mg (2.2 mmol) triphenyl-(2-phenylethyl)phosphonium bromide [can be synthesized, e.g., according to R. W. Hartmann, M. Reichert, *Archiv der Pharmazie* 333, 145 (2000); K. C. Nicolaou et al., *European J. Chem.* 1, 467 (1995)] in 125 mL THF at −78° C., and the mixture was then stirred for one hour at 0° C. The reaction mixture was then cooled back to −78° C. and a solution of 500 mg (2.0 mmol) tert-butyl-[(2S)-1-oxo-3-phenylpropan-2-yl]carbamate in 5 mL dry THF was added. The batch was heated to 0° C. and stirred further for three hours at this temperature. The reaction was then terminated by adding saturated aqueous ammonium chloride solution. The mixture was diluted with MTBE, the phases were separated, and the organic phase was dried over magnesium sulfate and concentrated in vacuo. The residue was purified over a silica gel column using cyclohexane/ethyl acetate 5:1 as the mobile phase. After concentrating the corresponding fractions, 173 mg (25.6% of the theoretical) of the Boc-protected intermediate, tert-butyl-[(2S,3Z)-1,5-diphenylpent-3-en-2-yl]carbamate was obtained.

$^1$H-NMR (400 MHz, DMSO-d$_6$): δ [ppm]=1.16-1.46 (m, 9H), 2.62 (dd, J=13.20 Hz, 7.34 Hz, 1H), 2.73-3.18 (m, 1H), 4.56 (t, J=7.46 Hz, 1H), 5.27-5.57 (m, 1H), 6.98-7.32 (m, 10H) [additional signals concealed beneath solvent peaks].

173 mg (512 μmol) of the intermediate tert-butyl[2S,3Z)-1,5-diphenylpent-3-en-2-yl]carbamate was placed in 16 mL dichloromethane, mixed with 4 mL trifluoroacetic acid and left to stand for 30 min at RT. Next the reaction mixture was concentrated and the residue was dried in vacuo, yielding 180 mg (99% of the theoretical) of the title compound.

LC-MS (method 1): $R_t$=0.74 min; MS (ESIpos): m/z=238 (M+H)$^+$.

$^1$H-NMR (400 MHz, DMSO-d$_6$): δ [ppm]=2.64-2.83 (m, 1H), 2.88-3.22 (m, 2H), 4.00-4.55 (m, 1H), 5.16-5.46 (m, 1H), 5.48-5.78 (m, 1H), 6.60-6.89 (m, 2H), 7.14 (s, 3H), 7.22-7.36 (m, 5H), 7.89-8.27 (m, 2H).

Intermediate 11

(2S)-1-(Benzylsulfonyl)-3-phenylpropan-2-amine

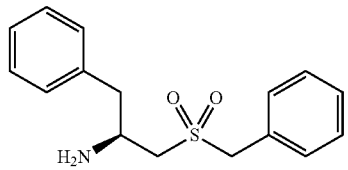 [SMILES: N[C@@H](Cc1ccccc1)CS(=O)(=O)Cc1ccccc1]

200 mg (1.13 mmol) (4S)-4-benzyl-1,3-benzyl-1,3-oxazolidin-2-one was placed in 3 mL tert-butanol and mixed with 280 mg (2.26 mmol) benzylmercaptan. The mixture was then heated at reflux for two days. Then the batch was concentrated on the rotary evaporator and the resulting intermediate (2S)-1-(benzylsulfanyl)-3-phenylpropan-2-amine was reacted further without workup.

HPLC (method 10): $R_t$=2.63 min;

LC-MS (method 1): $R_t$=0.67 min; MS (ESIpos): m/z=258 (M+H)$^+$.

The crude intermediate obtained above was dissolved in a solution of 2 mL 30% hydrogen peroxide and 5 mL formic acid and stirred for 12 h at RT. Then the reaction mixture was poured into saturated aqueous sodium sulfate solution and extracted three times with ethyl acetate. The organic phase was dried over magnesium sulfate and concentrated in vacuo. The resulting raw product was purified by preparative HPLC, thus yielding 343 mg (61% of the theoretical) of the title compound.

HPLC (method 10): $R_t$=2.40 min;

LC-MS (method 1): $R_t$=0.65 min; MS (ESIpos): m/z=290 (M+H)$^+$.

Intermediate 12

(2S,3Z)-1,4-Diphenylbut-3-en-2-amine

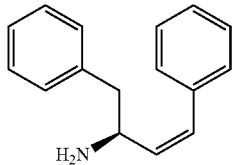 [SMILES: N[C@H](/C=C\c1ccccc1)Cc1ccccc1]

552.7 mg (9.85 mmol) potassium hydroxide was dissolved in methanol, absorbed onto 1.1 g aluminum oxide and then dried in a high vacuum. At 5-10° C., 307 μL (3.3 mmol) dibromodifluoromethane was added by drops to a solution of 240 mg (0.82 mmol) (2S)-1-benzylsulfonyl)-3-phenylpropan-2-amine and 1.56 g of the potassium hydroxide prepared in this way on aluminum oxide in 6.2 mL n-butanol. The reaction mixture was stirred for two hours at RT, then filtered through Celite, and the residue was rewashed well with dichloromethane. The filtrate was concentrated and the resulting residue was dried in vacuo. The resulting raw produce was purified by preparative HPLC, yielding 98 mg (35% of the theoretical) of the title compound with an E/Z diasteromer ratio of 4:1.

HPLC (method 10): $R_t$=2.46 min;

LC-MS (method 1): $R_t$=0.75 min; MS (ESIpos): m/z=224 (M+H)$^+$.

The E/Z diastereomer mixture obtained above was dissolved in 2 mL ethanol and 0.2 mL N,N-diisopropylethylamine and separated over HPLC on a chiral phase [column: Daicel Chiralpak AD-H, 5 μm, 250 mm×20 mm; eluent: hexane/(ethanol+0.2% diethylamine) 50:50 v/v; UV detection: 220 nm; temperature: 30° C.]. The corresponding fractions were concentrated on a rotary evaporator and the residue was dried in vacuo, yielding 10 mg of the title compound as a pure Z isomer.

$^1$H-NMR (400 MHz, DMSO-d$_6$): δ [ppm]=2.71 (d, J=6.60 Hz, 2H), 3.73-3.95 (m, 1H), 5.42-5.67 (m, 1H), 6.21-6.50 (m, 1H), 7.08-7.38 (m, 10H) [additional signals concealed beneath solvent peaks].

Intermediate 13

(2S,3E)-1,4-Diphenylbut-3-en-2-amine

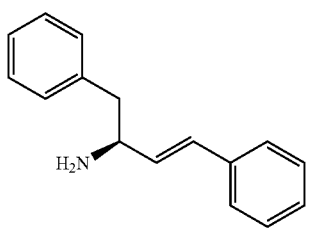 [SMILES: N[C@H](/C=C/c1ccccc1)Cc1ccccc1]

The title compound (pure E isomer) was obtained in a yield of 45 mg in the course of chromatographic diastereomer separation on a chiral phase, as described for intermediate 12.

$^1$H-NMR (400 MHz, DMSO-d$_6$): δ [ppm]=2.62-2.83 (m, 2H), 3.52-3.71 (m, 1H), 6.18-6.30 (m, 1H), 6.34-6.46 (m, 1H), 6.98-7.57 (m, 10H) [additional signals concealed beneath solvent peaks].

Intermediate 14

(1S)-2-Phenyl-1-(5-phenyl-1,3,4-oxadiazol-2-yl) ethanamine trifluoroacetic acid salt

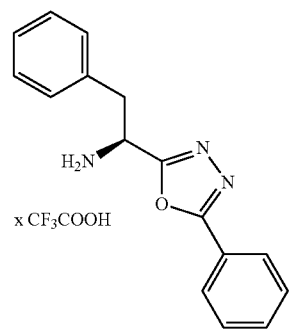 [SMILES: N[C@@H](Cc1ccccc1)c1nnc(-c2ccccc2)o1]

200 mg (0.75 mmol) N-(tert-butoxycarbonyl)-L-phenylalanine was placed in 5.5 mL dichloromethane at 0° C. and mixed with 128 mg (0.79 mmol) 1,1'-carbonyldiimidazole. After 30 min, 103 mg (0.75 mmol) benzoyl hydrazide was added. Finally, after 45 min more at 0° C., 500 mg (1.5 mmol) carbon tetrabromide and 395 mg (1.5 mmol) triphenylphosphine were added. The batch was first stirred for 2 h at 0° C. and then stirred over night at RT. The mixture was then concentrated on a rotary evaporator and the residue was dried in a high vacuum. The resulting raw product was purified by preparative HPLC, yielding 217 mg (78% of the theoretical) of the Boc-protected intermediate tert-butyl-[(1S)-2-phenyl-1-(5-phenyl-1,3,4-oxadiazol-2-yl)ethyl]carbamate.

HPLC (method 10): $R_t$=3.01 min;

LC-MS (method 1): $R_t$=1.15 min; MS (ESIpos): m/z=366 (M+H)$^+$.

217 mg (0.59 mmol) of this intermediate was dissolved in 3 mL dichloromethane, mixed with 0.6 mL trifluoroacetic acid and stirred for 30 min at RT. Then the mixture was concentrated in vacuo. The remaining residue was dried further in vacuo and then lyophilized from dioxane, thereby yielding 214 mg (90% of the theoretical) of the title compound as a white solid.

HPLC (method 10): $R_t$=2.43 min;

LC-MS (method 1): $R_t$=0.62 min; MS (ESIpos): m/z=266 (M+H)$^+$.

Intermediate 15

(1R)-2-Phenyl-1-(5-phenyl-1,3,4-oxadiazol-2-yl)ethanamine trifluoroacetic acid salt

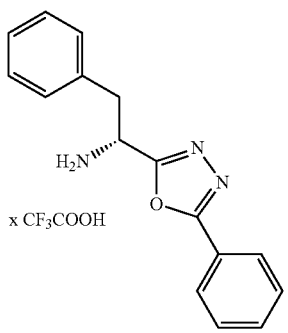 [SMILES: N[C@H](Cc1ccccc1)c1nnc(-c2ccccc2)o1]

200 mg (0.75 mmol) N-(tert-butoxycarbonyl)-D-phenylalanine was placed in 5.5 mL dichloromethane at 0° C. and mixed with 128.3 mg (0.79 mmol) 1,1'-carbonyldiimidazole. After 30 min, 103 mg (0.75 mmol) benzoyl hydrazide was added. Finally, after 45 min more at 0° C., 500 mg (1.5 mmol) carbon tetrabromide and 395 mg (1.5 mmol) triphenylphosphine were added. The batch was first stirred for 2 h at 0° C. and then stirred over night at RT. The mixture was then concentrated on a rotary evaporator and the residue was dried in a high vacuum. The resulting raw product was purified by preparative HPLC, yielding 219 mg (80% of the theoretical) of the Boc-protected intermediate tert-butyl-[(1R)-2-phenyl-1-(5-phenyl-1,3,4-oxadiazol-2-yl)ethyl]carbamate.

HPLC (method 10): $R_t$=3.01 min;

LC-MS (method 2): $R_t$=1.36 min; MS (ESIpos): m/z=366 (M+H)$^+$.

219 mg (0.6 mmol) of this intermediate was dissolved in 3 mL dichloromethane, mixed with 0.6 mL trifluoroacetic acid and stirred for 30 min at RT. Next the mixture was concentrated in vacuo. The remaining residue was dried further in vacuo and then lyophilized from dioxane, thus yielding 196 mg (86% of the theoretical) of the title compound as a white solid.

HPLC (method 10): $R_t$=2.41 min.

Intermediate 16

Methyl-4-[(1E,3S)-3-amino-4-phenylbut-1-en-1-yl)benzoate trifluoroacetic acid salt

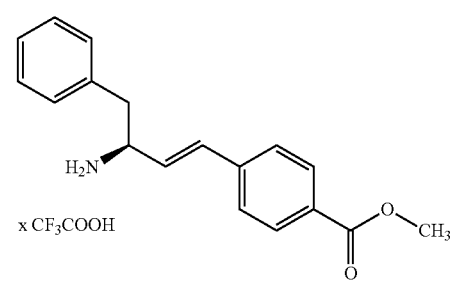 [SMILES: COC(=O)c1ccc(/C=C/[C@@H](N)Cc2ccccc2)cc1]

0.9 mg (4 µmol) palladium acetate was placed in 5 mL DMF and then mixed in succession with 20.8 mg (97 µmol) methyl-4-bromobenzoate, 20 mg (81 µmol) (S)-tert-butyl-1-phenylbut-3-en-2-ylcarbamate, 1.1 mg (8 µmol) phenylurea and 11.2 mg (81 µmol) potassium carbonate. The reaction mixture was then stirred for 15 min at 160° C. in a microwave apparatus (Emrys™ Optimizer). The mixture was then filtered and the filtrate was separated into its components by preparative HPLC (eluent: methanol/water gradient with 0.1% TFA), yielding 21.3 mg (68% of the theoretical) of the title compound.

HPLC (method 10): $R_t$=3.23 min;

LC-MS (method 11): $R_t$=1.32 min; MS (ESIpos): m/z=382 (M+H)$^+$.

Intermediate 17

N-Methyl-L-valyl-N-[(3R,4S,5S)-1-{(2S)-2-[(1R,2R)-3-{[(2S,3Z)-1,5-diphenylpent-3-en-2-yl]amino}-1-methoxy-2-methyl-3-oxopropyl]pyrrolidin-1-yl}-3-methoxy-5-methyl-1-oxoheptan-4-yl]-N-methyl-L-valinamide trifluoroacetic acid salt

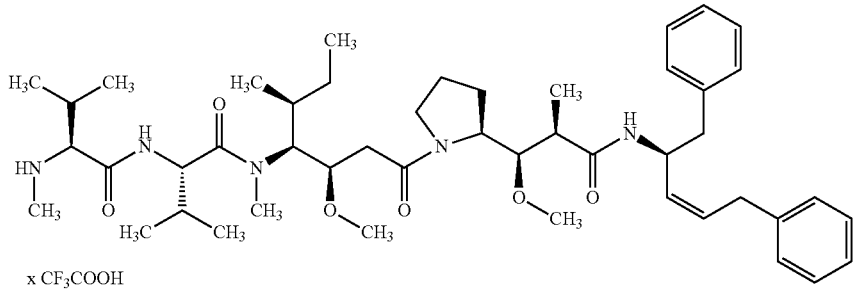 [SMILES: CC[C@H](C)[C@@H]([C@@H](CC(=O)N1CCC[C@H]1[C@H](OC)[C@@H](C)C(=O)N[C@H](/C=C\Cc1ccccc1)Cc1ccccc1)OC)N(C)C(=O)[C@@H](NC(=O)[C@@H](NC)C(C)C)C(C)C]

x CF₃COOH 15 mg (22 µmol) N-(tert-butoxycarbonyl)-N-methyl-L-valyl-N-[(3R,4S,5S)-1-{2S)-2-[(1R,2R)-2-carboxy-1-methoxypropyl]pyrrolidin-yl}-3-methoxy-5-methyl-1-oxoheptan-4-yl]-N-methyl-L-valinamide (intermediate 7) was placed in 750 µL DMF and mixed with 11.44 µL (66 µmol) N,N-diisopropylethylamine and 10 mg (26 µmol HATU. The batch was stirred for 30 min at RT. Then 8.5 mg (24 µmol) (2S,3Z)-1,5-diphenylpent-3-en-2-amine trifluoroacetic acid salt (intermediate 10) was added and the batch was stirred over night at RT. The reaction mixture was then immediately separated into its components by preparative HPLC, yielding 18.1 mg (91% of the theoretical) of the Boc-protected intermediate N-(tert-butoxycarbonyl)-N-methyl-L-valyl-N-[(3R,4S,5S)-1-{(2S)-2-[(1R,2R)-3-{[(2S,3Z)-1,5-diphenylpent-3-en-2-yl]amino)-1-methoxy-2-methyl-3-oxopropyl]pyrrolidin-1-yl)-3-methoxy-5-methyl-1-oxoheptan-4-yl]-N-methyl-L-valinamide in the form of a white solid.

HPLC (method 10): $R_t$=4.74 min;
LC-MS (method 11): $R_t$=1.58 min; MS (ESIpos): m/z=905 (M+H)⁺.

16 mg (18 µmol) of this intermediate was dissolved in 1 mL dichloromethane, mixed with 0.2 mL trifluoroacetic acid and stirred for 30 min at RT. Then the mixture was concentrated in vacuo. The remaining residue was dried further in vacuo and then the dioxane was lyophilized, thus yielding 15.8 mg (97% of the theoretical) of the title compound.

HPLC (method 10): $R_t$=2.66 min;

LC-MS (method 1): $R_t$=1.03 min; MS (ESIpos): m/z=805 (M+H)⁺.

Intermediate 18

N-Methyl-L-valyl-N-[(3R,4S,5S)-1-{(2S)-2-[(1R,2R)-3-{[(2S,3Z)-1,4-diphenylbut-3-en-2-yl]amino}-1-methoxy-2-methyl-3-oxopropyl]pyrrolidin-1-yl}-3-methoxy-5-methyl-1-oxoheptan-4-yl]-N-methyl-L-valinamide trifluoroacetic acid salt

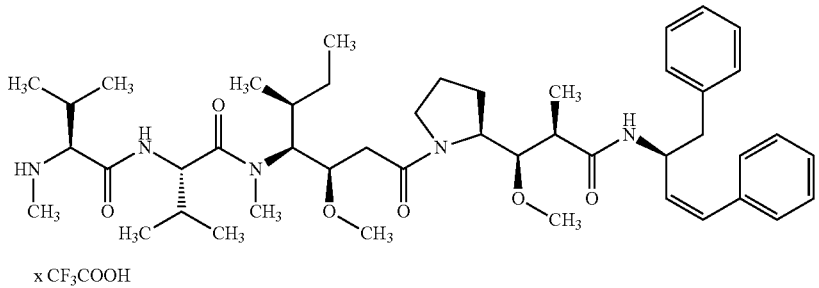 [SMILES: CC[C@H](C)[C@@H]([C@@H](CC(=O)N1CCC[C@H]1[C@H](OC)[C@@H](C)C(=O)N[C@H](/C=C\c1ccccc1)Cc1ccccc1)OC)N(C)C(=O)[C@@H](NC(=O)[C@@H](NC)C(C)C)C(C)C]

x CF₃COOH

First, N-(tert-butoxycarbonyl)-N-methyl-L-valyl-N-[(3R,4S,5S)-1-{(2S)-2-[(1R,2R)-3-{[(2S,3Z)-1,4-diphenylbut-3-en-2-yl]amino}-1-methoxy-2-methyl-3-oxopropyl]-pyrrolidin-1-yl}-3-methoxy-5-methyl-1-oxoheptan-4-yl]-N-methyl-L-valinamide was synthesized by analogy with the synthesis of intermediate 17 by reacting 20 mg (29 µmol) N-(tert-butoxycarbonyl)-N-methyl-L-valyl-N-[(3R,4S,5S)-1-{(2S)-2-[(1R,2R)-2-carboxy-1-methoxypropyl]pyrrolidin-1-yl}-3-methoxy-5-methyl-1-oxoheptan-4-yl]-N-methyl-L-valinamide (intermediate 7) with 7.1 mg (32 µmol) (2S,3Z)-1,4-diphenylbut-3-en-2-amine (intermediate 12).

Yield: 9.2 mg (35% of the theoretical)
HPLC (method 10): $R_t$=4.52 min;
LC-MS (method 1): $R_t$=1.54 min; MS (ESIpos): m/z=891 (M+H)⁺.

Then 9.5 mg (99% of the theoretical) of the title compound was obtained by subsequent cleavage of the Boc protective group with trifluoroacetic acid.

HPLC (method 10): $R_t$=2.58 min;

LC-MS (method 1): R$_t$=0.97 min; MS (ESIpos): m/z=791 (M+H)$^+$.

Intermediate 19

N-Methyl-L-valyl-N-[(3R,4S,5S)-1-{(2S)-2-[(1R,2R)-3-{[(2S,3E)-1,4-diphenylbut-3-en-2-yl]amino}-1-methoxy-2-methyl-3-oxopropyl]pyrrolidin-1-yl}-3-methoxy-5-methyl-1-oxoheptan-4-yl]-N-methyl-L-valinamide trifluoroacetic acid salt

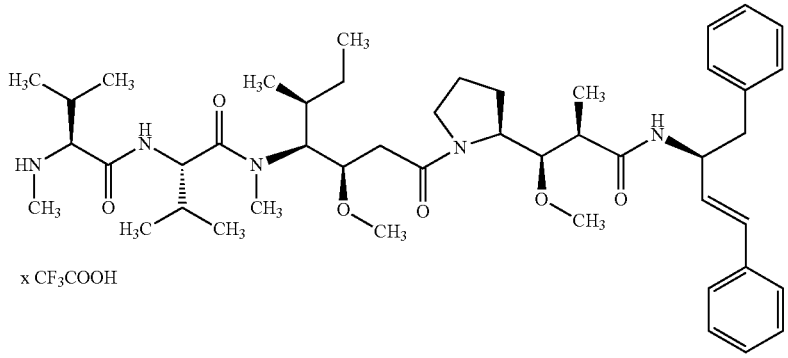 [SMILES: CC[C@H](C)[C@@H]([C@@H](CC(=O)N1CCC[C@H]1[C@H](OC)[C@@H](C)C(=O)N[C@H](/C=C/c1ccccc1)Cc1ccccc1)OC)N(C)C(=O)[C@@H](NC(=O)[C@@H](NC)C(C)C)C(C)C]

x CF$_3$COOH

First, N-(tert-butoxycarbonyl)-N-methyl-L-valyl-N-[(3R,4S,5S)-1-{(2S)-2-[(1R,2R)-3-{[(2S,3E)-1,4-diphenylbut-3-en-2-yl]amino}-1-methoxy-2-methyl-3-oxopropyl]-pyrrolidin-1-yl}-3-methoxy-5-methyl-1-oxoheptan-4-yl]-N-methyl-L-valinamide was synthesized by analogy with the synthesis of intermediate 17 by reacting 20 mg (29 μmol) N-(tert-butoxycarbonyl)-N-methyl-L-valyl-N-[(3R,4S,5S)-1-{(2S)-2-[(1R,2R)-2-carboxy-1-methoxypropyl]pyrrolidin-1-yl}-3-methoxy-5-methyl-1-oxoheptan-4-yl]-N-methyl-L-valinamide (intermediate 7) with 7.1 mg (32 μmol) (2S,3E)-1,4-diphenylbut-3-en-2-amine (intermediate 13).

Yield: 15.1 mg (58% of the theoretical)

HPLC (method 10): R$_t$=4.2 min;

LC-MS (method 1): R$_t$=1.51 min; MS (ESIpos): m/z=891 (M+H)$^+$.

Then 15.7 mg (99% of the theoretical) of the title compound was obtained by subsequent cleavage of the Boc protective group with trifluoroacetic acid.

HPLC (method 10): R$_t$=2.62 min;

LC-MS (method 1): R$_t$=0.97 min; MS (ESIpos): m/z=791 (M+H)$^+$.

Intermediate 20

N-Methyl-L-valyl-N-[(3R,4S,5S)-1-{(2S)-2-[(1R,2R)-3-{[(2S)-1-benzylsulfonyl)-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide trifluoroacetic acid salt

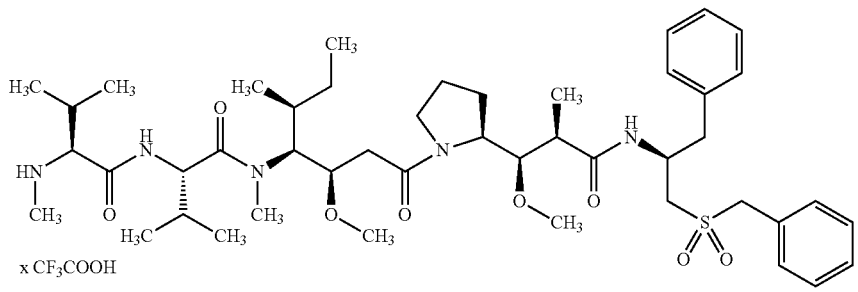 [SMILES: CC[C@H](C)[C@@H]([C@@H](CC(=O)N1CCC[C@H]1[C@H](OC)[C@@H](C)C(=O)N[C@@H](Cc1ccccc1)CS(=O)(=O)Cc1ccccc1)OC)N(C)C(=O)[C@@H](NC(=O)[C@@H](NC)C(C)C)C(C)C]

x CF$_3$COOH

First, N-(tert-butoxycarbonyl)-N-methyl-L-valyl-N-[(3R,4S,5S)-1-{(2S)-2-[(1R,2R)-3-{[(2S)-1-benzylsulfonyl)-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide was synthesized by analogy with the synthesis of intermediate 17 by reacting 20 mg (29 μmol) N-(tert-butoxycarbonyl)-N-methyl-L-valyl-N-[(3R,4S,5S)-1-{(2S)-2-[(1R,2R)-2-carboxy-1-methoxypropyl]pyrrolidin-1-yl}-3-methoxy-5-methyl-1-oxoheptan-4-yl]-N-methyl-L-valinamide (intermediate 7) with 9.3 mg (20 μmol) (2S)-1-(benzylsulfanyl)-3-phenylpropan-2-amine (intermediate 11).

Yield: 19.2 mg (68% of the theoretical)

HPLC (method 10): R$_t$=3.5 min;

LC-MS (method 1): R$_t$=1.41 min; MS (ESIpos): m/z=957 (M+H)$^+$.

Then 19.3 mg (99% of the theoretical) of the title compound was obtained by subsequently splitting off the Boc protective group with trifluoroacetic acid.

HPLC (method 10): $R_t$=2.52 min;
LC-MS (method 1): $R_t$=0.86 min; MS (ESIpos): m/z=857 (M+H)$^+$.

HPLC (method 10): $R_t$=2.52 min;
LC-MS (method 1): $R_t$=0.85 min; MS (ESIpos): m/z=833 (M+H)$^+$.

Intermediate 21

N-Methyl-L-valyl-N-[(3R,4S,5S)-3-methoxy-1-{(2S)-2-[(1R,2R)-1-methoxy-2-methyl-3-oxo-3-{[(1S)-2-phenyl-1-(5-phenyl-1,3,4-oxadiazol-2-yl)ethyl]amino}propyl]pyrrolidin-1-yl}-5-methyl-1-oxoheptan-4-yl]-N-methyl-L-valinamide trifluoroacetic acid salt Intermediate 22

N-Methyl-L-valyl-N-[(3R,4S,5S)-3-methoxy-1-{(2S)-2-[(1R,2R)-1-methoxy-2-methyl-3-oxo-3-{[(1R)-2-phenyl-1-(5-phenyl-1,3,4-oxadiazol-2-yl)ethyl]amino}propyl]pyrrolidin-1-yl}-5-methyl-1-oxoheptan-4-yl]-N-methyl-L-valinamide trifluoroacetic acid salt

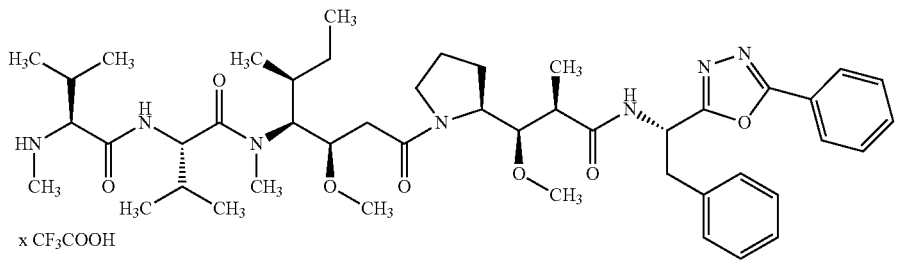 [SMILES: CC[C@H](C)[C@@H]([C@@H](CC(=O)N1CCC[C@H]1[C@H](OC)[C@@H](C)C(=O)N[C@@H](Cc1ccccc1)c1nnc(-c2ccccc2)o1)OC)N(C)C(=O)[C@@H](NC(=O)[C@@H](NC)C(C)C)C(C)C]

First, N-(tert-butoxycarbonyl)-N-methyl-L-valyl-N-[(3R,4S,5S)-3-methoxy-1-{(2S)-2-[(1R,2R)-1-methoxy-2-methyl-3-oxo-3-{[(1S)-2-phenyl-1-(5-phenyl-1,3,4-oxadiazol-2-yl)ethyl]amino}propyl]pyrrolidin-1-yl}-5-methyl-1-

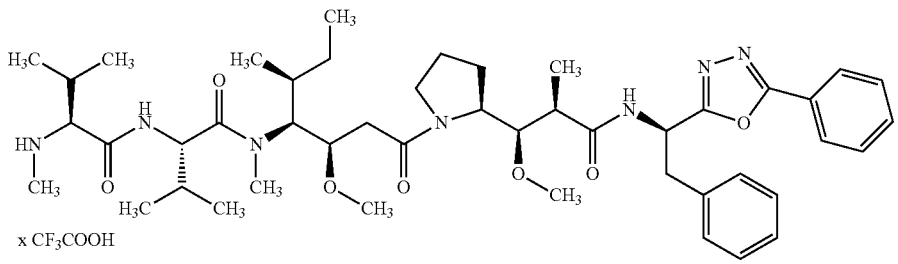 [SMILES: CC[C@H](C)[C@@H]([C@@H](CC(=O)N1CCC[C@H]1[C@H](OC)[C@@H](C)C(=O)N[C@H](Cc1ccccc1)c1nnc(-c2ccccc2)o1)OC)N(C)C(=O)[C@@H](NC(=O)[C@@H](NC)C(C)C)C(C)C]

oxoheptan-4-yl]-N-methyl-L-valinamide was synthesized by analogy with the synthesis of intermediate 17 by reacting 20 mg (29 µmol) N-(tert-butoxycarbonyl)-N-methyl-L-valyl-N-[(3R,4S,5S)-1-{(2S)-2-[(1R,2R)-2-carboxy-1-methoxypropyl]pyrrolidin-1-yl}-3-methoxy-5-methyl-1-oxoheptan-4-yl]-N-methyl-L-valinamide (intermediate 7) with 12.2 mg (32 µmol) (1S)-2-phenyl-1-(5-phenyl-1,3,4-oxadiazol-2-yl)ethanamine trifluoroacetic acid salt (intermediate 14).

Yield: 22 mg (81% of the theoretical)
HPLC (method 10): $R_t$=3.74 min;
LC-MS (method 1): $R_t$=1.45 min; MS (ESIpos): m/z=933 (M+H)$^+$.

Then 22.4 mg (98% of the theoretical) of the title compound was obtained by subsequently splitting off the Boc protective group with trifluoroacetic acid.

First, N-(tert-butoxycarbonyl)-N-methyl-L-valyl-N-[(3R,4S,5S)-3-methoxy-1-{(2S)-2-[(1R,2R)-1-methoxy-2-methyl-3-oxo-3-{[(1R)-2-phenyl-1-(5-phenyl-1,3,4-oxadiazol-2-yl)ethyl]amino}propyl]pyrrolidin-1-yl}-5-methyl-1-oxoheptan-4-yl]-N-methyl-L-valinamide was synthesized by analogy with the synthesis of intermediate 17 by reacting 20 mg (29 µmol) N-(tert-butoxycarbonyl)-N-methyl-L-valyl-N-[(3R,4S,5S)-1-{(2S)-2-[(1R,2R)-2-carboxy-1-methoxypropyl]pyrrolidin-1-yl}-3-methoxy-5-methyl-1-oxoheptan-4-yl]-N-methyl-L-valinamide (intermediate 7) with 12.2 mg (32 µmol) (1R)-2-phenyl-1-(5-phenyl-1,3,4-oxadiazol-2-yl)ethanamine trifluoroacetic acid salt (intermediate 15).

Yield: 17 mg (64% of the theoretical)
HPLC (method 10): $R_t$=3.74 min;
LC-MS (method 1): $R_t$=1.45 min; MS (ESIpos): m/z=933 (M+H)$^+$.

Then 17.1 mg (99% of the theoretical) of the title compound was obtained by subsequently splitting off the Boc protective group with trifluoroacetic acid.

HPLC (method 10): $R_t$=2.55 min;

LC-MS (method 11): $R_t$=0.85 min; MS (ESIpos): m/z=833 (M+H)$^+$.

Intermediate 23

N-Methyl-L-valyl-N-[(3R,4S,5S)-3-methoxy-1-{(2S)-2-[(1R,2R)-1-methoxy-3-{[(2S,3E)-4-[4-(methoxycarbonyl)phenyl]-1-phenylbut-3-en-2-yl}amino)-2-methyl-3-oxopropyl]pyrrolidin-1-yl}-5-methyl-1-oxoheptan-4-yl]-N-methyl-L-valinamide trifluoroacetic acid salt

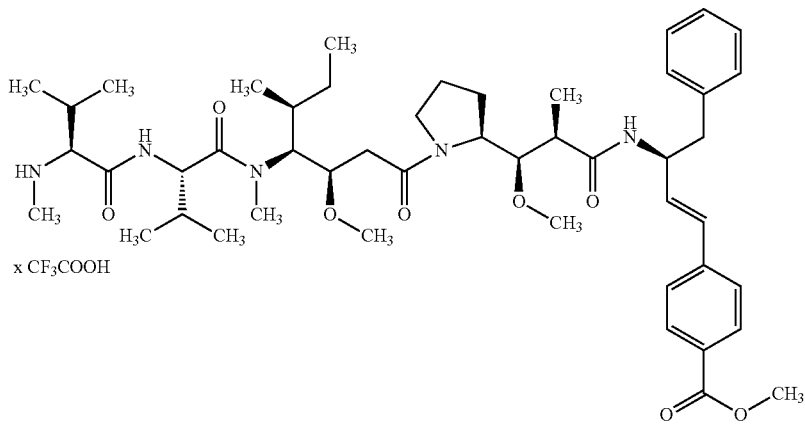 [SMILES: CC[C@H](C)[C@@H]([C@@H](CC(=O)N1CCC[C@H]1[C@H](OC)[C@@H](C)C(=O)N[C@H](/C=C/c1ccc(C(=O)OC)cc1)Cc1ccccc1)OC)N(C)C(=O)[C@@H](NC(=O)[C@@H](NC)C(C)C)C(C)C]

First, N-(tert-butoxycarbonyl)-N-methyl-L-valyl-N-[(3R,4S,5S)-3-methoxy-1-{(2S)-2-[(1R,2R)-1-methoxy-3-{[(2S,3E)-4-[4-(methoxycarbonyl)phenyl]-1-phenylbut-3-en-2-yl}amino)-2-methyl-3-oxopropyl]pyrrolidin-1-yl}-5-methyl-1-oxoheptan-4-yl]-N-methyl-L-valinamide was synthesized by analogy with the synthesis of intermediate 17 by reacting 20 mg (29 µmol) N-(tert-butoxycarbonyl)-N-methyl-L-valyl-N-[(3R,4S,5S)-1-{(2S)-2-[(1R,2R)-2-carboxy-1-methoxypropyl]pyrrolidin-1-yl}-3-methoxy-5-methyl-1-oxoheptan-4-yl]-N-methyl-L-valinamide (intermediate 7) with 12.7 mg (32 µmol) methyl-4-[(1E,3S)-3-amino-4-phenylbut-1-en-1-yl]benzoate trifluoroacetic acid salt (intermediate 16).

Yield: 8.8 mg (32% of the theoretical)

LC-MS (method 1): $R_t$=1.53 min; MS (ESIpos): m/z=949 (M+H)$^+$.

Then 8 mg (90% of the theoretical) of the title compound was obtained by subsequently splitting off the Boc protective group with trifluoroacetic acid.

LC-MS (method 1): $R_t$=1.00 min; MS (ESIpos): m/z=849 (M+H)$^+$.

Intermediate 24

N-Methyl-L-valyl-N-[(3R,4S,5S)-1-{(2S)-2-[(1R,2R)-3-{[2-(1H-indol-3-yl)ethyl]amino}-1-methoxy-2-methyl-3-oxopropyl]pyrrolidin-1-yl}-3-methoxy-5-methyl-1-oxoheptan-4-yl]-N-methyl-L-valinamide trifluoroacetic acid salt

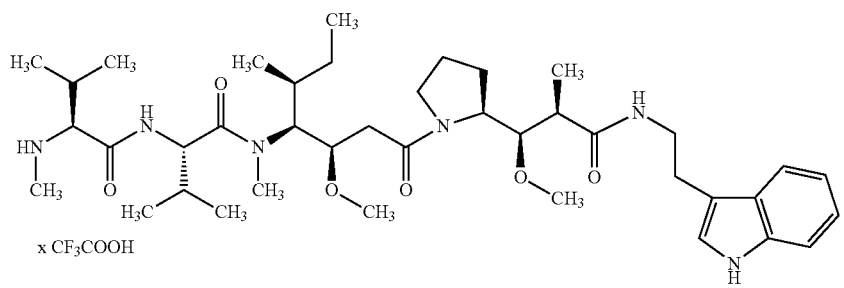 [SMILES: CC[C@H](C)[C@@H]([C@@H](CC(=O)N1CCC[C@H]1[C@H](OC)[C@@H](C)C(=O)NCCc1c[nH]c2ccccc12)OC)N(C)C(=O)[C@@H](NC(=O)[C@@H](NC)C(C)C)C(C)C]

76 µL (438 µmol) N,N-diisopropylethylamine, 83 mg (219 µmol HATU and 26 mg (161 µmol) 2-(1H-indol-3-yl)ethanamine were added to a solution of 100 mg (146 µmol) N-(tert-butoxycarbonyl)-N-methyl-L-valyl-N-[(3R,4S,5S)-1-{2S)-2-[(1R,2R)-2-carboxy-1-methoxypropyl]pyrrolidinyl}-3-methoxy-5-methyl-1-oxoheptan-4-yl]-N-methyl-L-valinamide (intermediate 7) in 30 mL DMF at RT. The mixture was stirred for 15 min at RT. Then the reaction mixture was concentrated in vacuo and the residue was separated into its components by preparative HPLC, yielding 101 mg (83% of the theoretical) of the Boc-protected intermediate, N-(tert-butoxycarbonyl)-N-methyl-L-valyl-N-[(3R,4S,5S)-1-{(2S)-2-[(1R,2R)-3-{[2-(1H-indoll-3-yl)ethyl]amino}-1-methoxy-2-methyl-3-oxopropyl]pyrrolidin-1-yl)-3-methoxy-5-methyl-1-oxoheptan-4-yl]-N-methyl-L-valinamide.

LC-MS (method 1): $R_t$=1.32 min; m/z=828 (M+H)$^+$.

101 mg (122 μmol) of this intermediate was dissolved in 15 mL dichloromethane, mixed with 1 mL trifluoroacetic acid and stirred for 30 min at RT. Then the mixture was concentrated in vacuo and the remaining residue was lyophilized from water/acetonitrile, yielding 108 mg of the title compound in a quantitative yield as an almost colorless foam.

LC-MS (method 1): $R_t$=0.84 min; MS (ESIpos): m/z=728 (M+H)$^+$.

Intermediate 25

N-Methyl-L-valyl-N-[(3R,4S,5S)-1-{(2S)-2-[(1R,2R)-1-methoxy-2-methyl-3-oxo-3-[(2-phenylethyl)amino]propyl}pyrrolidin-1-yl]-5-methyl-1-oxoheptan-4-yl}-N-methyl-L-valinamide trifluoroacetic acid salt

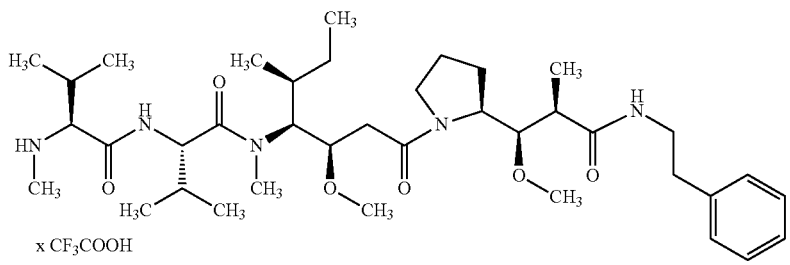 [SMILES: CC[C@H](C)[C@@H]([C@@H](CC(=O)N1CCC[C@H]1[C@H](OC)[C@@H](C)C(=O)NCCc1ccccc1)OC)N(C)C(=O)[C@@H](NC(=O)[C@@H](NC)C(C)C)C(C)C]

The title compound was obtained by analogy with the synthesis of intermediate 24 in two steps, starting with 60 mg (88 μmol) of intermediate 7 by coupling with 10 mg (88 μmol) 2-phenylethanamine and then splitting off Boc using trifluoroacetic acid. this yielded 34 mg (97% of the theoretical) of the title compound.

HPLC (method 5): $R_t$=2.71 min;

LC-MS (method 1): $R_t$=0.80 min; MS (ESIpos): m/z=689 (M+H)±.

EXEMPLARY EMBODIMENTS

Example 1

N-(3-Carboxypropyl)-N-methyl-L-valyl-N-[(3R,4S,5S)-1-{(2S)-2-[(1R,2R)-3-{[(2S,3Z)-1,5-diphenylpent-3-en-2-yl]amino}-1-methoxy-2-methyl-3-oxopropyl]pyrrolidin-1-yl}-3-methoxy-5-methyl-1-oxoheptan-4-yl]-N-methyl-L-valinamide

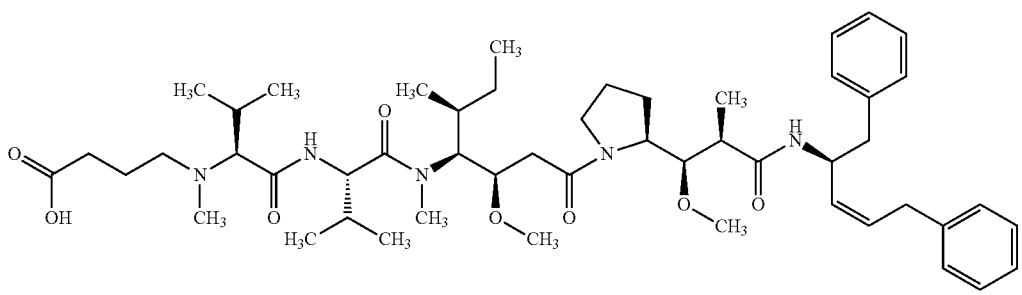 [SMILES: CC[C@H](C)[C@@H]([C@@H](CC(=O)N1CCC[C@H]1[C@H](OC)[C@@H](C)C(=O)N[C@H](/C=C\Cc1ccccc1)Cc1ccccc1)OC)N(C)C(=O)[C@@H](NC(=O)[C@H](C(C)C)N(C)CCCC(=O)O)C(C)C]

14.5 mg (16 μmol) N-methyl-L-valyl-N-[(3R,4S,5S)-1-{(2S)-2-[(1R,2R)-3-{[(2S,3Z)-1,5-diphenylpent-3-en-2-yl]amino}-1-methoxy-2-methyl-3-oxopropyl]pyrrolidin-1-yl}-3-methoxy-5-methyl-1-oxoheptan-4-yl]-N-methyl-L-valinamide trifluoroacetic acid salt (intermediate 17) was dissolved in 1 mL dioxane/water (1:1) and mixed with 20.4 μL (32 μmol) of a 15% aqueous solution of 4-oxobutanoic acid. The batch was then stirred for one hour at 100° C. After cooling to RT, 1.1 mg (17 μmol) sodium cyanoborohydride was added and the mixture was adjusted to a pH of 3 by adding approx. 150 μL 0.1N hydrochloric acid. The batch was then stirred for two hours more at 100° C. Then 1.1 mg (17 μmol) sodium cyanoborohydride was added again and the mixture was next adjusted to a pH of 3 by adding approx. 300 μL 0.1N hydrochloric acid. The batch was then stirred again for two hours at 100° C. If the reaction was still incomplete, this procedure was repeated once more. Finally, the batch was concentrated and the raw product was purified by preparative HPLC and lyophilized from dioxane, thereby yielding 13.1 mg (93% of the theoretical) of the title compound in the form of a white solid.

HPLC (method 10): $R_t$=2.63 min;

LC-MS (method 1): $R_t$=1.01 min; MS (ESIpos): m/z=891 (M+H)$^+$.

Example 2

N-(3-Carboxypropyl)-N-methyl-L-valyl-N-[(3R,4S,5S)-1-{(2S)-2-[(1R,2R)-3-{[(2S,3Z)-1,4-diphenylbut-3-en-2-yl]amino}-1-methoxy-2-methyl-3-oxopropyl]pyrrolidin-1-yl}-3-methoxy-5-methyl-1-oxoheptan-4-yl]-N-methyl-L-valinamide

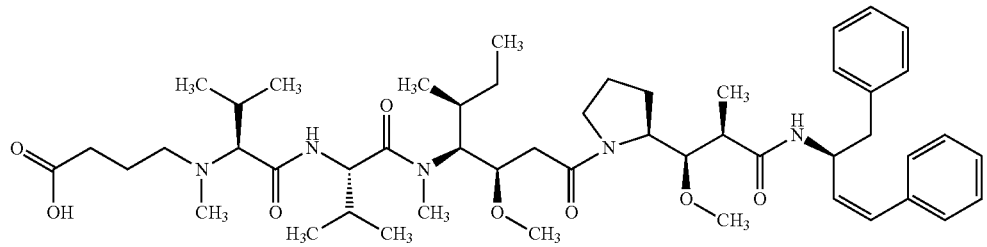 [SMILES: CC[C@H](C)[C@@H]([C@@H](CC(=O)N1CCC[C@H]1[C@H](OC)[C@@H](C)C(=O)N[C@H](/C=C\c1ccccc1)Cc1ccccc1)OC)N(C)C(=O)[C@@H](NC(=O)[C@H](C(C)C)N(C)CCCC(=O)O)C(C)C]

9 mg (10 µmol) N-methyl-L-valyl-N-[(3R,4S,5S)-1-{(2S)-2-[(1R,2R)-3-{[(2S,3Z)-1,4-diphenylbut-3-en-2-yl]amino}-1-methoxy-2-methyl-3-oxopropyl]pyrrolidin-1-yl}-3-methoxy-5-methyl-1-oxoheptan-4-yl]-N-methyl-L-valinamide trifluoroacetic acid salt (intermediate 18) was dissolved in 0.6 mL dioxane/water (1:1) and reacted with a 15% aqueous solution of 4-oxobutanoic acid in the presence of sodium cyanoborohydride in a process similar to the synthesis in Example 1. After lyophilization from dioxane, 5.6 mg (64% of the theoretical) of the title compound was obtained in the form of a white solid.

HPLC (method 10): $R_t$=2.61 min;

LC-MS (method 11): $R_t$=0.94 min; MS (ESIpos): m/z=877 (M+H)$^+$.

HR-MS (method 13): m/z=876.5.

15.5 mg (10 µmol) N-methyl-L-valyl-N-[(3R,4S,5S)-1-{(2S)-2-[(1R,2R)-3-{[(2S,3E)-1,4-diphenylbut-3-en-2-yl]amino}-1-methoxy-2-methyl-3-oxopropyl]pyrrolidin-1-yl}-3-methoxy-5-methyl-1-oxoheptan-4-yl]-N-methyl-L-valinamide trifluoroacetic acid salt (intermediate 19) was dissolved in 1.0 mL dioxane/water (1:1) and reacted with a 15% aqueous solution of 4-oxobutanoic acid in the presence of sodium cyanoborohydride, by analogy with the synthesis in Example 1. After lyophilization from dioxane, 10.3 mg (68% of the theoretical) of the title compound was obtained in the form of a white solid.

HPLC (method 10): $R_t$=2.59 min;

LC-MS (method 11): $R_t$=0.94 min; MS (ESIpos): m/z=877 (M+H)$^+$.

HR-MS (method 13): m/z=876.6;

$^1$H-NMR (500 MHz, dichloromethane-d$_2$): δ [ppm]=0.72-1.21 (m, 18H), 1.23-1.47 (m, 3H), 1.51-2.22 (m, 8H), 2.25-2.54 (m, 5H), 2.65-2.86 (m, 2H), 2.90-3.47 (m, 16H), 3.53-4.46 (m, 6H), 4.71-5.27 (m, 4H), 5.46-5.72 (m, 1H), 6.10-6.36 (m, 1H), 6.44-6.67 (m, 2H), 7.03-7.67 (m, 10H), 9.13 (br. s, 1H)

Example 3

N-(3-Carboxypropyl)-N-methyl-L-valyl-N-[(3R,4S,5S)-1-{(2S)-2-[(1R,2R)-3-{[(2S,3E)-1,4-diphenylbut-3-en-2-yl]amino}-1-methoxy-2-methyl-3-oxopropyl]pyrrolidin-1-yl}-3-methoxy-5-methyl-1-oxoheptan-4-yl]-N-methyl-L-valinamide

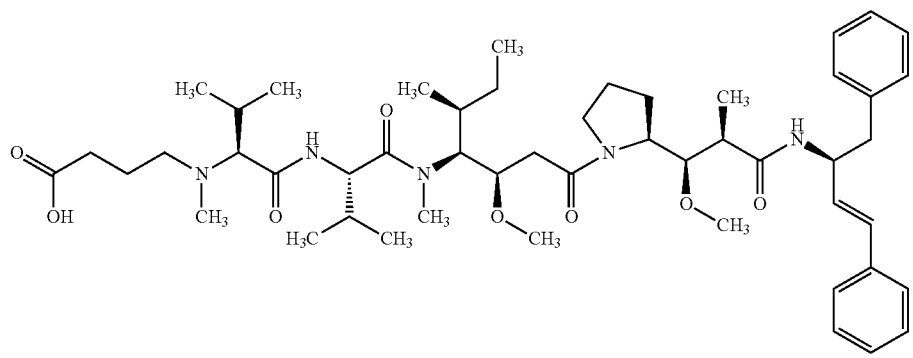 [SMILES: CC[C@H](C)[C@@H]([C@@H](CC(=O)N1CCC[C@H]1[C@H](OC)[C@@H](C)C(=O)N[C@H](/C=C/c1ccccc1)Cc1ccccc1)OC)N(C)C(=O)[C@@H](NC(=O)[C@H](C(C)C)N(C)CCCC(=O)O)C(C)C]

Example 4

N-(3-Carboxypropyl)-N-methyl-L-valyl-N-[(3R,4S,5S)-1-{(2S)-2-[(1R,2R)-3-{[(2S)-1-(benzylsulfanyl)-3-phenylpropan-2-yl]amino}-1-methoxy-2-methyl-3-oxopropyl]-pyrrolidin-1-yl}-3-methoxy-5-methyl-1-oxoheptan-4-yl]-N-methyl-L-valinamide

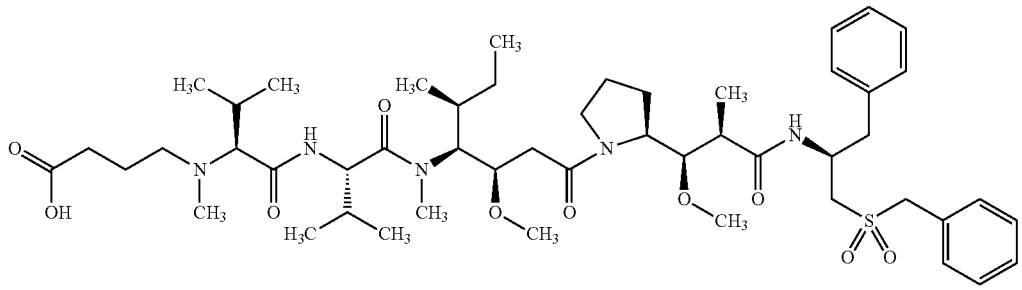 [SMILES: CC[C@H](C)[C@@H]([C@@H](CC(=O)N1CCC[C@H]1[C@H](OC)[C@@H](C)C(=O)N[C@@H](Cc1ccccc1)CS(=O)(=O)Cc1ccccc1)OC)N(C)C(=O)[C@@H](NC(=O)[C@H](C(C)C)N(C)CCCC(=O)O)C(C)C]

19.3 mg (20 μmol) N-methyl-L-valyl-N-[(3R,4S,5S)-1-{(2S)-2-[(1R,2R)-3-{[(2S)-1-(benzylsulfanyl)-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide trifluoroacetic acid salt (intermediate 20) was dissolved in 1.2 mL dioxane/water (1:1) and reacted with a 15% aqueous solution of 4-oxobutanoic acid in the presence of sodium cyanoborohydride, by analogy with the synthesis in Example 1. After lyophilization from dioxane, 8.6 mg (45% of the theoretical) of the title compound was obtained in the form of a white solid.

LC-MS (method 11): $R_t$=0.85 min; MS (ESIpos): m/z=943 (M+H)$^+$.

HR-MS (method 13): m/z=942.6;

$^1$H-NMR (500 MHz, dichloromethane-d$_2$): δ [ppm]=0.72-1.23 (m, 18H), 1.26-1.56 (m, 2H), 1.60-1.94 (m, 4H), 1.95-2.17 (m, 3H), 2.22-2.54 (m, 5H), 2.69-2.87 (m, 2H), 2.90-3.27 (m, 11H), 3.31-3.53 (m, 8H), 3.58-4.20 (m, 7H), 4.25-4.54 (m, 3H), 4.59-5.15 (m, 4H), 6.22 (br. s, 1H), 6.97-8.00 (m, 10H), 9.13 (br. s, 1H)

Example 5

N-(3-Carboxypropyl)-N-methyl-L-valyl-N-[(3R,4S,5S)-3-methoxy-1-{(2S)-2-[(1R,2R)-1-methoxy-2-methyl-3-oxo-3-{[(1S)-2-phenyl-1-(5-phenyl-1,3,4-oxadiazol-2-yl)ethyl]amino}propyl]pyrrolidin-1-yl}-5-methyl-1-oxoheptan-4-yl]-N-methyl-L-valinamide 22.4 mg (24 μmol) N-methyl-L-valyl-N-[(3R,4S,5S)-3-methoxy-1-{(2S)-2-[(1R,2R)-1-methoxy-2-methyl-3-oxo-3-{[(1S)-2-phenyl-1-(5-phenyl-1,3,4-oxadiazol-2-yl)ethyl]amino}propyl]pyrrolidin-1-yl}-5-methyl-1-oxoheptan-4-yl]-N-methyl-L-valinamide trifluoroacetic acid salt (intermediate 21) was dissolved in 1.4 mL dioxane/water (1:1) and reacted with a 15% aqueous solution of 4-oxobutanoic acid in the presence of sodium cyanoborohydride by analogy with the synthesis according to Example 1. After lyophilization from dioxane, 8.2 mg (38% of the theoretical) of the title compound was obtained in the form of a white solid.

HPLC (method 10): $R_t$=2.54 min;

LC-MS (method 1): $R_t$=0.94 min; MS (ESIpos): m/z=919 (M+H)$^+$.

HR-MS (method 13): m/z=918.6;

$^1$H-NMR (500 MHz, dichloromethane-d$_2$): δ [ppm]=0.58-1.21 (m, 20H), 1.25-1.52 (m, 2H), 1.62-2.19 (m, 8H), 2.28-2.50 (m, 5H), 2.64-2.84 (m, 2H), 2.89-3.16 (m, 6H), 3.19-3.52 (m, 10H), 3.59-4.00 (m, 4H), 4.02-4.40 (m, 3H), 4.66-5.13 (m, 3H), 5.61 (d, 1H), 7.32 (d, 5H), 7.49-7.69 (m, 3H), 7.93-8.16 (m, 2H), 9.07 (br. s, 1H).

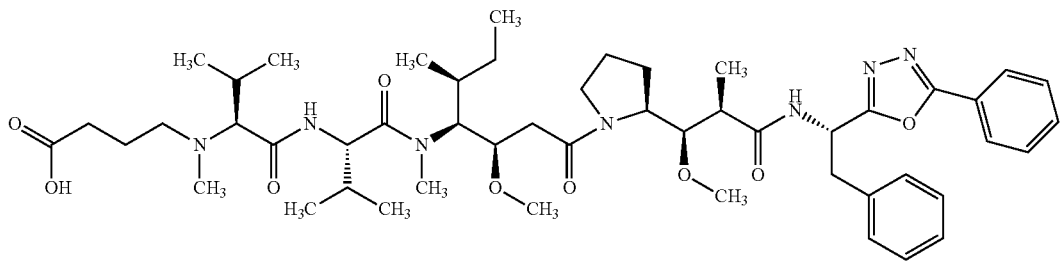 [SMILES: CC[C@H](C)[C@@H]([C@@H](CC(=O)N1CCC[C@H]1[C@H](OC)[C@@H](C)C(=O)N[C@@H](Cc1ccccc1)c1nnc(-c2ccccc2)o1)OC)N(C)C(=O)[C@@H](NC(=O)[C@H](C(C)C)N(C)CCCC(=O)O)C(C)C]

Example 6

N-(3-Carboxypropyl)-N-methyl-L-valyl-N-[(3R,4S,5S)-3-methoxy-1-{(2S)-2-[(1R,2R)-1-methoxy-2-methyl-3-oxo-3-{[(1R)-2-phenyl-1-(5-phenyl-1,3,4-oxadiazol-2-yl)ethyl]amino}propyl]pyrrolidin-1-yl}-5-methyl-1-oxoheptan-4-yl]-N-methyl-L-valinamide

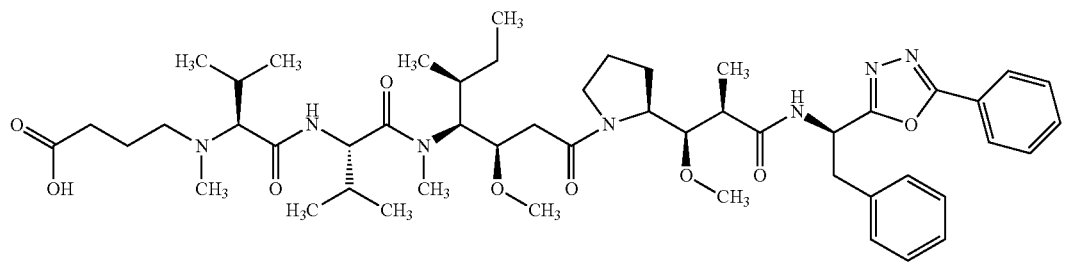 [SMILES: CC[C@H](C)[C@@H]([C@@H](CC(=O)N1CCC[C@H]1[C@H](OC)[C@@H](C)C(=O)N[C@H](Cc1ccccc1)c1nnc(-c2ccccc2)o1)OC)N(C)C(=O)[C@@H](NC(=O)[C@H](C(C)C)N(C)CCCC(=O)O)C(C)C]

17.1 mg (18 μmol) N-methyl-L-valyl-N-[(3R,4S,5S)-3-methoxy-1-{(2S)-2-[(1R,2R)-1-methoxy-2-methyl-3-oxo-3-{[(1R)-2-phenyl-1-(5-phenyl-1,3,4-oxadiazol-2-yl)ethyl]-amino}propyl]pyrrolidin-1-yl}-5-methyl-1-oxoheptan-4-yl]-N-methyl-L-valinamide trifluoroacetic acid salt (intermediate 22) was dissolved in 0.6 mL dioxane/water (1:1) and reacted with a 15% aqueous solution of 4-oxobutanoic acid in the presence of sodium cyanoborohydride in a process similar to the synthesis process in Example 1. After lyophilization from dioxane, 14.8 mg (89% of the theoretical) of the title compound was obtained in the form of a white solid.

HPLC (method 10): $R_t$=2.54 min;
LC-MS (method 1): $R_t$=0.92 min; MS (ESIpos): m/z=919 (M+H)$^+$.

The title compound was synthesized by analogy with the synthesis process of Example 1 by reacting 100 mg (119 μmol) N-methyl-L-valyl-N-[(3R,4S,5S)-1-{(2S)-2-[(1R,2R)-3-{[2-(1H-indol-3-yl)ethyl]amino}-1-methoxy-2-methyl-3-oxopropyl]pyrrolidin-1-yl}-3-methoxy-5-methyl-1-oxoheptan-4-yl]-N-methyl-L-valinamide trifluoroacetic acid salt (intermediate 24) with a 15% aqueous solution of 4-oxobutanoic acid in the presence of sodium cyanoborohydride.

Yield: 50 mg (49% of the theoretical)

LC-MS (method 1): $R_t$=0.87 min; MS (ESIpos): m/z=814 (M+H)$^+$.

Example 7

N-(3-Carboxypropyl)-N-methyl-L-valyl-N-[(3R,4S,5S)-1-{(2S)-2-[(1R,2R)-3-{[2-(1H-indol-3-yl)ethyl]amino}-1-methoxy-2-methyl-3-oxopropyl]pyrrolidin-1-yl}-3-methoxy-5-methyl-1-oxoheptan-4-yl]-N-methyl-L-valinamide

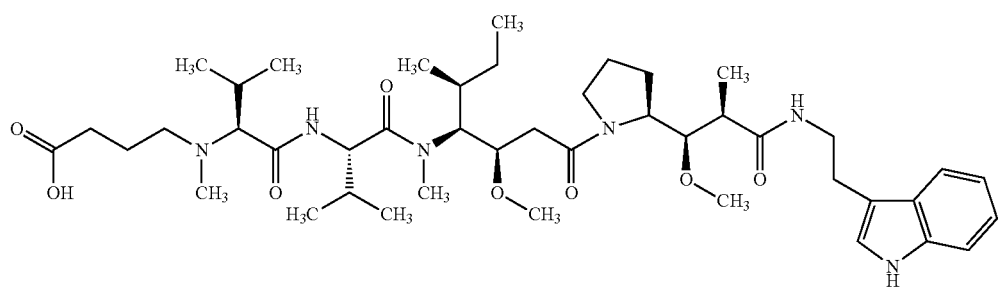 [SMILES: CC[C@H](C)[C@@H]([C@@H](CC(=O)N1CCC[C@H]1[C@H](OC)[C@@H](C)C(=O)NCCc1c[nH]c2ccccc12)OC)N(C)C(=O)[C@@H](NC(=O)[C@H](C(C)C)N(C)CCCC(=O)O)C(C)C]

Example 8

N-(3-Carboxypropyl)-N-methyl-L-valyl-N-[(3R,4S,5S)-3-methoxy-1-{(2S)-2-[(1R,2R)-1-methoxy-2-methyl-3-oxo-3-[(2-phenylethyl)amino]propyl}pyrrolidin-1-yl}-5-methyl-1-oxoheptan-4-yl]-N-methyl-L-valinamide

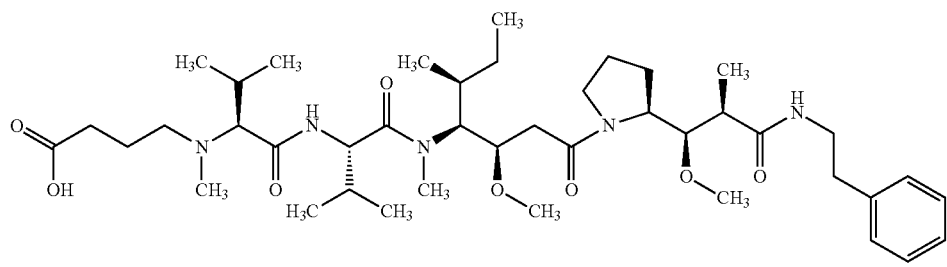 [SMILES: CC[C@H](C)[C@@H]([C@@H](CC(=O)N1CCC[C@H]1[C@H](OC)[C@@H](C)C(=O)NCCc1ccccc1)OC)N(C)C(=O)[C@@H](NC(=O)[C@H](C(C)C)N(C)CCCC(=O)O)C(C)C]

The title compound was synthesized by analogy with the synthesis process of Example 1 by reacting 57 mg (71 μmol) N-methyl-L-valyl-N-[(3R,4S,5S)-3-methoxy-1-{(2S)-2-[(1R,2R)-1-methoxy-2-methyl-3-oxo-3-[(2-phenylethyl)amino]propyl}pyrrolidin-1-yl}-5-methyl-1-oxoheptan-4-yl]-N-methyl-L-valinamide trifluoroacetic acid salt (intermediate 25) with a 15% aqueous solution of 4-oxobutanoic acid in the presence of sodium cyanoborohydride.

Yield: 10 mg (19% of the theoretical)

LC-MS (method 1): $R_t$=0.85 min; MS (ESIpos): m/z=775 $(M+H)^+$.

Example 9

N-(3-Carboxypropyl)-N-methyl-L-valyl-N-[(3R,4S,5S)-1-{(2S)-2-[(1R,2R)-3-{[(1S,2R)-1-hydroxy-1-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide

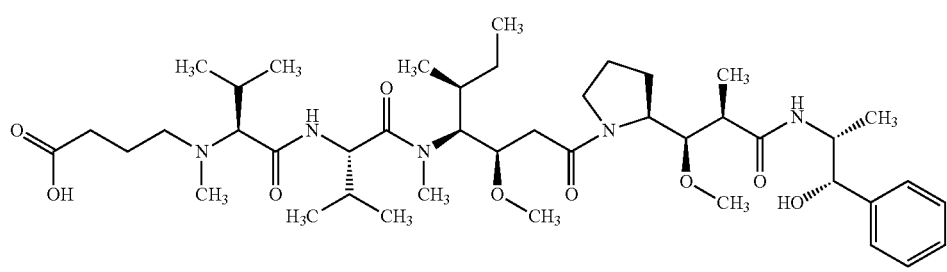 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)CCCC(=O)O)C(C)C]

The title compound was synthesized by analogy with the synthesis process of Example 1 by reacting 57 mg (71 μmol) N-methyl-L-valyl-N-[(3R,4S,5S)-1-{(2S)-2-[(1R,2R)-3-{[(1S,2R)-1-hydroxy-1-phenylpropan-2-yl]amino}-1-methoxy-2-methyl-3-oxopropyl]-pyrrolidin-1-yl}-3-methoxy-5-methyl-1-oxoheptan-4-yl]-N-methyl-L-valinamide trifluoroacetic acid salt [synthesized like intermediate 17 by coupling intermediate 7 with (1S,2R)-(+)-norephedrine and then deprotecting it with trifluoroacetic acid] with a 15% aqueous solution of 4-oxobutanoic acid in the presence of sodium cyanoborohydride.

Yield: 94 mg (84% of the theoretical)

LC-MS (method 1): $R_t$=0.79 min; MS (ESIpos): m/z=805 $(M+H)^+$.

Example 10

N-(3-Carboxypropyl)-N-methyl-L-valyl-N-[(3R,4S,5S)-3-methoxy-1-{(2S)-2-[(1R,2R)-1-methoxy-3-({(2S,3E)-4-[4-(methoxycarbonyl)phenyl]-1-phenylbut-3-en-2-yl}amino)-2-methyl-3-oxopropyl]pyrrolidin-1-yl}-5-methyl-1-oxoheptan-4-yl]-N-methyl-L-valinamide

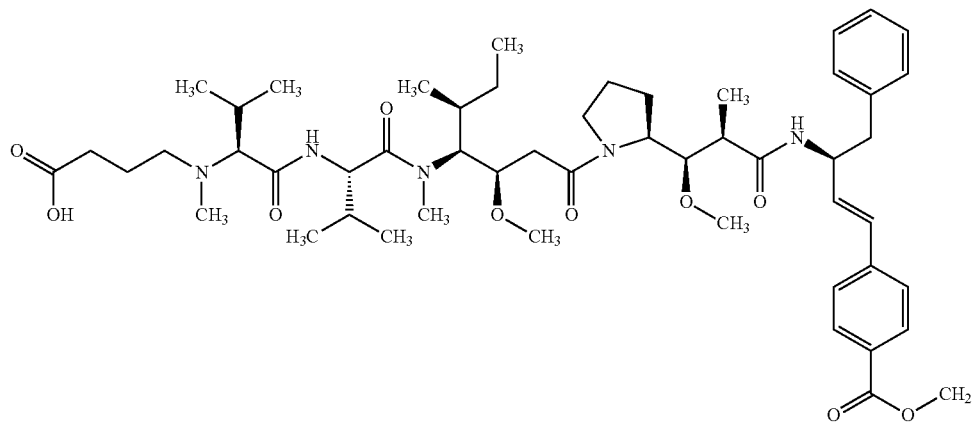 [SMILES: CC[C@H](C)[C@@H]([C@@H](CC(=O)N1CCC[C@H]1[C@H](OC)[C@@H](C)C(=O)N[C@H](/C=C/c1ccc(C(=O)OC)cc1)Cc1ccccc1)OC)N(C)C(=O)[C@@H](NC(=O)[C@H](C(C)C)N(C)CCCC(=O)O)C(C)C]

The title compound was synthesized by analogy with the synthesis process of Example 1 by reacting 45 mg (47 µmol) N-methyl-L-valyl-N-[(3R,4S,5S)-3-methoxy-1-{(2S)-2-[(1R,2R)-1-methoxy-3-{[(2S,3E)-4-[4-(methoxycarbonyl)phenyl]-1-phenylbut-3-en-2-yl}amino)-2-methyl-3-oxopropyl]pyrrolidin-1-yl}-5-methyl-1-oxoheptan-4-yl]-N-methyl-L-valinamide trifluoroacetic acid salt (intermediate 23) with a 15% aqueous solution of 4-oxobutanoic acid in the presence of sodium cyanoborohydride.

Yield: 33.9 mg (78% of the theoretical)

LC-MS (method 1): $R_t$=1.02 min; MS (ESIpos): m/z=933 (M+H)$^+$.

Example 11

N-(3-Carboxypropyl)-N-methyl-L-valyl-N-[(3R,4S,5S)-1-{(2S)-2-[(1R,2R)-3-{[2S,3E)-4-(4-carboxyphenyl)-1-phenylbut-3-en-2-yl]amino}-1-methoxy-2-methyl-3-oxopropyl]-pyrrolidin-1-yl}-3-methoxy-5-methyl-1-oxoheptan-4-yl]-N-methyl-L-valinamide

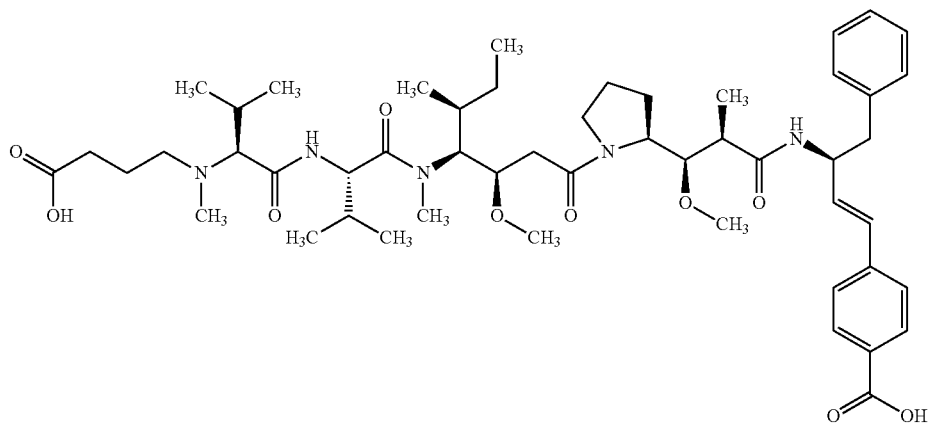 [SMILES: CC[C@H](C)[C@@H]([C@@H](CC(=O)N1CCC[C@H]1[C@H](OC)[C@@H](C)C(=O)N[C@H](/C=C/c1ccc(C(=O)O)cc1)Cc1ccccc1)OC)N(C)C(=O)[C@@H](NC(=O)[C@H](C(C)C)N(C)CCCC(=O)O)C(C)C]

33.9 mg (36 µmol) N-(3-carboxypropyl)-N-methyl-L-valyl-N-[(3R,4S,5S)-3-methoxy-1-{(2S)-2-[(1R,2R)-1-methoxy-3-({(2S,3E)-4-[4-(methoxycarbonyl)phenyl]-1-phenylbut-3-en-2-yl}amino)-2-methyl-3-oxopropyl]pyrrolidin-1-yl}-5-methyl-1-oxoheptan-4-yl]-N-methyl-L-valinamide (Example 10) was placed in 1.1 mL THF/water (1:1) and mixed with 3.5 mg (145 μmol) lithium hydroxide. The reaction mixture was stirred over night at RT, then acidified by adding 1N hydrochloric acid and extracted twice with 10 mL each time. The combined organic phases were dried over magnesium sulfate and concentrated, yielding 18.3 mg (84% purity, 46% of the theoretical) of the title compound.

LC-MS (method 9): $R_t$=4.98 min; MS (ESIpos): m/z=919 (M+H)$^+$.

B. Evaluation of Biological Efficacy

The biological activity of the compounds according to the invention can be demonstrated by in vitro and in vivo investigations, such as those with which those skilled in the art are familiar. For example, the pharmacological and pharmacokinetic properties of the compounds can according to the invention be determined with the help of the assays described below.

B-1. Determination of the Antiproliferative Effect on the HT29 Wt Cell Line:

A defined cell count of the human colon carcinoma cell line HT29 wt (wild type) was sown in a 96-well microtiter plate in whole medium (10% FCS-RPMI) (2500 cells/well) and incubated overnight at 37° C./5% $CO_2$. After 18 hours, the inoculation medium was replaced by fresh medium with 10% FCS. The treatment started with addition of the respective test substance. Of the substances to be investigated, dose-effect curves were determined in a concentration range of $10^{-5}$ M to $10^{-14}$ M (1:10 dilution series). Incubation times of 48 h to 96 h were selected. Proliferation was detected with the help of the MTT assay (ATCC, Manassas, Va., USA, catalog no. 30-1010K). After the end of the selected incubation time, the MTT reagent was incubated with the cells for 4 h before lysis of the cells was performed overnight by adding the detergent. The dye that was formed was detected at 570 nm. The proliferation with otherwise identically treated cells but not with the test substance was defined as the 100% value. The data obtained from this test represents triple determinations, and at least two independent experiments were performed.

The $IC_{50}$ values of representative exemplary embodiments from this assay are listed in Table 1 below:

TABLE 1

| Exemplary embodiment | $IC_{50}$ [nM] |
| --- | --- |
| 1 | 15 |
| 2 | 3.3 |
| 3 | 0.3 |
| 4 | 1.1 |
| 5 | 0.1 |
| 6 | 0.1 |
| 8 | 0.5 |
| 9 | 6 |
| 11 | 4.5 |

In comparison with this, monomethylauristatin F (MMAF) had an $IC_{50}$ value of 10 nM in this test.

B-2. Determination of the Influence on Tubulin Polymerization

Cancer cells are degenerate or neoplastic cells, which often lead to development of a tumor through increased cell division. Microtubules form the spindle fibers of the spindle apparatus and are an essential component of the cell cycle. Regulated buildup and breakdown of microtubule permit an accurate distribution of chromosomes to the daughter cells and represent a continuous dynamic process. A disturbance in these dynamics leads to faulty cell division and ultimately to cell death. However, the increased cell division of cancer cells makes them especially susceptible to spindle fiber toxins, which are a fixed component of chemotherapy. Spindle fiber toxins such as paclitaxel or epothilone lead to a greatly increased rate of polymerization of the microtubules, whereas vinca alkaloids or monomethylauristatin E (MMAE) will lead to a greatly reduced rate of polymerization of the microtubules. In both cases, the necessary dynamics of the cell cycle are sensitive to disturbance. The compounds investigated in the context of the present invention lead to a reduced rate of polymerization of the microtubules.

The "Fluorescence-based Microtubule Polymerization Assay Kit" from the company Cytoskeleton (Denver, Colo., USA; order no. BK011) was used to investigate tubulin polymerization. In this assay, GTP is added to unpolymerized tubulin, so the polymerization can take place spontaneously. The assay is based on the binding of the fluorophore 4',6-diamidino-2-phenylindole (DAPI) to tubulin. Free and bound DAPI can be differentiated on the basis of different emission spectra. DAPI has a much higher affinity for polymerized tubulin in comparison with unpolymerized tubulin, so tubulin polymerization can be tracked on the basis of the increase in the fluorescence of bound DAPI fluorophores.

To perform this assay, the test substances dissolved in DMSO were diluted in water from their initial concentration of 10 mM to 1 μM. In addition to the buffer controls, polymerization-increasing paclitaxel and polymerization-inhibiting vinblastine were also included as assay controls. For the measurement, 96-well plates with a half bottom area were used, tracking the kinetics of the tubulin polymerization for one hour at 37° C. in a fluorimeter. The excitation wavelength was 355 nm, and the emission was tracked at 460 nm. For the range of the linear rise within the first 10 minutes, the change in fluorescence per minute (ΔF/min) was calculated, representing the rate of polymerization of the microtubules. The potency of the test substances was quantified on the basis of the respective reduction in the rate of polymerization.

B-3. Determination of the Plasma Stability In Vitro
Method A:

Of the respective test substance, 1 mg was dissolved in 0.5 mL acetonitrile/DMSO (9:1). Of this solution, 20 μL was removed and added to 1 mL rat plasma and human plasma at 37° C. (plasma of male Wistar rats with Li heparin, Harlan & Winkelmann and/or human leukocyte-depleted fresh plasma from whole blood specimens). Immediately after adding the specimen (initial value as reference variable) and then after 5, 10, 30, 60, 120, 180 and 240 minutes and optionally also after 24 hours, 100 μL aliquots were taken and added to 300 μL acetonitrile. The precipitated plasma proteins were centrifuged for 10 minutes at 5000 rpm, and then 30 μL of the supernatant was analyzed by HPLC to determine its unchanged test substance content. The results were quantified based on area percent of the corresponding peaks.

HPLC Method on Rat Plasma:

Instrument: Agilent 1200 with DAD, binary pump, autosampler, column oven and thermostat; column: Kromasil 100 C18, 250 mm×4 mm, 5 μm; column temperature: 45° C.; eluent A: 5 mL perchloric acid/L water; eluent B: acetonitrile; gradient: 0-8 min 98% A, 2% B: 8-15 min 56% A, 44% B; 15-20 min 10% A, 90% B; 20-21 min 10% A, 90% B; 21-23 min 98% A, 2% B; 23-25 min 98% A, 2% B; flow rate: 2 mL/min; UV detection: 220 nm.

HPLC Method on Human Plasma:

Instrument: Agilent 1100 with DAD, binary pump, autosampler, column over and thermostat; column: Kromasil 100 C18, 250 mm×4 mm, 5 μm; column temperature: 45° C.; eluent A: 5 mL perchloric acid/L water; eluent B: acetonitrile;

gradient: 0-3 min 98% A, 2% B; 3-10 min 65% A, 35% B; 10-15 min 40% A, 60% B; 15-21 min 10% A, 90% B; 21-22 min 10% A, 90% B; 22-24 min 98% A, 2% B; 24-26 min 98% A, 2% B; flow rate 2 mL/min; UV detection: 220 nm.
Method B:

The respective test substance was incubated in rat plasma and/or human plasma at 37° C. for a period of 5 h while stirring lightly. At various points in time (0, 2, 5, 10, 20, 30, 60, 120, 180 and 300 minutes), a 100 µL aliquot was taken. After adding an internal standard (10 µL), the proteins were precipitated by adding 200 µL and the mixture was centrifuged for 5 minutes in an Eppendorf centrifuge. After adding 150 µL ammonium acetate buffer, pH 3, to 150 µL of the supernatant, the unchanged test substance content was analyzed by LC/MSMS.

B-4. Determination of Cell Permeability:

The cell permeability of a substance can be analyzed by in vitro testing in a flux assay using Caco-2 cells [M. D. Troutman and D. R. Thakker, *Pharm. Res.* 20 (8), 1210-1224 (2003)]. To do so, the cells were cultured for 15-16 days on 24-hole filter plates. To determine the permeation, the respective test substance was applied to the cells either apically (A) or basally (B) in a HEPES buffer and incubated for 2 h. After 0 h and after 2 h, samples were taken from the cis- and trans-compartments. The samples were separated by HPLC (Agilent 1200, Böblingen, Germany) using reverse phase columns. The HPLC system was coupled via a turbo ion spray interface to an API 4000 triple quadrupole mass spectrometer (Applied Biosystems Applera, Darmstadt, Germany). The permeability was evaluated on the basis of a $P_{app}$ value, which was calculated using the equation published by Schwab et al. [D. Schwab et al., *J. Med. Chem.* 46, 1717-1725 (2003)]. A substance was classified as being actively transported if the ratio of $P_{app}$ (B–A) to $P_{app}$ (A–B) was >2 or <0.5.

The permeability of B to A [$P_{app}$ (B–A)] is of crucial importance for toxophores that are released intracellularly. The lower this permeability, the longer is the dwell time of the substance in the cell after intracellular release and thus also the time available for an interaction with the biochemical target (here: tubulin).

Table 2 below shows permeability data for representative exemplary embodiments from this assay:

TABLE 2

| Exemplary embodiment | $P_{app}$ (B-A) [nm/s] |
|---|---|
| 2 | 157 |
| 3 | 179 |
| 4 | 19 |
| 5 | 29 |
| 6 | 45 |
| 7 | 11 |
| 8 | 10 |
| 9 | 4.5 |
| 11 | 2 |

In comparison with this, monomethylauristatin E (MMAE) and monomethylauristatin F (MMAF) had a $P_{app}$ value of 89 nm/s or 73 nm/s, respectively, in this test.

B-5. Determination of the Substance Properties for P-Glycoprotein (P-gp):

Many tumor cells express transporter proteins for active ingredients and drugs, which is often associated with development of a resistance to cytostatics. Substances that are not substrates of such transporter proteins, such as P-glycoprotein (P-gp) or BCRP could thus have an improved profile of effect.

The substrate properties of a substance for P-gp (ABCB1) were determined by means of a flux assay using LLC-PK1 cells which overexpress P-gp (L-MDR1 cells) [A. H. Schinkel et al., *J. Clin. Invest.* 96, 1698-1705 (1995)]. To do so, the LLC-PK1 cells or L-MDR1 cells were cultured for 3-4 days on 96-well filter plates. To determine the permeation, the respective test substance, either alone or in the presence of an inhibitor (e.g., ivermectin or verapamil) in a HEPES buffer was applied to the cells either apically (A) or basally (B) and incubated for 2 h. After 0 h and after 2 h, samples were taken from the cis- and trans-compartments. The samples were separated by HPLC using reverse phase columns. The HPLC system was coupled via a turbo ion spray interface to an API 3000 triple quadrupole mass spectrometer (Applied Biosystems Applera, Darmstadt, Germany). The permeability was evaluated on the basis of a $P_{app}$ value, which was calculated using the equation published by Schwab et al. [D. Schwab et al., *J. Med. Chem.* 46, 1716-1725 (2003)]. A substance was classified as being a P-gp substrate if the efflux ratio $P_{app}$ (B–A) to $P_{app}$ (A–B) was >2.

The efflux ratios in L-MDR1 and LLC-PK1 cells or the efflux ratio in the presence or absence of an initiator can be compared with one another as additional criteria for evaluating the P-gp substrate properties. If these values differ by more than a factor of 2, then the respective substance is a P-gp substrate.

C. Exemplary Embodiments for Pharmaceutical Compositions

The compounds according to the invention may be converted to pharmaceutical preparations by the following method:

Tablet:
Composition:
100 mg of the compound according to the invention, 50 mg lactose (monohydrate), 50 mg cornstarch (native), 10 mg polyvinylpyrrolidone (PVP 25) (BASF, Ludwigshafen, Germany) and 2 mg magnesium stearate Tablet weight 212 mg; diameter 8 mm; radius of curvature 12 mm.

Preparation:
The mixture of the compound according to the invention, lactose and starch is granulated with a 5% solution (w/w) of the PVP in water. The granules are mixed with the magnesium stearate for five minutes after drying. This mixture is pressed with a conventional tablet press (see above for the format of the tablet). A pressing force of 15 kN was used as the guideline value for pressing the tablets.

Suspension for Oral Administration:
Composition:
1000 mg of the compound according to the invention, 1000 mg ethanol (96%), 400 mg Rhodigel® (xanthan gum from FMC, Pennsylvania, USA) and 99 g water.

10 mL oral suspension corresponds to a single dose of 100 mg of the compound according to the invention.

Solution for Oral Administration:
Composition:
500 mg of the compound according to the invention, 2.5 g polysorbate and 97 g polyethylene glycol 400.20 g of the oral solution corresponds to a single dose of 100 mg of the compound according to the invention.

Preparation:
The compound according to the invention is suspended in the mixture of polyethylene glycol and polysorbate while stirring. The stirring process is continued until the compound according to the invention is completely dissolved.

i.v. Solution:

The compound according to the invention is dissolved in a concentration below the saturation solubility in a physiologically tolerable solvent (e.g., isotonic saline solution, glucose solution 5% and/or PEG 400 solution 30%). The solution is sterile filtered and bottled in sterile and pyrogen-free injection vials.

The invention claimed is:
1. A compound of formula (I)

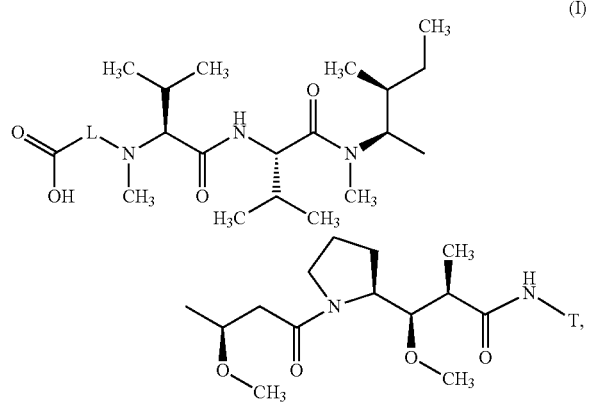

(I)

or a salt or solvate thereof, in which

L is linear $(C_1-C_{12})$-alkanediyl, which may be substituted with methyl up to four times and in which (a) two carbon atoms in 1,2-, 1,3- or 1,4-relation to one another are optionally bridged by including the carbon atoms optionally between them to form a $(C_3-C_6)$-cycloalkyl ring or a phenyl ring, or (b) up to three $CH_2$ groups not vicinal to one another are optionally replaced by —O—,
and
T is a group of the formula

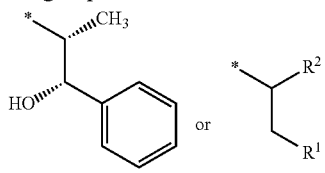

wherein
* denotes the linkage site to the nitrogen atom,
$R^1$ is phenyl or 1H-indol-3-yl,
and
$R^2$ is hydrogen or a group of the formula

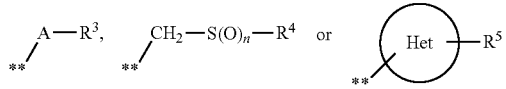

wherein
** denotes the respective linkage site to the radical of the respective group T,
A is linear $(C_1-C_4)$-alkanediyl or linear $(C_2-C_4)$-alkenediyl,
$R^3$ is phenyl that is optionally substituted with $(C_1-C_4)$-alkoxycarbonyl or carboxyl,
n is the number 0, 1 or 2,
$R^4$ is phenyl, benzyl or 2-phenylethyl which is optionally substituted with $(C_1-C_4)$-alkoxycarbonyl or carboxyl in the phenyl group
Het is a divalent 5-membered heteroaryl ring with up to three ring heteroatoms from the series N, O and/or S,
and
$R^5$ is $(C_3-C_6)$-cycloalkyl, phenyl or $(C_1-C_4)$-alkyl, which is optionally substituted with phenyl, wherein the aforementioned phenyl groups are optionally substituted with $(C_1-C_4)$-alkoxycarbonyl or carboxyl.

2. The compound of claim 1 or a salt or solvate thereof, wherein
L is linear $(C_1-C_8)$-alkanediyl, in which (a) two carbon atoms in 1,3- or 1,4-relation to one another are optionally bridged by including one or two of the carbon atoms between them to form a phenyl ring, or (b) up to two $CH_2$ groups not vicinal to one another are optionally replaced by —O—,
and
T is a group of the formula

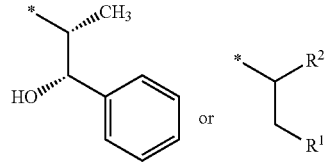

wherein
* denotes the linkage site to the nitrogen atom,
$R^1$ is phenyl or 1H-indol-3-yl,
and
$R^2$ is hydrogen or a group of the formula

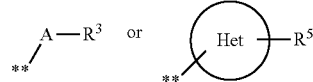

wherein
** denotes the linkage site to the radical of the respective group T,
A is ethene-1,2-diyl or propene-1,3-diyl,
$R^3$ is phenyl, which is optionally substituted with $(C_1-C_4)$-alkoxycarbonyl or carboxyl,
Het is a divalent 5-membered heteroaryl ring selected from the series of pyrazolyl, imidazolyl, 1,3-oxazolyl, 1,3-thiazolyl, 1,2,4-oxadiazolyl and 1,3,4-oxadiazolyl,
and
$R^5$ is a phenyl, which is optionally may be substituted with $(C_1-C_4)$-alkoxycarbonyl or carboxyl.

3. The compound of claim 1 or a salt or solvate thereof, wherein
L is linear $(C_1-C_6)$-alkanediyl,
and
T is a group of the formula

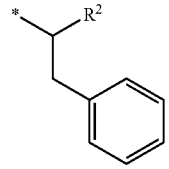

wherein
* denotes the linkage site to the nitrogen atom,
and
$R^2$ is hydrogen or a group of the formula

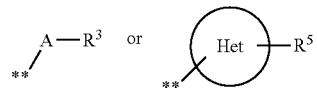

wherein
** denotes the linkage site to the radical of the respective group T,
A is ethene-1,2-diyl,
$R^3$ is phenyl, which is optionally substituted with methoxycarbonyl or carboxyl, Het is 1,3,4-oxadiazol-2,5-yl,
and
$R^5$ is a phenyl, which is optionally substituted with methoxycarbonyl or carboxyl.

4. A method for preparing a compound of claim 1 or a salt or solvate thereof, the method comprising providing a compound of formula (II)

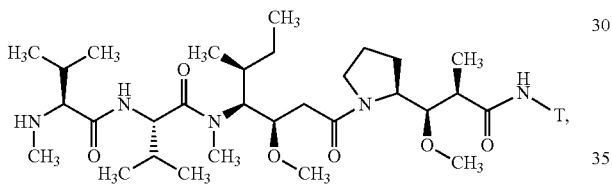

(II)

in which T has the meaning given in claim 1,
and reacting the compound of formula (II) in an inert solvent, either
[A] by base-induced alkylation with a compound of formula (III)

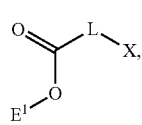

(III)

in which L has the meaning given in claim 1,
$E^1$ is hydrogen, $(C_1$-$C_4)$-alkyl or benzyl, and
X is a leaving group selected from the group consisting of chloride, bromide, iodide, mesylate, triflate, and tosylate,
to form a compound of formula (IV)

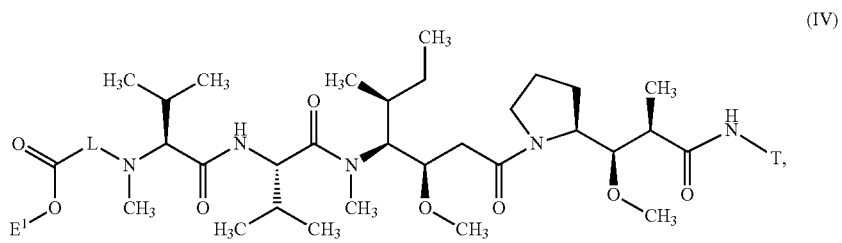

(IV)

in which L and T have the meanings given in claim 1,
and $E^1$ is hydrogen, $(C_1$-$C_4)$-alkyl or benzyl, wherein, when $E^1$ is $(C_1$-$C_4)$-alkyl or benzyl, the ester radical is removed, thereby producing a hydrogen at $E^1$ in formula (III), thus producing the carboxylic acid of formula (I);
or
[B] with a compound of formula (V)

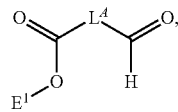

(V)

wherein
$E^1$ is hydrogen, $(C_1$-$C_4)$-alkyl or benzyl,
and
$L^A$ has the meaning of L given in claim 1, but is shortened by one $CH_2$ unit in the alkyl chain length,
in the presence of a suitable reducing agent to produce a compound of formula (VI)

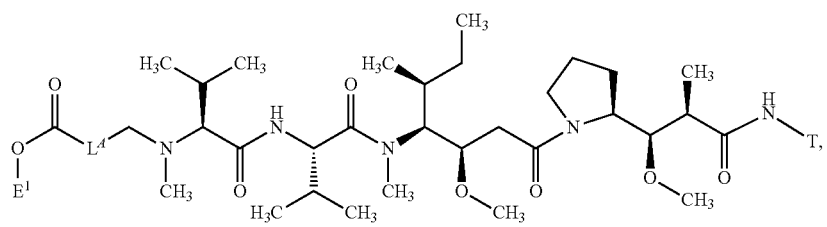

(VI)

in which $L^A$ has the meaning of L given in claim 1, but is shortened by one $CH_2$ unit in the alkyl chain length,
T has the meaning given in claim 1, and
$E^1$ is hydrogen, $(C_1$-$C_4)$-alkyl or benzyl, wherein, when $E^1$ stands for $(C_1$-$C_4)$-alkyl or benzyl, the ester radical is removed, thereby producing a hydrogen at $E^1$ in formula (V), thus producing the carboxylic acid of formula (I-A)

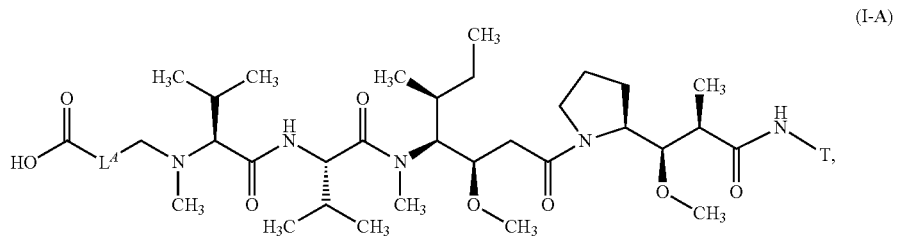

(I-A)

in which $L^A$ has the meaning of L given in claim 1, but is shortened by one $CH_2$ unit in the alkyl chain length, and T has the meaning given in claim 1.

5. A pharmaceutical composition comprising a compound as defined in claim 1 or a salt or solvate thereof, and further comprising one or more inert, non-toxic, pharmaceutically suitable excipients.

6. The pharmaceutical composition of claim 5, further comprising one or more additional active ingredients.

7. A method for the treatment of cancer or tumor conditions in humans or animals, said method comprising administering to a subject an effective amount of at least one compound as defined in claim 1.

8. A method for treatment of cancer or tumor diseases in humans or animals, said method comprising administering to a subject an effective amount of at least one pharmaceutical composition of claim 5.

9. The compound of claim 1, wherein said compound is selected from the group consisting of:

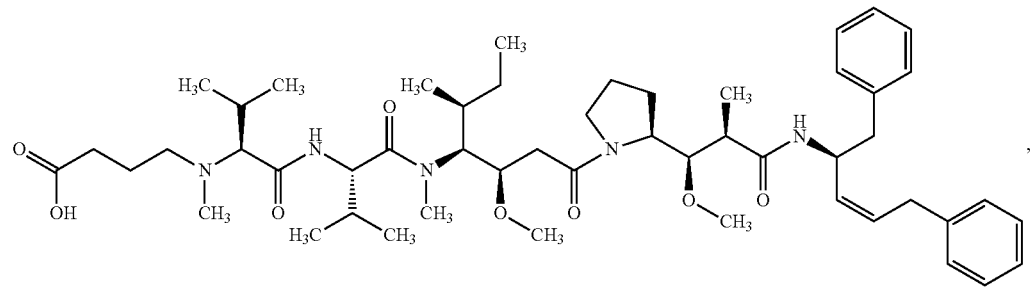

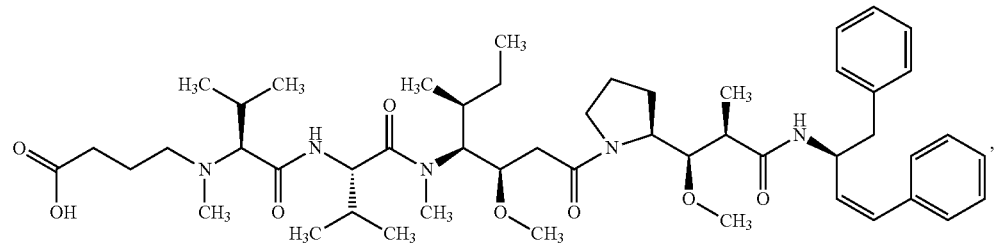

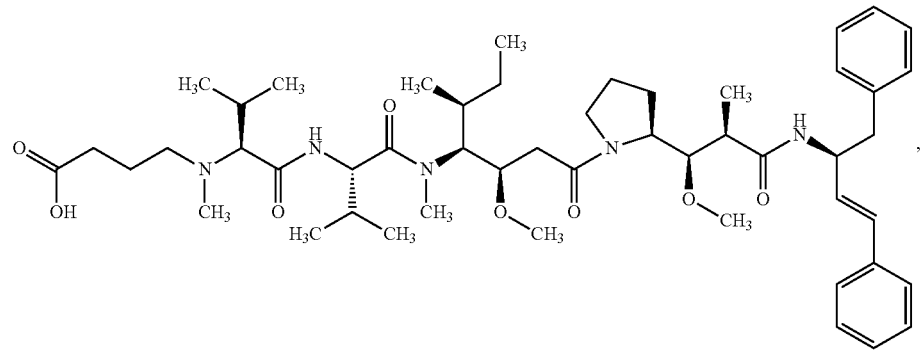

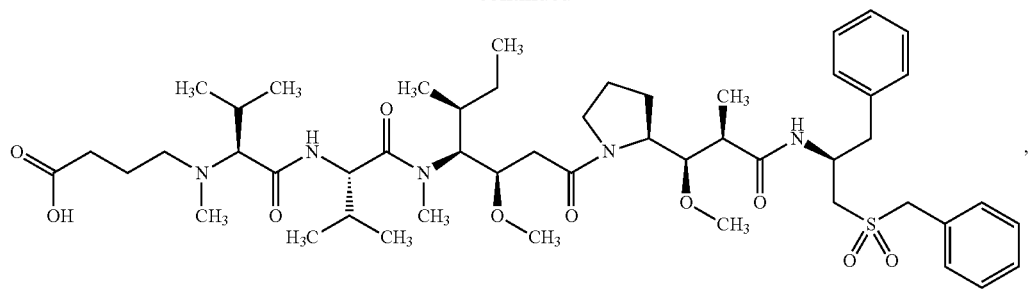
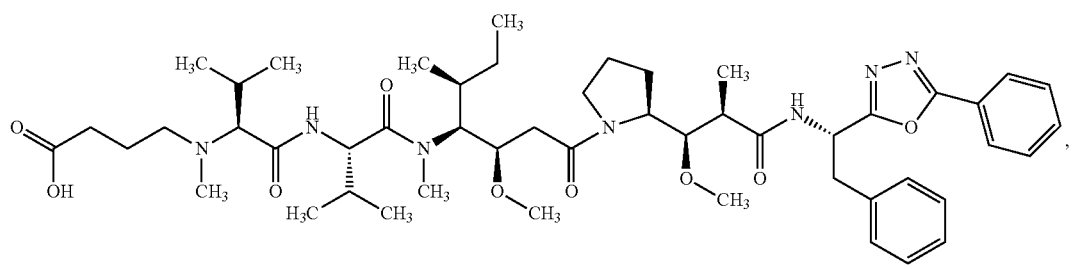
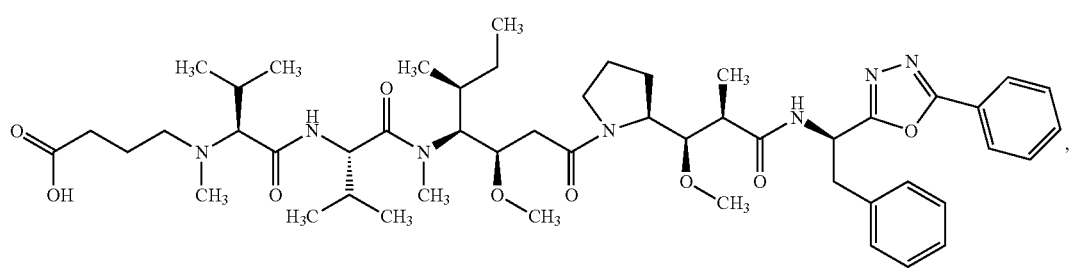
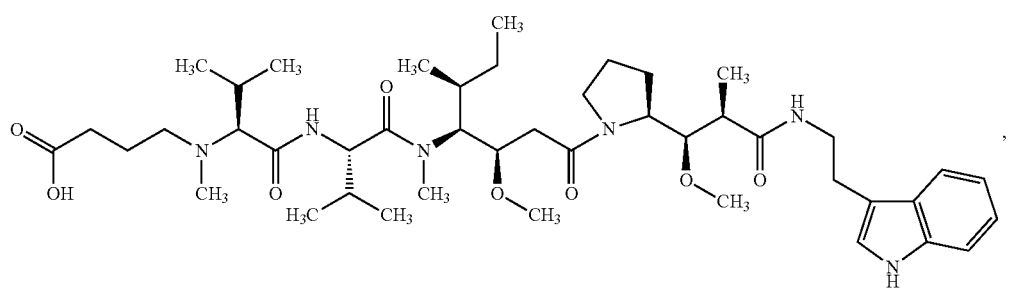
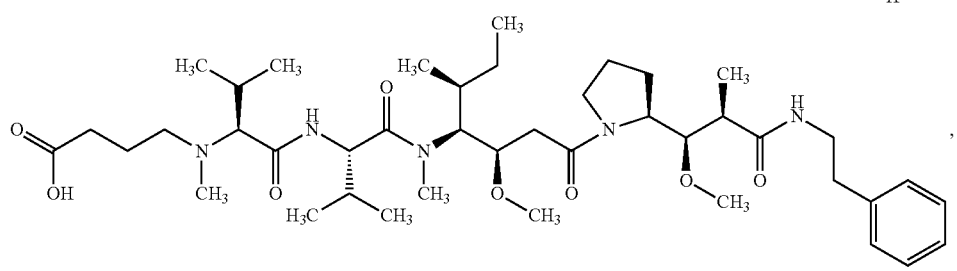
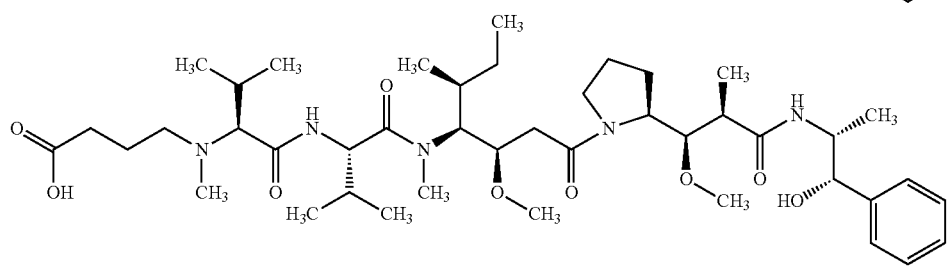

-continued

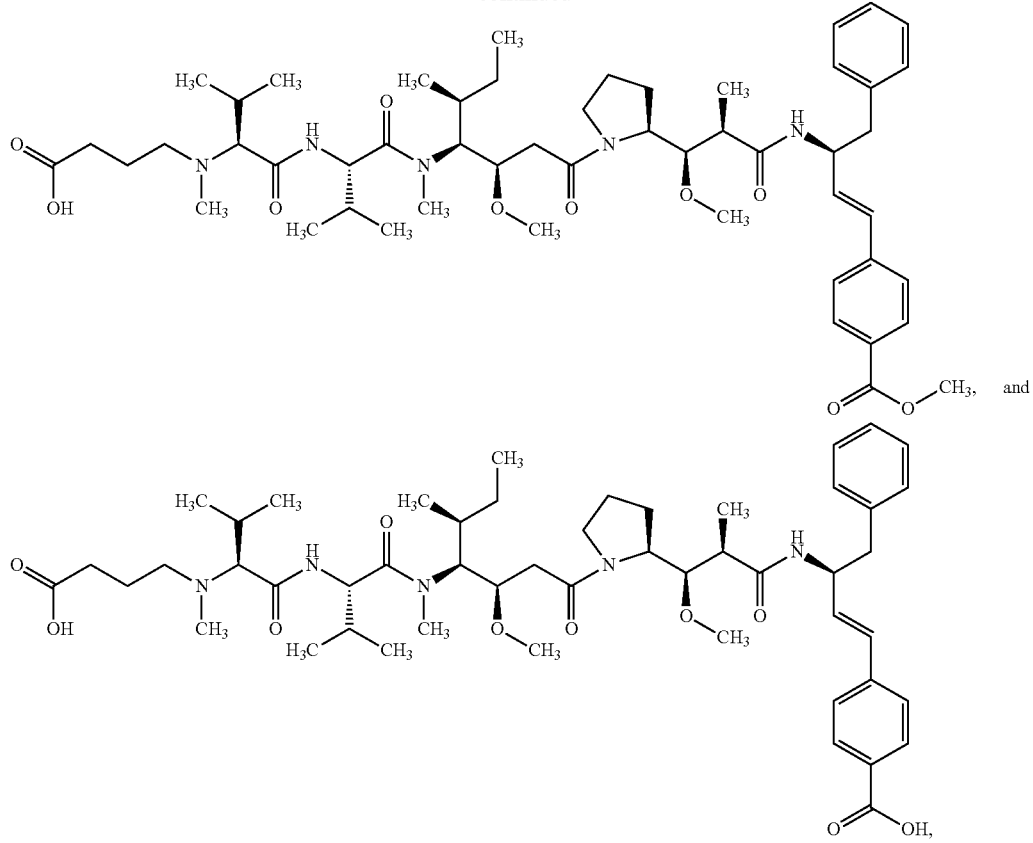

or a salt or solvate thereof.

10. An antiproliferative conjugate in which a compound of claim 1 is connected with a protein.

11. The antiproliferative conjugate according to claim 10, wherein the protein is an antibody.

12. An antiproliferative conjugate in which a compound of claim 8 is connected with a protein.

13. The antiproliferative conjugate according to claim 12, wherein the protein is an antibody.

* * * * *